(12) United States Patent
Bergstrom et al.

(10) Patent No.: US 11,330,843 B2
(45) Date of Patent: May 17, 2022

(54) VAPORIZER APPARATUSES AND VAPORIZING METHODS

(71) Applicant: Bergstrom Innovations, LLC, Merritt Island, FL (US)

(72) Inventors: Sam Bergstrom, Merritt Island, FL (US); Charles Ankner, Greenacres, FL (US); Christopher Teague, Ogden, UT (US); Robert Current, Tucson, AZ (US)

(73) Assignee: Bergstrom Innovations, LLC, Merritt Island, FL (US)

( * ) Notice: Subject to any disclaimer, the term of this patent is extended or adjusted under 35 U.S.C. 154(b) by 0 days.

(21) Appl. No.: 17/191,850

(22) Filed: Mar. 4, 2021

(65) Prior Publication Data

US 2021/0204605 A1 Jul. 8, 2021

Related U.S. Application Data

(63) Continuation of application No. PCT/US2019/049829, filed on Sep. 5, 2019.

(60) Provisional application No. 62/727,820, filed on Sep. 6, 2018.

(51) Int. Cl.
| | |
|---|---|
| *A24F 40/485* | (2020.01) |
| *A24F 40/42* | (2020.01) |
| *A24F 40/57* | (2020.01) |
| *A61M 11/00* | (2006.01) |
| *A61M 16/00* | (2006.01) |
| *A61M 11/04* | (2006.01) |
| *A61M 15/00* | (2006.01) |
| *A24F 7/00* | (2006.01) |
| *A61M 15/06* | (2006.01) |

(52) U.S. Cl.
CPC .............. *A24F 40/485* (2020.01); *A24F 7/00* (2013.01); *A24F 40/42* (2020.01); *A24F 40/57* (2020.01); *A61M 11/042* (2014.02); *A61M 15/0021* (2014.02); *A61M 15/06* (2013.01); *A61M 2205/8206* (2013.01)

(58) Field of Classification Search
CPC ........ A24F 47/00; A24F 47/008; A24F 40/57; A24F 40/485; A24F 40/20; A24F 40/42; A24F 40/10
See application file for complete search history.

(56) References Cited

U.S. PATENT DOCUMENTS

| | | |
|---|---|---|
| 5,195,514 A | 3/1993 | Liu |
| 7,997,280 B2 | 8/2011 | Rosenthal |
| 10,334,881 B1 * | 7/2019 | Conley .................. A24F 40/42 |

(Continued)

FOREIGN PATENT DOCUMENTS

| | | |
|---|---|---|
| WO | 2015021447 A1 | 2/2015 |
| WO | 2015079198 A1 | 6/2015 |

(Continued)

*Primary Examiner* — Alex B Efta
(74) *Attorney, Agent, or Firm* — The Culbertson Group, P.C.

(57) ABSTRACT

Devices and methods for providing inhalable vapor are disclosed. A device may include a body with a first distal and proximal section; a first connector that releasably couples with a cartridge that provides a volatizable material; and a sleeve integral with or releasably coupled to the body, the sleeve defining a first aperture dimensioned to accommodate at least the width of the cartridge.

15 Claims, 57 Drawing Sheets

(56) References Cited

U.S. PATENT DOCUMENTS

| | | |
|---|---|---|
| D870,962 S | 12/2019 | Choe |
| 2002/0067917 A1 | 6/2002 | Takamatsu |
| 2006/0037539 A1 | 2/2006 | Toda |
| 2007/0280652 A1 | 12/2007 | Williams |
| 2008/0092912 A1* | 4/2008 | Robinson ............. A24B 15/167 131/200 |
| 2013/0139813 A1 | 6/2013 | Storz |
| 2013/0276799 A1 | 10/2013 | Davidson et al. |
| 2013/0298905 A1 | 11/2013 | Levin |
| 2014/0299137 A1 | 10/2014 | Kieckbusch |
| 2014/0366898 A1 | 12/2014 | Monsees |
| 2015/0128967 A1 | 5/2015 | Robinson |
| 2016/0100632 A1 | 4/2016 | Debono |
| 2016/0120226 A1* | 5/2016 | Rado ....................... A24F 40/42 131/329 |
| 2016/0183596 A1* | 6/2016 | Rado ....................... A24F 40/44 392/395 |
| 2016/0235122 A1 | 8/2016 | Krietzman |
| 2016/0242466 A1 | 8/2016 | Lord |
| 2016/0262459 A1 | 9/2016 | Monsees |
| 2016/0271347 A1 | 9/2016 | Raichman |
| 2016/0331024 A1 | 11/2016 | Cameron |
| 2016/0331026 A1 | 11/2016 | Cameron |
| 2016/0367925 A1 | 12/2016 | Blackley |
| 2017/0135409 A1 | 5/2017 | Cameron |
| 2017/0136193 A1 | 5/2017 | Cameron |
| 2017/0207499 A1* | 7/2017 | Leadley .............. H01M 10/443 |
| 2017/0208863 A1 | 7/2017 | Tobacco |
| 2017/0258142 A1 | 9/2017 | Hatton |
| 2018/0064171 A1 | 3/2018 | Verleur |
| 2018/0098578 A1 | 4/2018 | Monsees |
| 2018/0104214 A1 | 4/2018 | Raichman |
| 2018/0116291 A1 | 5/2018 | Monsees |
| 2018/0116294 A1 | 5/2018 | Saydar |
| 2018/0168231 A1 | 6/2018 | Reevell |
| 2018/0310630 A1* | 11/2018 | Kleizo ................... A24F 40/40 |

FOREIGN PATENT DOCUMENTS

| | | |
|---|---|---|
| WO | 2016172802 A1 | 11/2016 |
| WO | 2017037457 A1 | 3/2017 |
| WO | 2017121979 A1 | 7/2017 |
| WO | 2017147560 A1 | 8/2017 |
| WO | 2017175218 A2 | 10/2017 |

\* cited by examiner

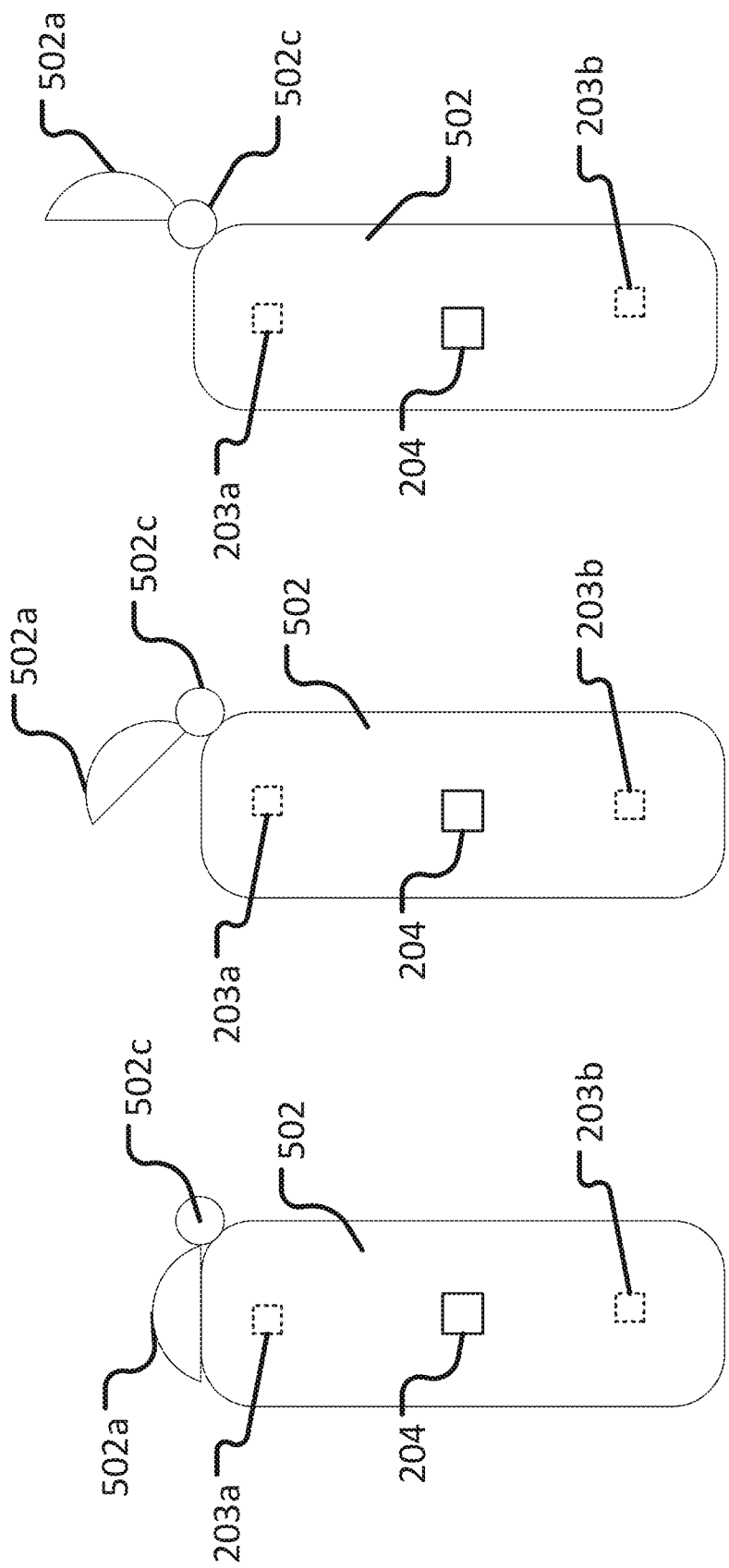

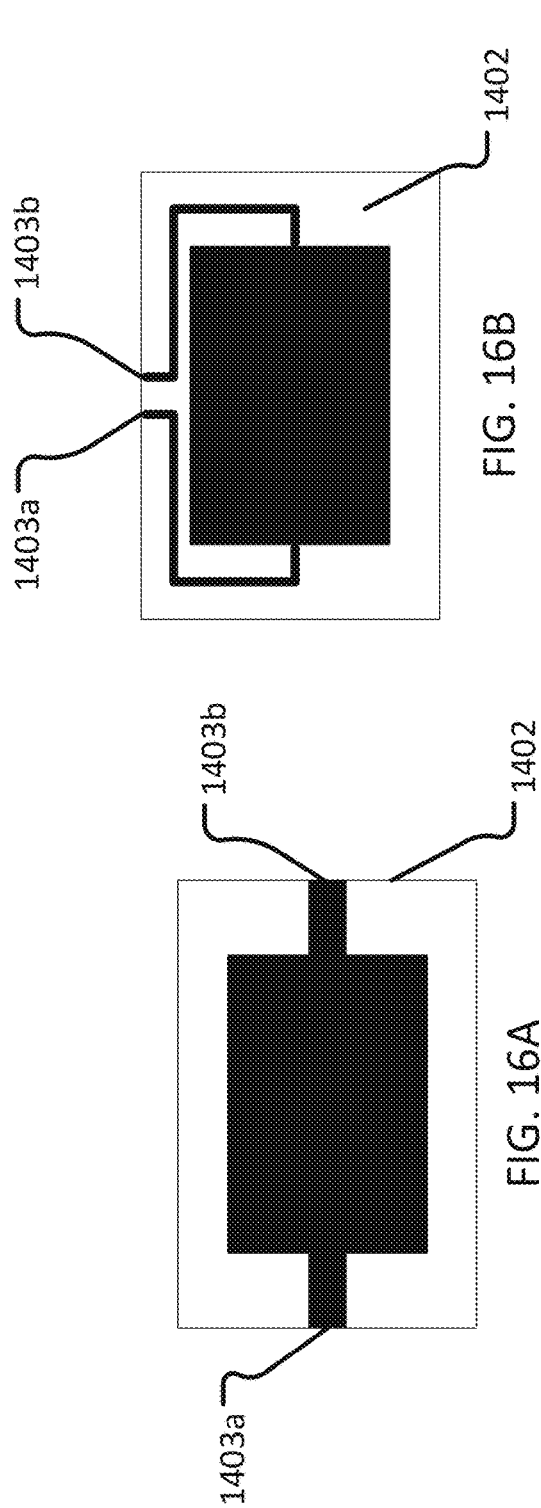

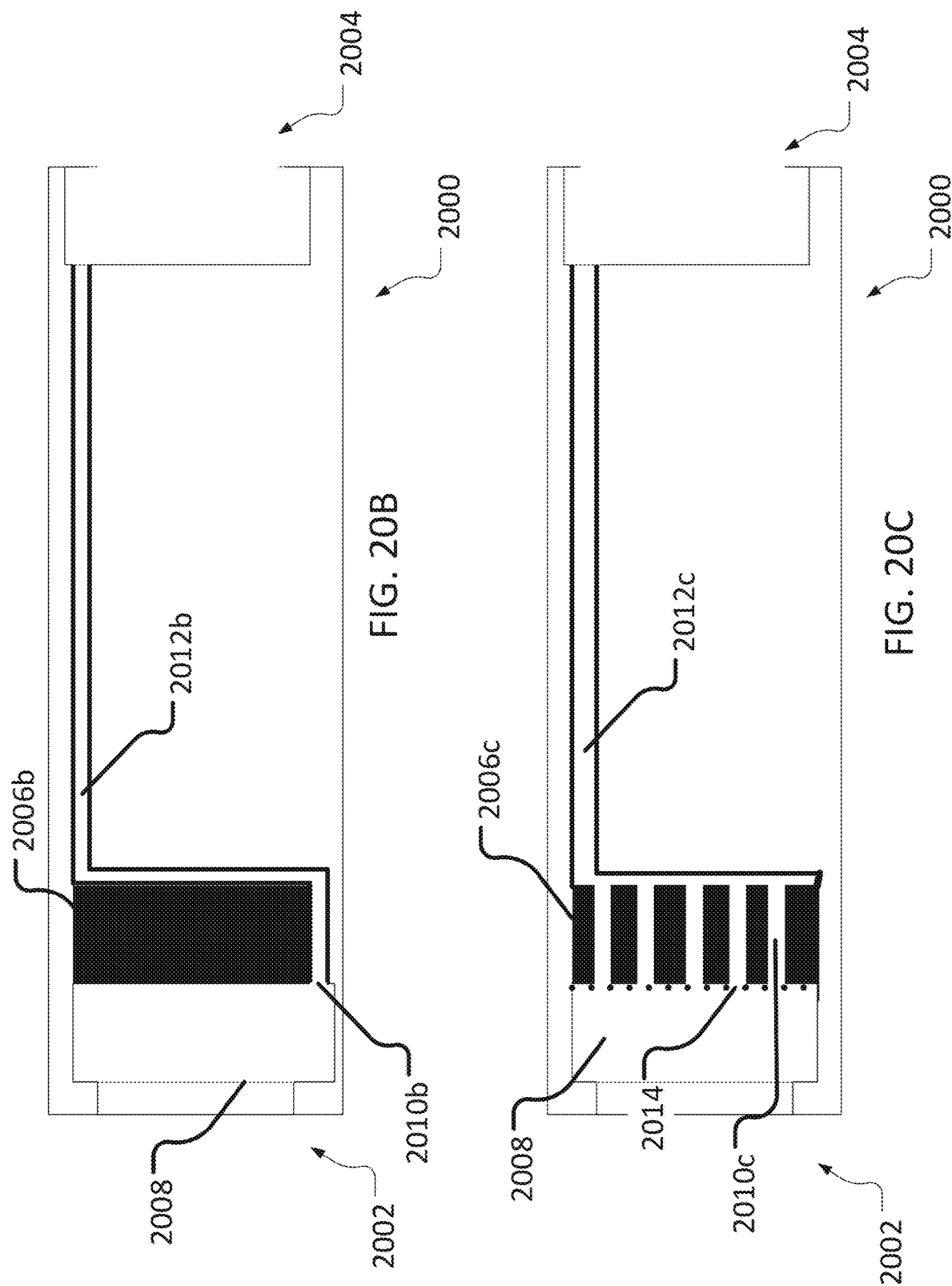

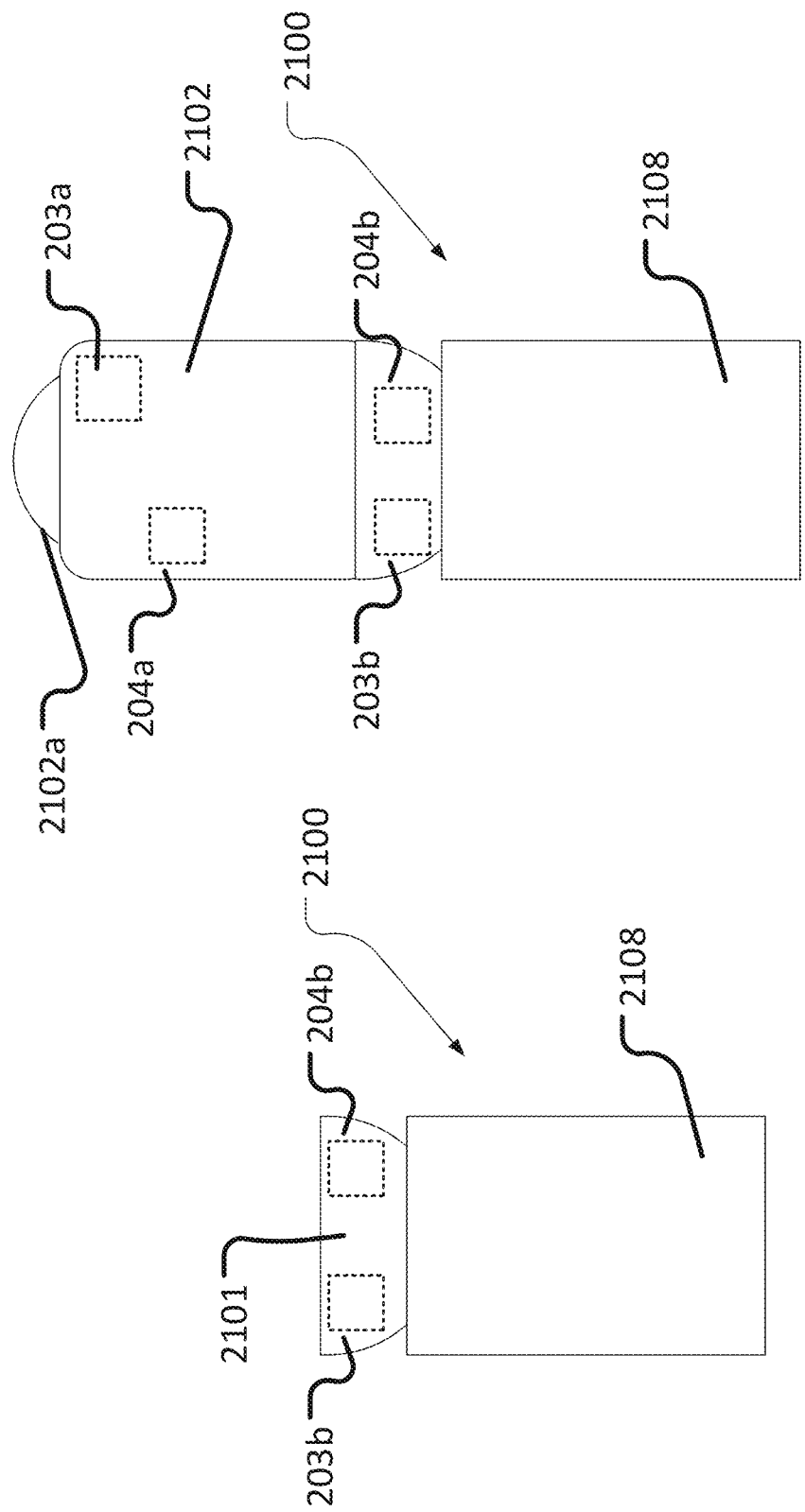

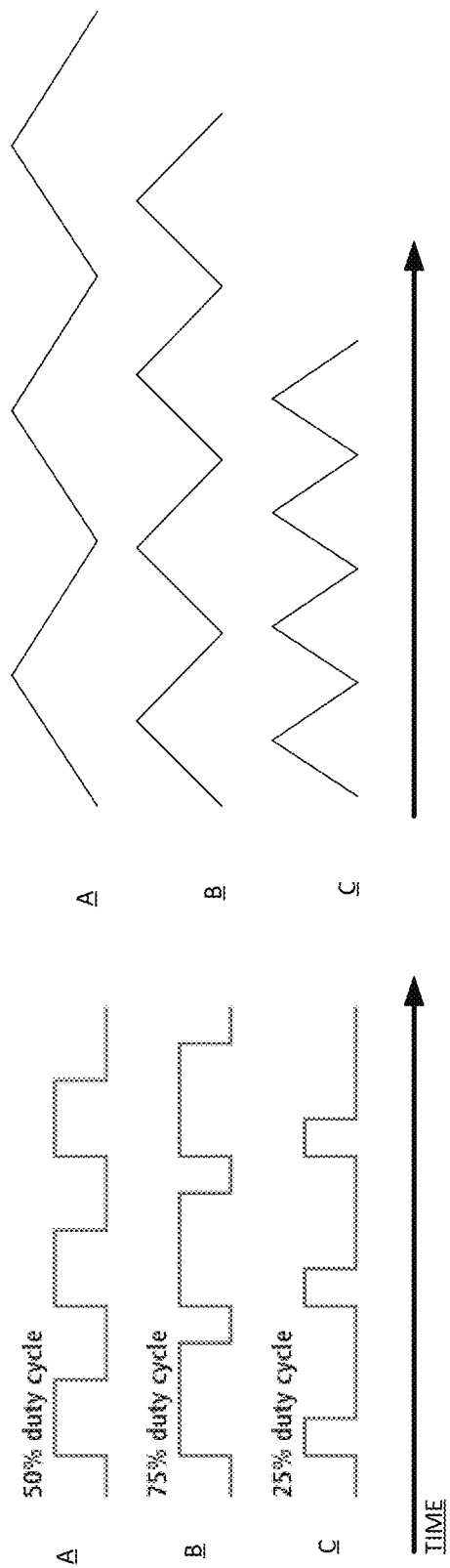
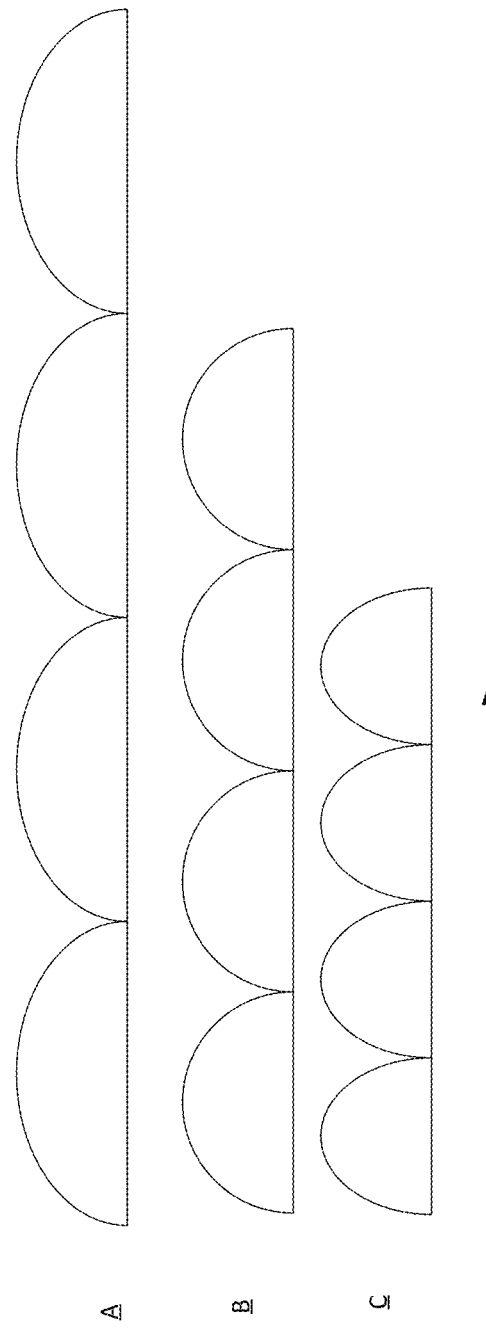
FIG. 31A
FIG. 31B
FIG. 31C

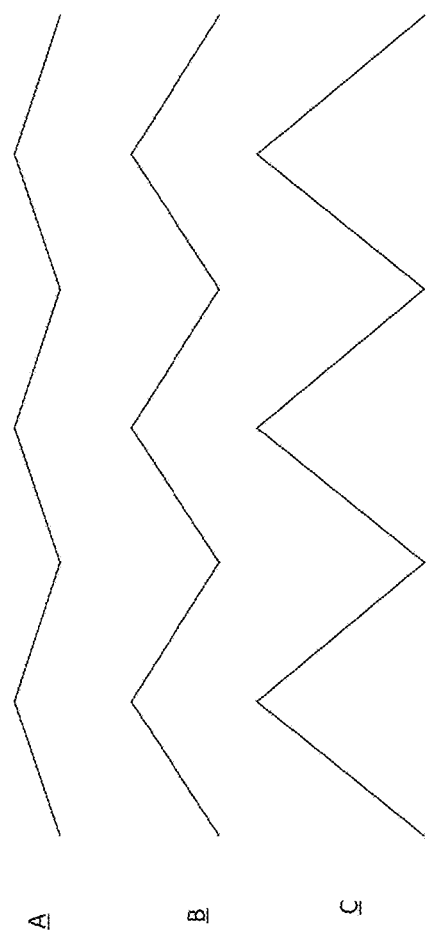
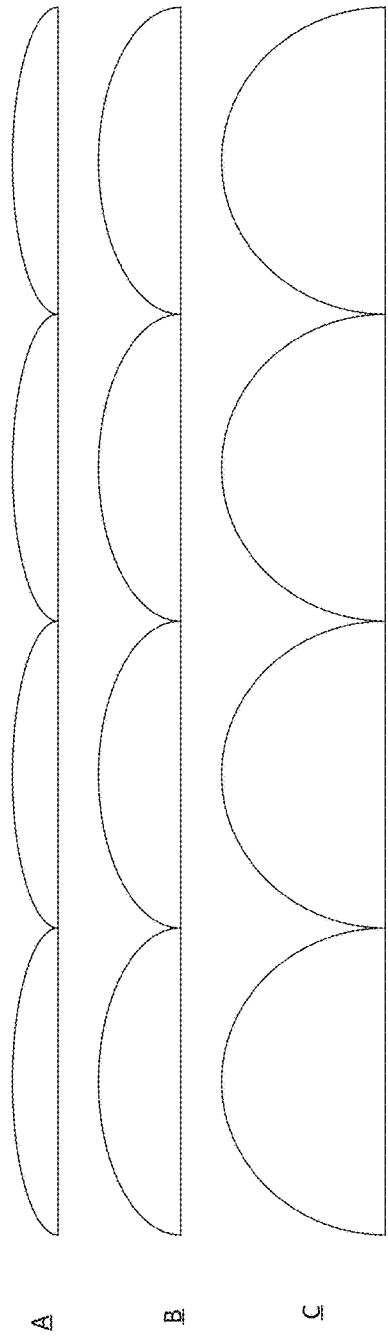

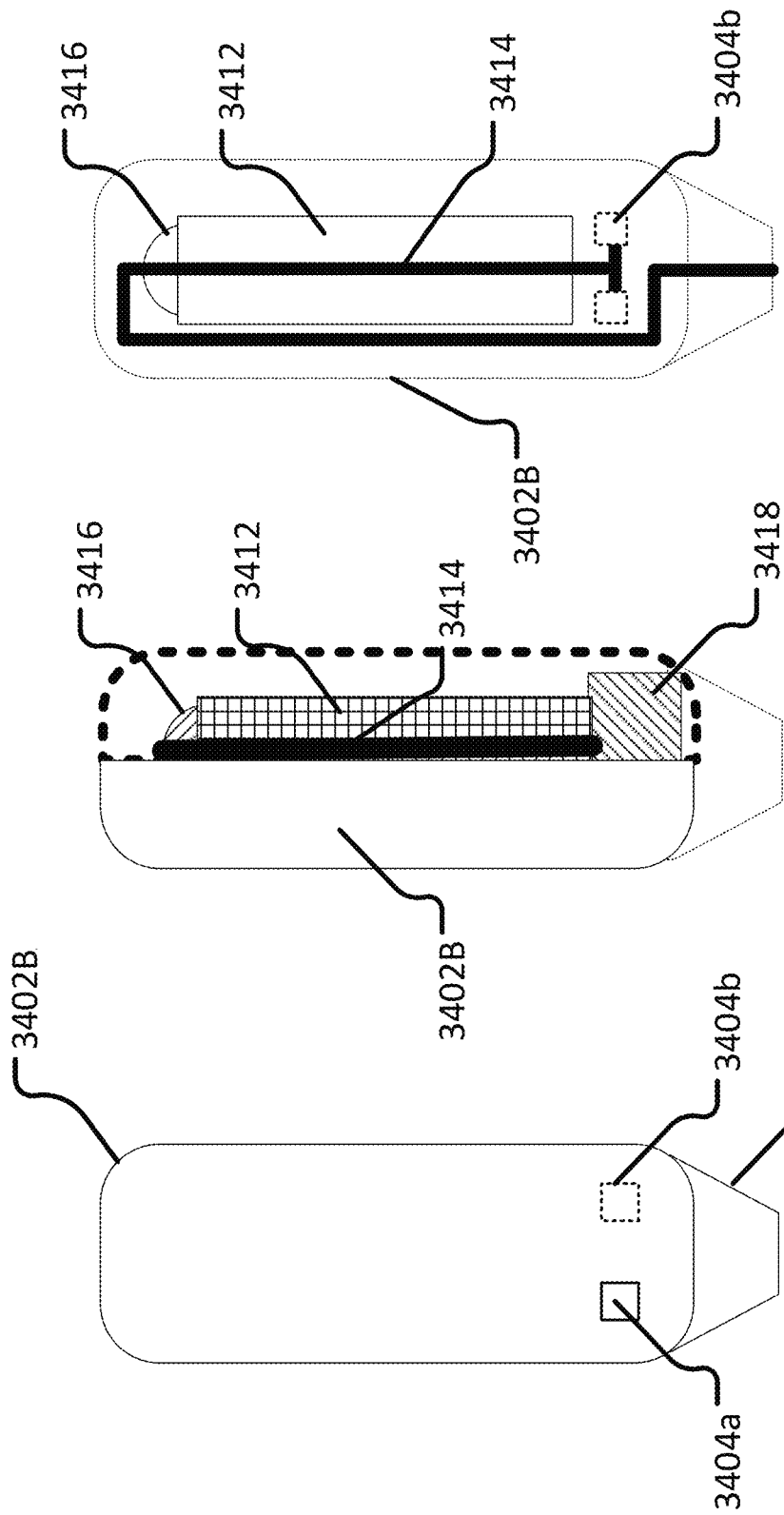

VAPORIZER APPARATUSES AND VAPORIZING METHODS

CROSS-REFERENCE TO RELATED APPLICATIONS

This application claims the benefit, under 35 U.S.C. § 120, of PCT International Patent Application No. PCT/US2019/049829 filed Sep. 5, 2019 and entitled "VAPORIZER APPARATUSES AND VAPORIZING METHODS," which claimed the benefit, under 35 U.S.C. § 119, of U.S. Provisional Patent Application No. 62/727,820 filed Sep. 6, 2018 and entitled "VAPORIZER APPARATUSES AND VAPORIZING METHODS." The entire content of each of these prior patent applications is incorporated herein by this reference.

BACKGROUND OF THE INVENTION

Field of the Invention

This invention relates to conditioning the air pre- and/or post a heat source of a vaporizer, but embodiments include non-vaporization techniques (e.g., combustion techniques such as dabbing, etc. . . . ) as well.

Description of the Background Art

The invention relates to conditioning air near or at the intake (e.g., upstream a heat source), near and/or at the mouthpiece (e.g., the most distal end of a vape pen), and/or at some location there between. More particularly, the invention relates to modifying air (e.g., increasing humidity and/or decreasing temperature) for a more pleasant "hit" or draw.

The invention also relates to alternative and complimentary solutions for improving the draw quality to avoid harsh, unpleasant inhalations that may cause coughing fits, among other unpleasantries.

Apparatuses such as vape pens and other portable vaporizer are a discreet delivery apparatus. Although such apparatuses offer considerable advantages over combustion-based techniques, extended draws expose the mouth and throat to hot, dry air, which can lead to harsher hits than well-constructed, hand-made cigarettes.

WO 2015/079198 discloses a pen vaporizer with a throw-away mention of a Peltier device used as the heating element. No details of how such a pen would be constructed are provided, and perhaps is a non-enabling disclosure.

U.S. Publication No. 2016/331024 discloses a vapor device with a cooling element that can be configured to cool vapor exiting the vaporizer prior to passing through an outlet (e.g., mouthpiece). The cooling element can cool vapor by utilizing air or space within the vapor device. The air used by the cooling element can exist in the vapor device or drawn into an intake and through the cooling element and the vapor device.

The intake can comprise various pumping, pressure, fan, or other intake systems for drawing air into the cooling element. In an aspect, the cooling element can reside separately or can be integrated the vaporizer. The cooling element can be a single cooled electronic element within a tube or space and/or the cooling element can be configured as a series of coils or as a grid like structure.

The materials for the cooling element can be metal, liquid, polymer, natural substance, synthetic substance, air, or any combination thereof. The cooling element can be powered by the power supply, by a separate battery (not shown), or other power source (not shown) including the use of excess heat energy created by the vaporizer being converted to energy used for cooling by virtue of a small turbine or pressure system to convert the energy. Heat differentials between the vaporizer and the cooling element can also be converted to energy utilizing commonly known geothermal energy principles.

U.S. Pat. No. 7,997,280 discloses a permeable sock (e.g., a wet cotton cloth) that moisture conditions the air post heat-source only or a combination of both pre- and post-heat source air of a glass-tube vaporizer that uses a lighter as the heat source.

US20130276799 discloses cooling vapors (i.e., post heating element) with room air or a heat pump, such as a Peltier element.

WO2016172802 is directed to a vape-cartridge construction, including extending the airpath at the mouthpiece. The cartridge may include memory that is in communication with vape heat control circuitry.

US20180104214 discloses heating a material containing a compound to a first temperature to form a heated volume of the material and additionally include heating the heated volume to a higher second temperature to form a dose of vapor including the compound. The method may further include pre-heating the material to a preliminary temperature prior to the heating to the first temperature.

There remains a need for further refinement of the above ideas. For example, the above solutions will not work on existing vaporizers and require a proprietary hardware or configuration.

SUMMARY OF THE INVENTION

It is therefore an object of the invention to provide the apparatus and methods of the appended claims.

Further scope of the applicability of the present invention will become apparent from the detailed description given hereinafter. However, it should be understood that the detailed description and specific examples, while indicating preferred embodiments of the invention, are given by way of illustration only, since various changes, combinations and modifications within the scope of the invention, as defined in the claims, will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIGS. 5A to 5G show a portable vaporizer device according to one or more aspects of the present invention;

FIGS. 16A to 16D show a portable vaporizer device according to one or more aspects of the present invention;

FIGS. 20A to 20C show a portable vaporizer device according to one or more aspects of the present invention;

FIGS. 21A and 21B show a portable vaporizer device according to one or more aspects of the present invention;

FIGS. 31A to E show various low-frequency periodic signals/waveforms according to one or more aspects of the present invention;

FIGS. 34A to 34D shows a vaporizer device according to one or more aspects of the present invention;

DETAILED DESCRIPTION OF THE DRAWINGS

As used herein, "portable vaporizer device" may refer to, individually or collectively, to one or more vaporizer devices such as (1) a battery or battery section (e.g., vape pen batteries, portable herb-based vaporizers, among other possible types), (2) a cartridge adapted or adaptable to mechanically and electrically couple with a body (e.g., a battery section) that is adapted to provide electrical power for heating a volatizable material (e.g., plant material or an extract thereof), (3) a sleeve, as detailed below, and (4) adaptors, as also detailed below, that interface, for example, a cartridge or heater with a battery section, including electrically and/or mechanically coupling to both the battery section and cartridge/heater and expanding on (or improving) a portable vaporizer device's functionality. Multiple portable vaporizer devices that are operably coupled to each other may be referred to, as a whole, as a portable vaporizer device or portable vaporizer system.

As used herein, "proximal" generally refers to the side or section of a device closest to a mouthpiece (e.g., a mouthpiece or "mouthpiece side") and "distal" refers to a side or section furthest away from the mouthpiece/mouthpiece side.

Figure 8A:
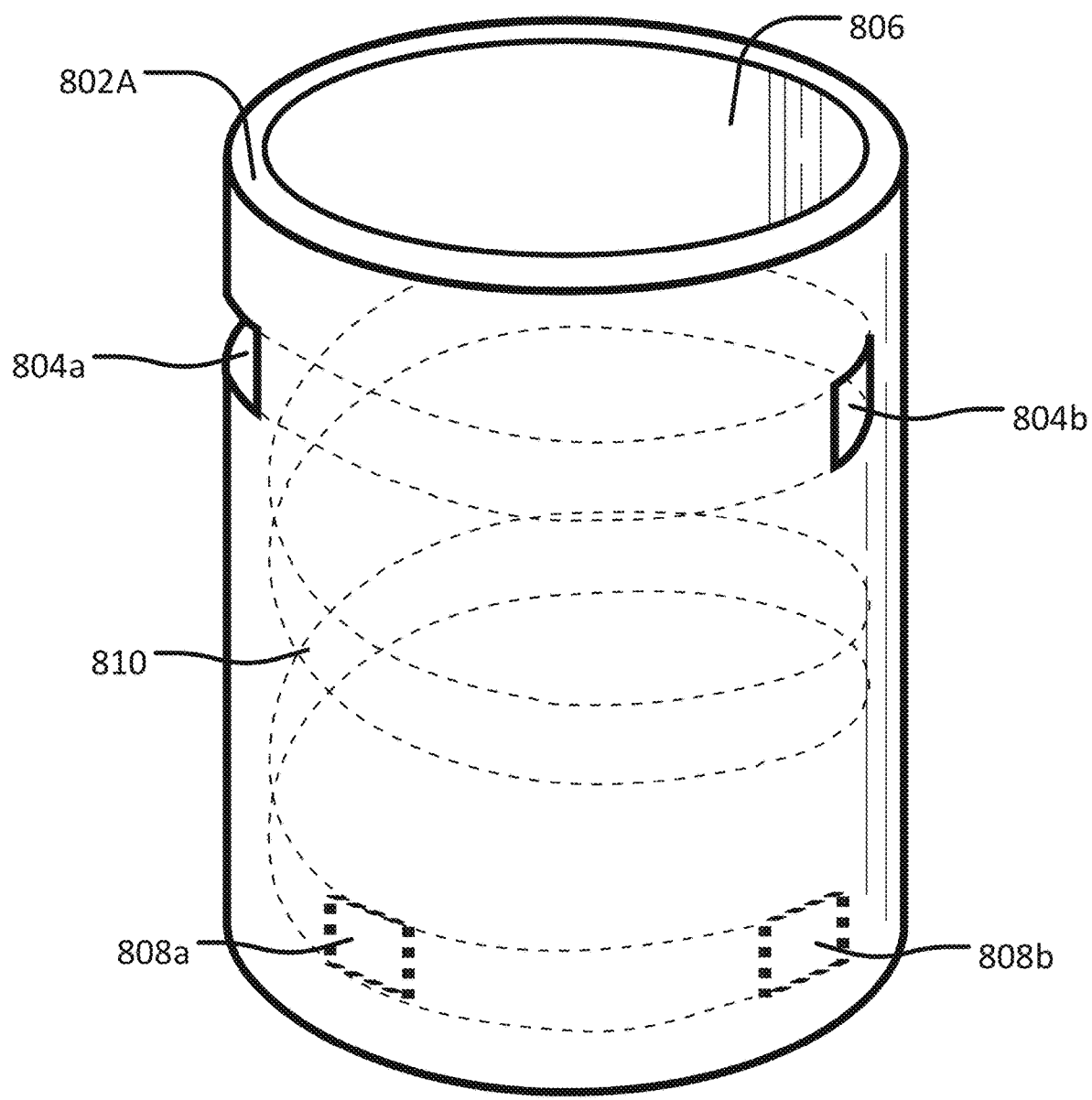
FIGS. 8A to 8D show a portable vaporizer device according to one or more aspects of the present invention.

In schematic drawings, dashed or dotted lines typical show optional features for a device, but in the case of FIG. 8A, for example, the dashed lines designate features that are internal or otherwise not seen at that particular view.

As used herein, an "adapter" is a device that electrically interfaces a cartridge with a battery section. A sleeve, which may or may not be an adapter, modifies the temperature and/or moisture level of "intake air", or air that is drawn through the sleeve, which may take place downstream or upstream of a vaporizer device's heater.

Portable vaporizer system 100 includes, inter alia, cartridge 102, air intake feature(s) 104, and connector 106, which is embodied as an outer threading. The battery section's 108 co-axial inner threading (a connector that is not shown) is coupled to the cartridge's 102 threading 122. System 100 further includes battery section 108, mouthpiece 110, post-heater airpath 112, user-input button 114, globe mouthpiece 116, and heater adapter 118. Cartridge 102 defines airpath 112, which is upstream of both the heater and air intake feature 104 and downstream mouthpiece 110.

For non-cartridge uses (e.g., user-supplied extracts), heater adapter 118 mechanically couples with outer threading 106. A volatizable material (e.g., an extract) is placed on the top "cup" of heater adapter 118, which is thermally adapted to a heating element (not shown) of adapter 118. Via O-rings 118a, heater adapter also couples with globe mouthpiece 116.

Figure 18A:
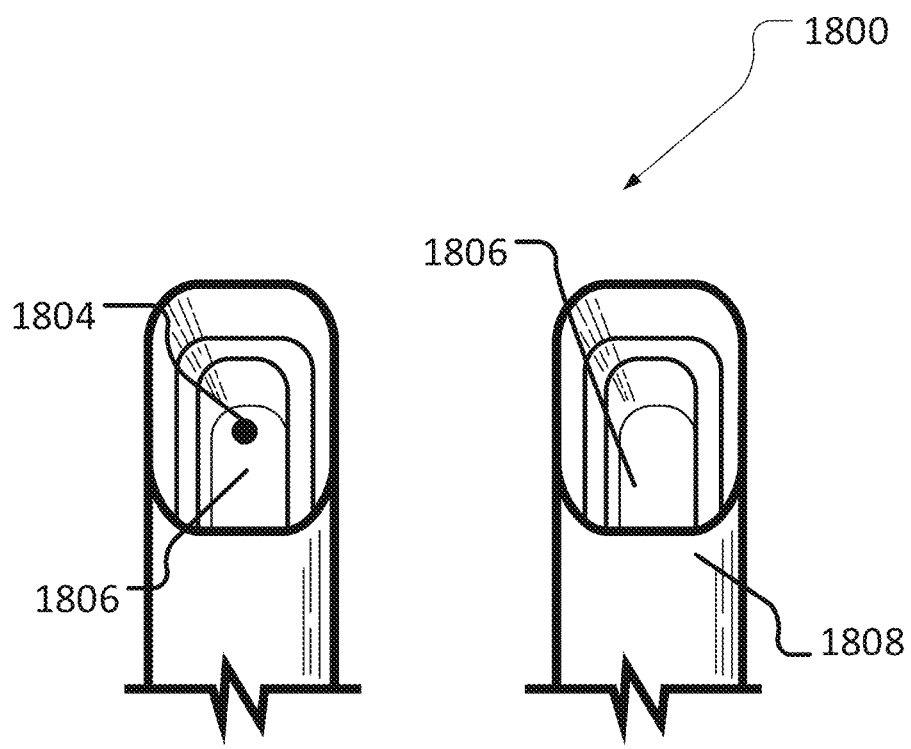
FIGS. 18A and 18B show a prior art portable vaporizer device.
Figure 18B:
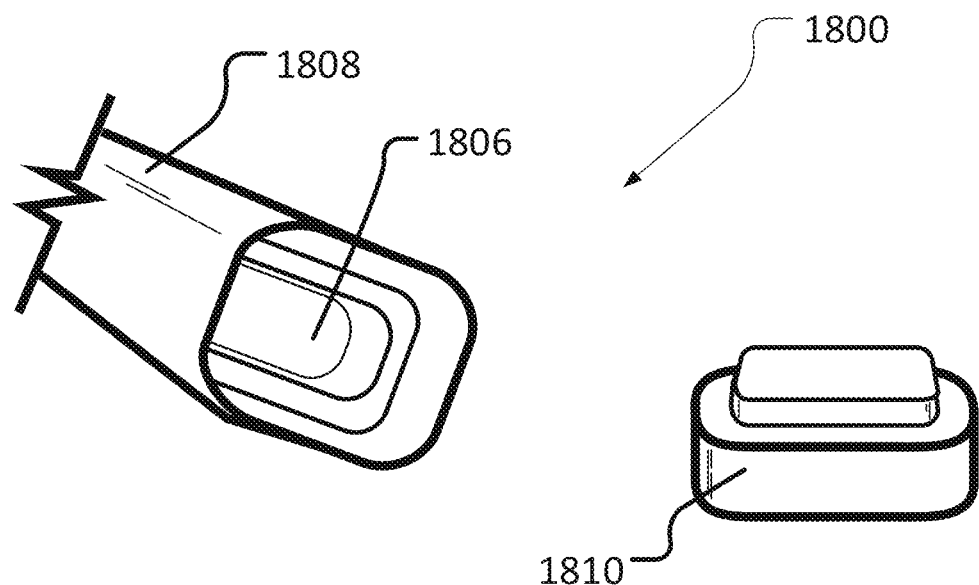

The various innovative aspects described herein overcome one or more shortcomings of the state-of-the-art system shown in FIGS. 1A to 1D. For example, the prior art doesn't contemplate modifying a temperature level and/or moisture content of air upstream of a heating element such as a cartridge's heater or oven (an oven defines a cavity for receiving a volatizable material, as shown in FIGS. 18A and 18B). Such a cavity may directly house a volatizable material or interface with a "pod" or other reservoir or container that houses the volatizable material. "Pod" style reservoirs are placed directly in a heater and may operate somewhat like "coffee pods". Indeed, it has been shown that such systems can extract components from cannabis.

An inventive insight is that said modification is done upstream of said heating element or oven, increasing the intake air's moisture content still leads to "smoother" or "less harsh" draws. In contrast, almost the entirety of the state of the art is focused on modifying air downstream of said heating element or oven.

Another innovative aspect is improving the ubiquitous portable vape (e.g., a vape pen) adapted to vape various oils that are either supplied by a user or are contained within a cartridge. Cartridges include a heating element (e.g., a resistive heater) for heating the oil drawn from the cartridge reservoir. The heater is powered by the battery section of the portable vape. Due to the lack of a temperature sensor and the variation of physical and operational parameters of the portable vape and cartridge, it's easy to produce an unpleasantly harsh draw that may lead to extended coughing.

Typical vape pens and similarly sized vaporizers allow a user to only select a voltage level that is applied to a heater of the cartridge or other heating element. Another departing innovation is providing a user-selected low-frequency value, which in some embodiments may be independent of voltage and/or temperature, that serves as a "master duty cycle" with variable periods of an OFF or otherwise muted heating element drive signal that lasts at least around a 0.5 second. Various high-frequency duty cycle techniques exits for precise temperature or dosage control, but the prior art does not contemplate a user-specified temporal value that periodically "mutes" or attenuates the heating element drive signal, among others, for a user-specified time (e.g., a half second to one or more seconds) when a user is drawing (e.g., when a draw sensor sense a draw) or the user pushes an activation button like button 114.

Such techniques have several advantages. For example, a portable vaporizer may be simplified by providing a single voltage with a user-defined, low frequency (e.g., 120 Hz or lower) duty cycle. This is particularly advantageous for cheap, portable vapes that do not have a temperature sensor or similar "monitoring" circuitry. However, the "master duty cycle" can be combined with a high-frequency duty cycle (e.g., 1 kHz or higher) for sophisticated temperature control based on temperature sensor input. For example, during "OFF periods" of the master duty cycle, no or a reduced power may be applied to a heater, but during "ON periods", power is applied in a steady state manner and/or according to a high-frequency duty cycle for accurate temperature control (e.g., rapid toggling between ON and OFF states according to the high-frequency duty cycle during the (lower-frequency) master duty cycle "ON periods").

More generally, a portable vaporizer device may be operable in a "pulsed mode", wherein the heater is toggled on or off, among other low-frequency "modulations", according to a master duty cycle or other low-frequency modulation. Other low-frequency control measures include varying a variable resistor that is arranged (electrically) between a heating element and battery. In such embodiment, a rate and/or range of the resistor values may be user selectable. Embodiment rates (e.g., control signal periods) may range from around a second or longer. Embodiment ranges may include 10 to 50, 1 to 100, and 0.50 to 50, among other possible ranges.

More generally, a controller may be operable to control a low-frequency, periodic application of power from a power source to a heater of a personal vaporizer. This "periodic application" may be binary, such as the case in duty cycles or "jumping" from two, non-zero voltage values (e.g., a square wave), or may follow other low-frequency waveform patterns (e.g., triangle, curved, half-circle, half-oval, half-hexagon, etc.) as seen in FIGS. 31A to E.

Another departing innovation is that although different, user-selected discrete voltages can be supplied by a battery section, an innovative insight is that the selected voltages can be further "fine-tuned" by a user-selected (or user influenced) variable resistance value of a variable resistor (e.g., a potentiometer or PIN diode) that is provided between the battery and a heating element.

The user-selectable variable resistance value (e.g., a 5 to 100 variation range) has several embodiments, including the incorporation of a resistor or other resistive element along the threading of either or both the threaded portions of a cartridge (e.g., the male end) or battery section, which typically houses a female section. The two threaded portions establish an electrical coupling between the heating element(s) (of the cartridge) and the battery. In this embodiment, the user may decrease or increase the resistance by simply turning the male end of the cartridge further in or out of the female section.

Other examples include a potentiometer or other variable resistant element residing on the battery section or cartridge or an interfacing piece thereof (e.g., a sleeve or an adapter).

In another embodiment, the modification sleeves can be modular. For example, the sub-sleeves can be stacked to condition the intake air. One sub-sleeve could be for temperature, while another sub-sleeve can moisture condition the intake air.

Another departing innovation is utilizing a thermoelectric element in various novel configurations for a personal (e.g., portable, hand-held, "table-top") vaporizer.

Figure 1A:
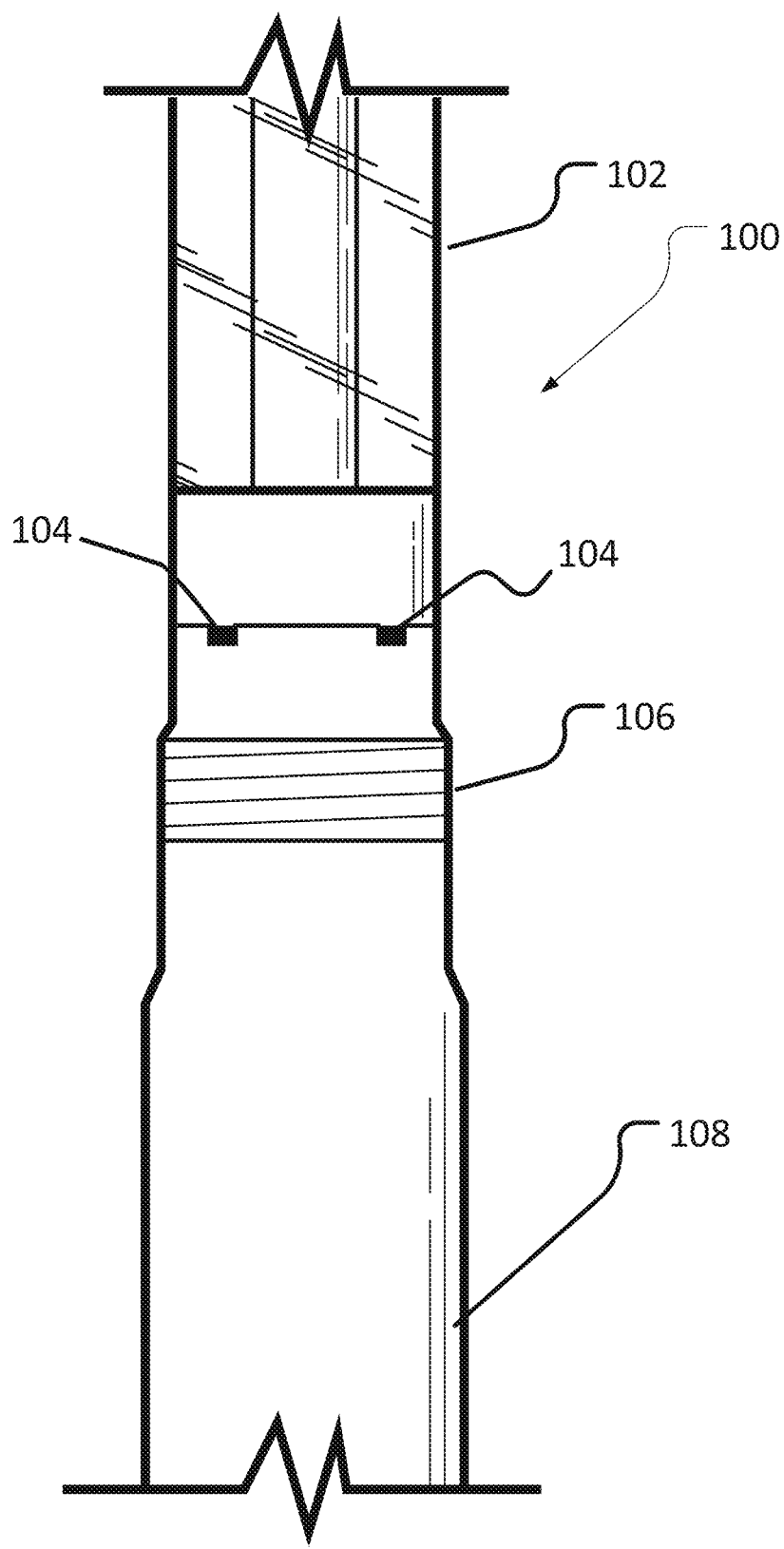
FIGS. 1A to 1D show a prior art portable vaporizer system.
Figure 1B:
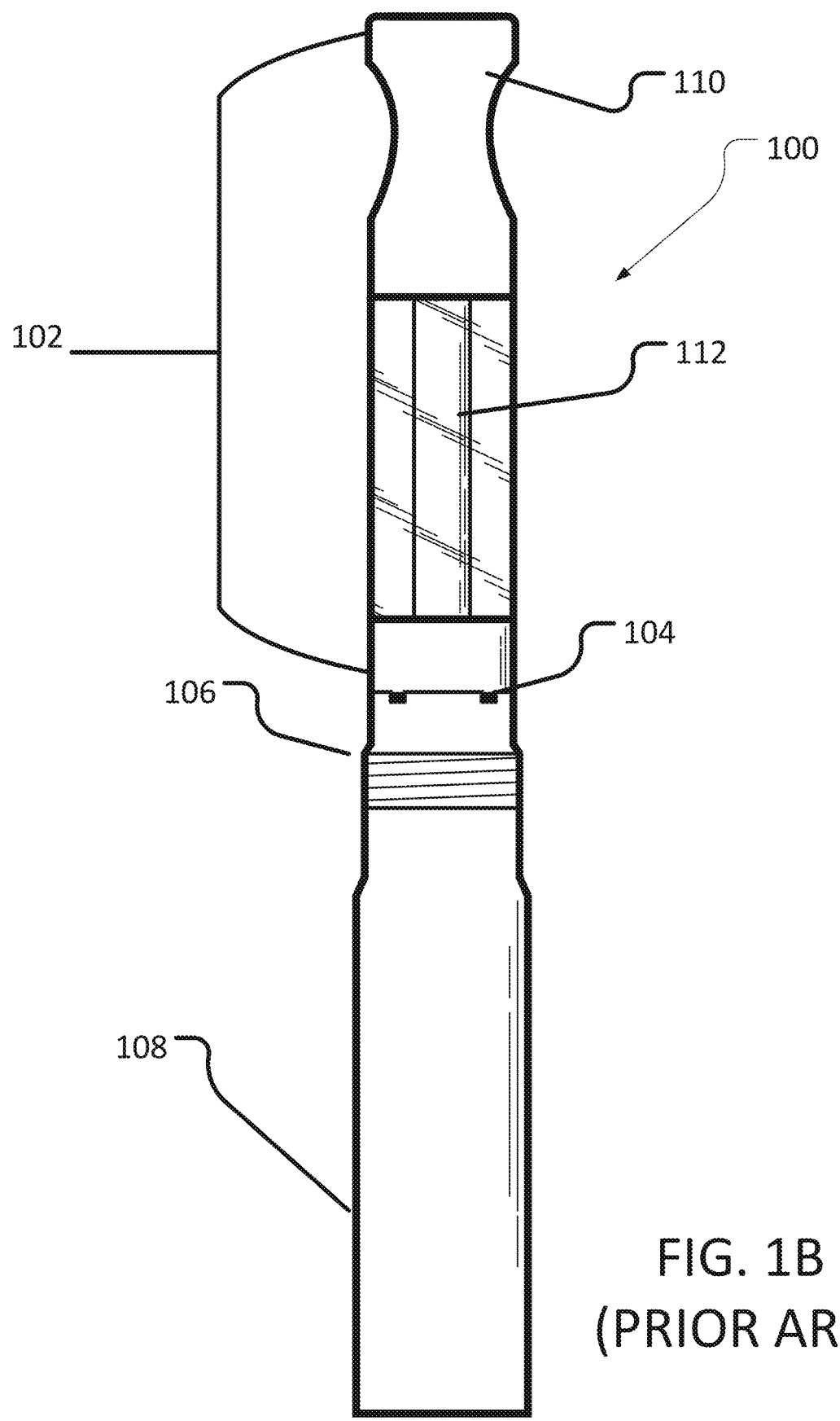
Figure 1C:
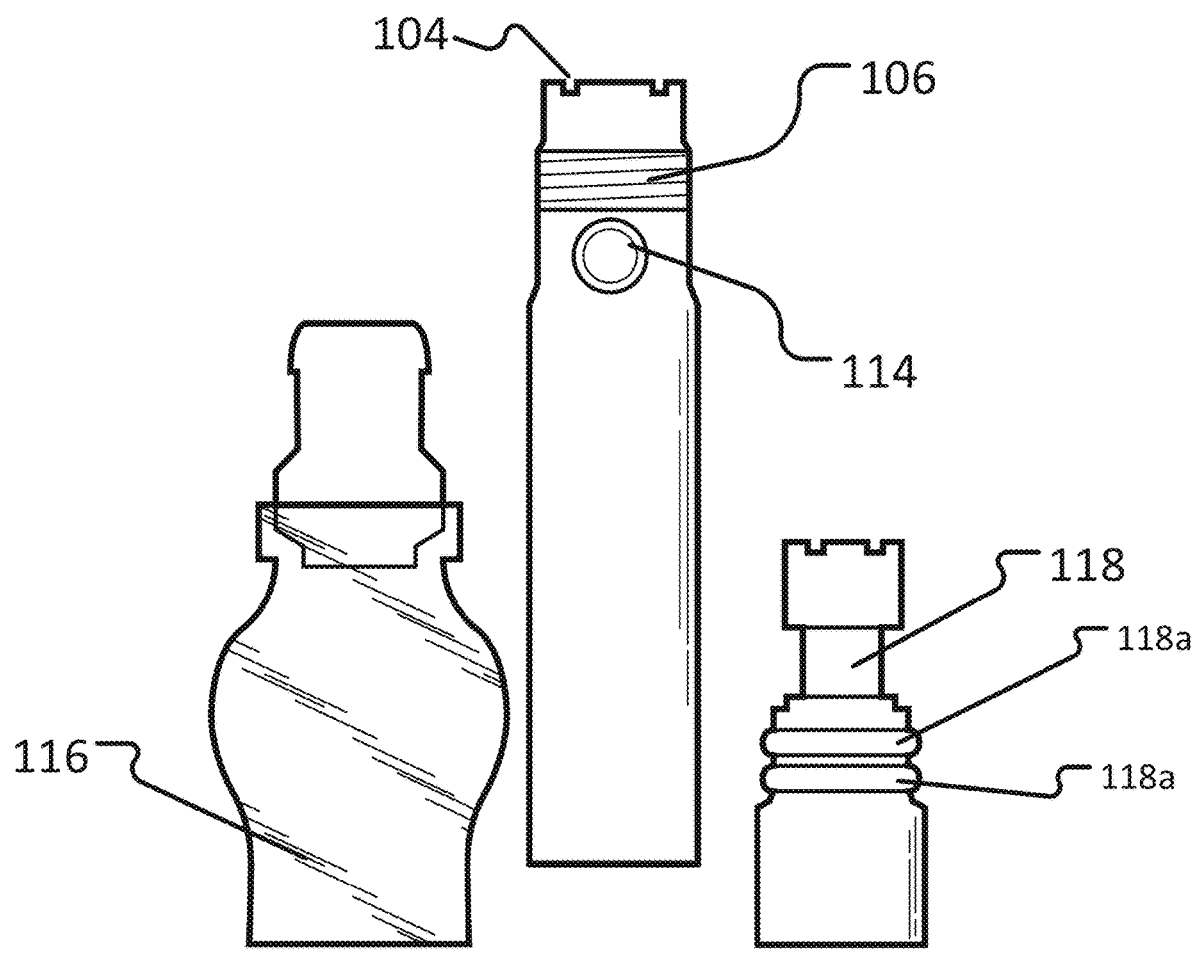
Figure 1D:
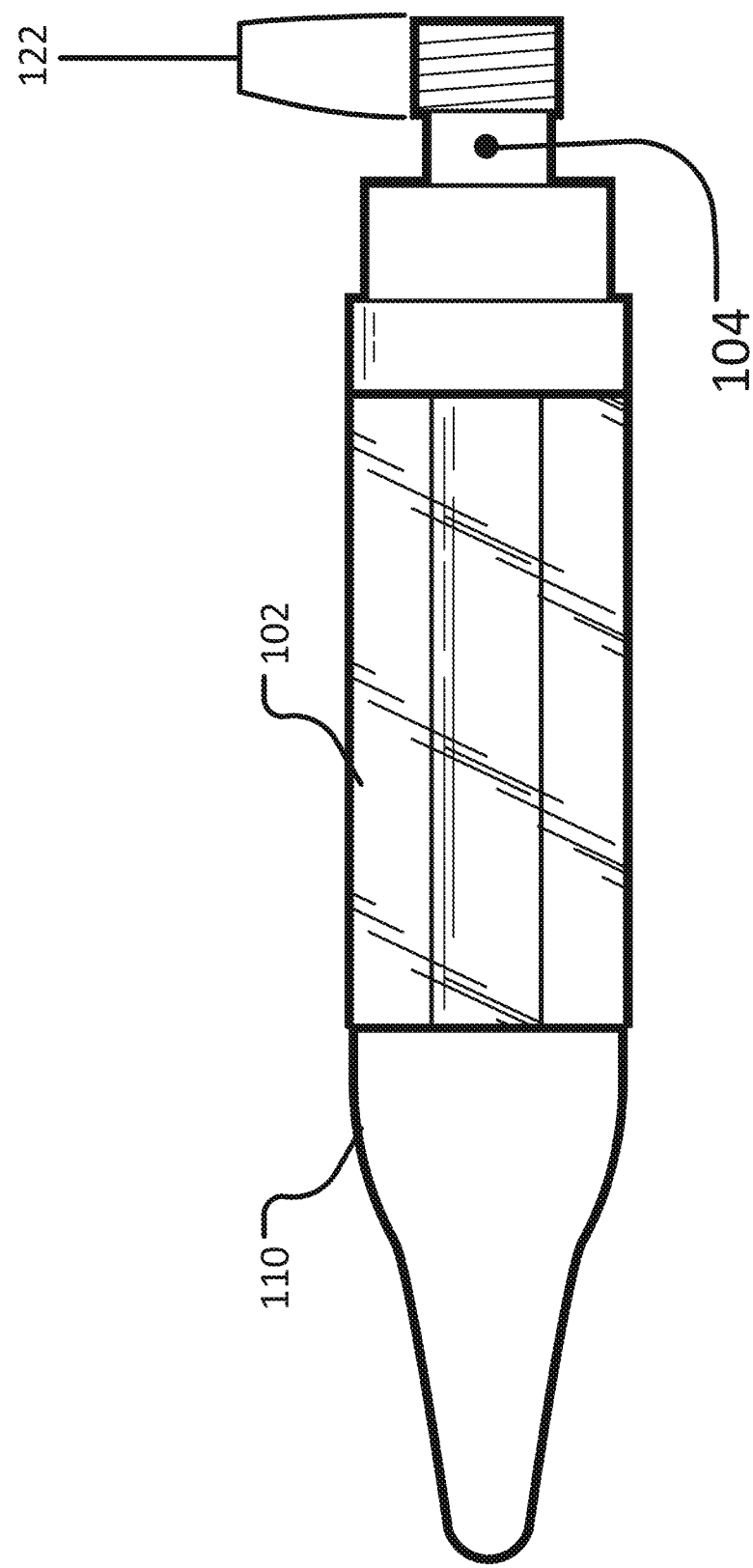
Figure 2:
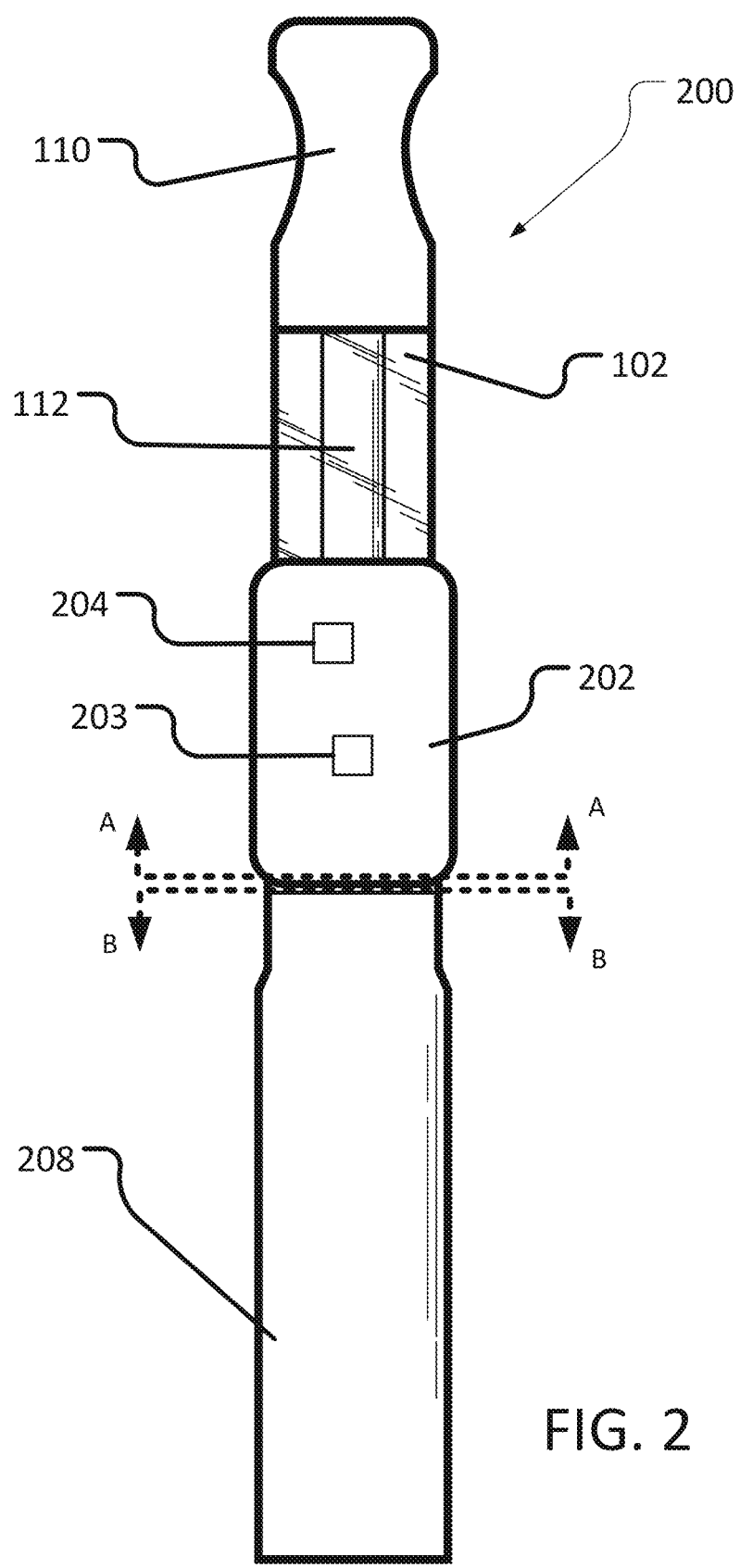
FIG. 2 shows a portable vaporizer device according to one or more aspects of the present invention.

FIG. 2 shows portable vaporizer device 200, which, like system 100, also includes, cartridge 102, battery section 208, mouthpiece 110, and airpath 112. In addition, device 200 includes sleeve 202. Sleeve 202 includes air modification element (AME) 203 arranged in fluid communication with (the airpath defined by) cartridge 102 and air intake feature 204. The AME 203 is adapted to modify at least one of a temperature and/or moisture content of air that is passing through (or along) sleeve 202. Sleeve 202 may define a cylindrical shape (internally) for accepting and at least partially surrounding cartridge 102. Modifications include heating air, cooling air, increasing moisture content of air (humidifying), and decreasing moisture content of air (dehumidifying).

The AME 203 may actively or passively modify air temperature or moisture level of the intake air. Active embodiments include, for example, Peltier devices, which are also known as thermoelectric devices, and humidifier transducer, such as Piezo ultrasonic atomizers operably connected to a water source. Passive embodiments include phase change materials (e.g., water, paraffin, refrigerant gels) housed within sleeve 202 and typically used to lower or maintain the temperature of thermally coupled "in-take" air.

For cooling embodiments, sleeve 202 may be called a "cool sleeve". For example, air may flow pass a cooling AME 203 before reaching a user's mouth.

Sleeve 202 defines an airpath channel (not shown) that would be in fluid communication with air intake feature 204, where said air intake feature 204 is upstream of the heater (not shown) of cartridge 102. In other words, when a user takes a draw from mouthpiece 110, air is drawn through air intake feature 204 and then past (or through) AME 203 and cartridge 102 before reaching the user's mouth. Said air is typically carrying, downstream the heater, an aerosol containing an active ingredient (e.g., atomization of the material/substance contained in cartridge 102).

Sleeve 202 may couple to battery section 208 in a variety of ways (e.g., as shown in FIGS. 6A-B and 7A-B). In some embodiments, sleeve 202 defines a threading that couples with threading such as outer threading 106 shown in FIGS. 1A to 1C. In some embodiments, sleeve 202 and/or battery section 208 may have magnets and/or ferrous metals or similar materials arranged such that sleeve 202 magnetically couples to battery section 208. In some embodiments, sleeve 202 and battery section 208 are electrically coupled via wired or wireless means.

Figure 3A:
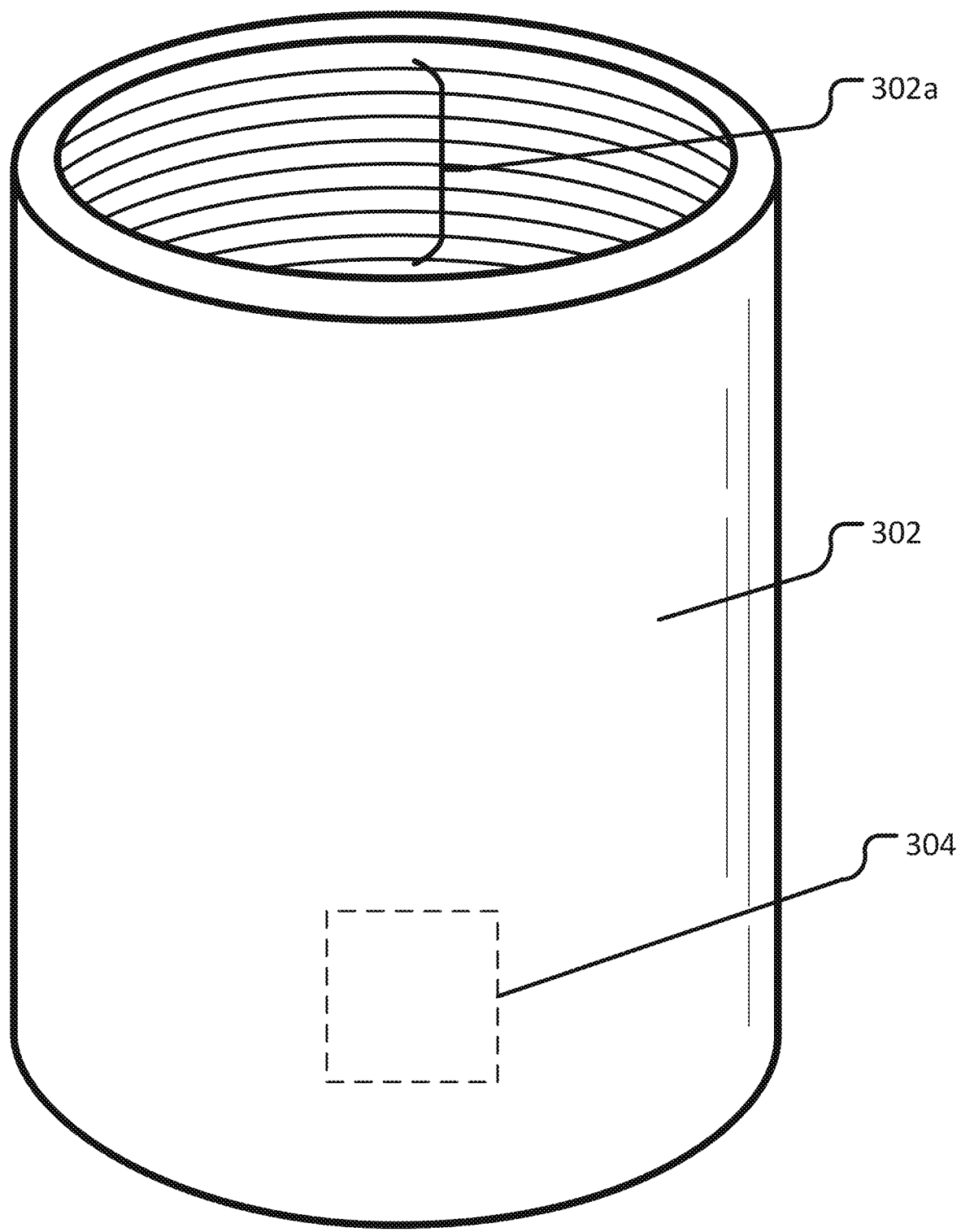
FIGS. 3A to 3E show a portable vaporizer device according to one or more aspects of the present invention.
Figure 3B:
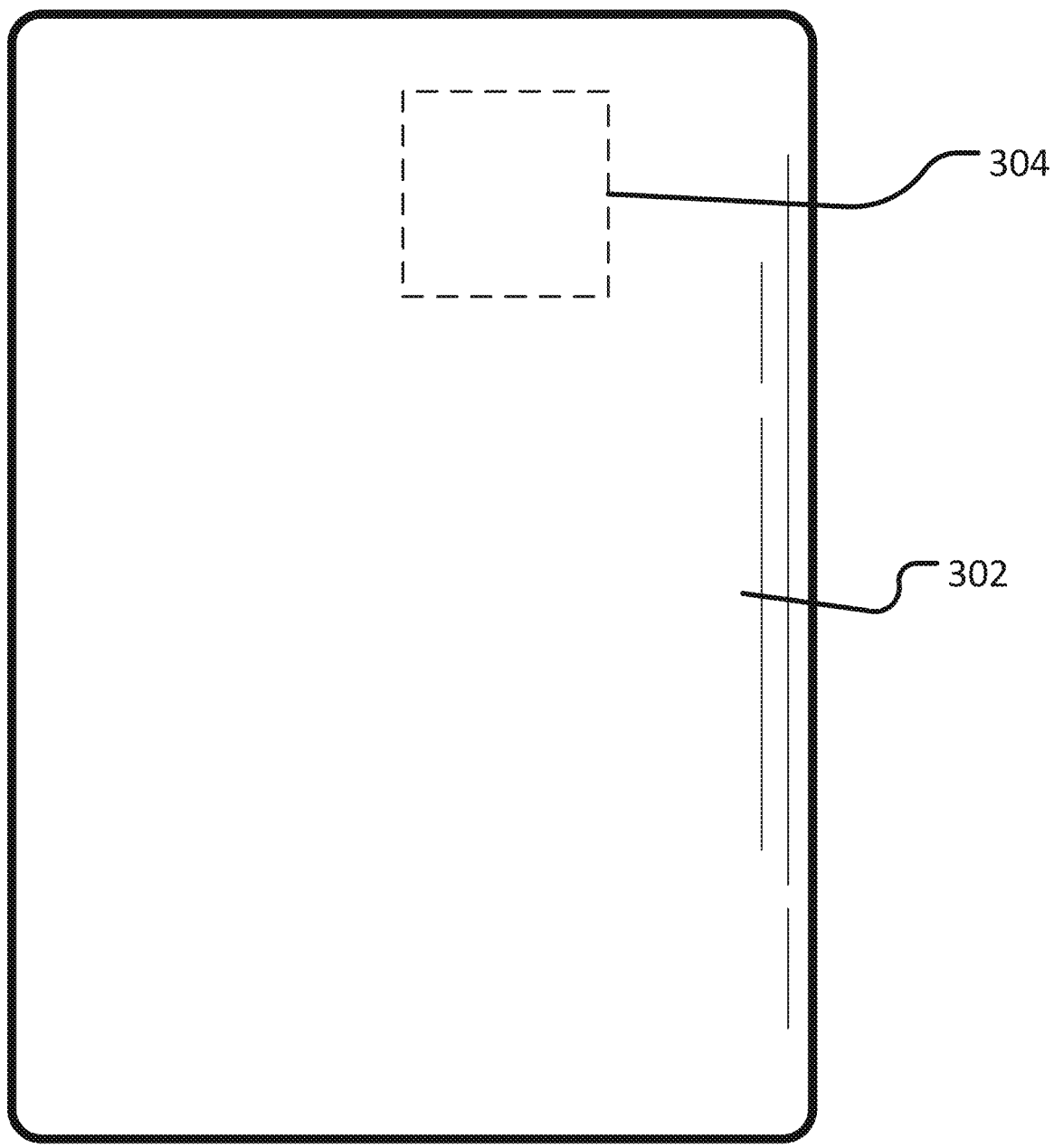
Figure 3C:
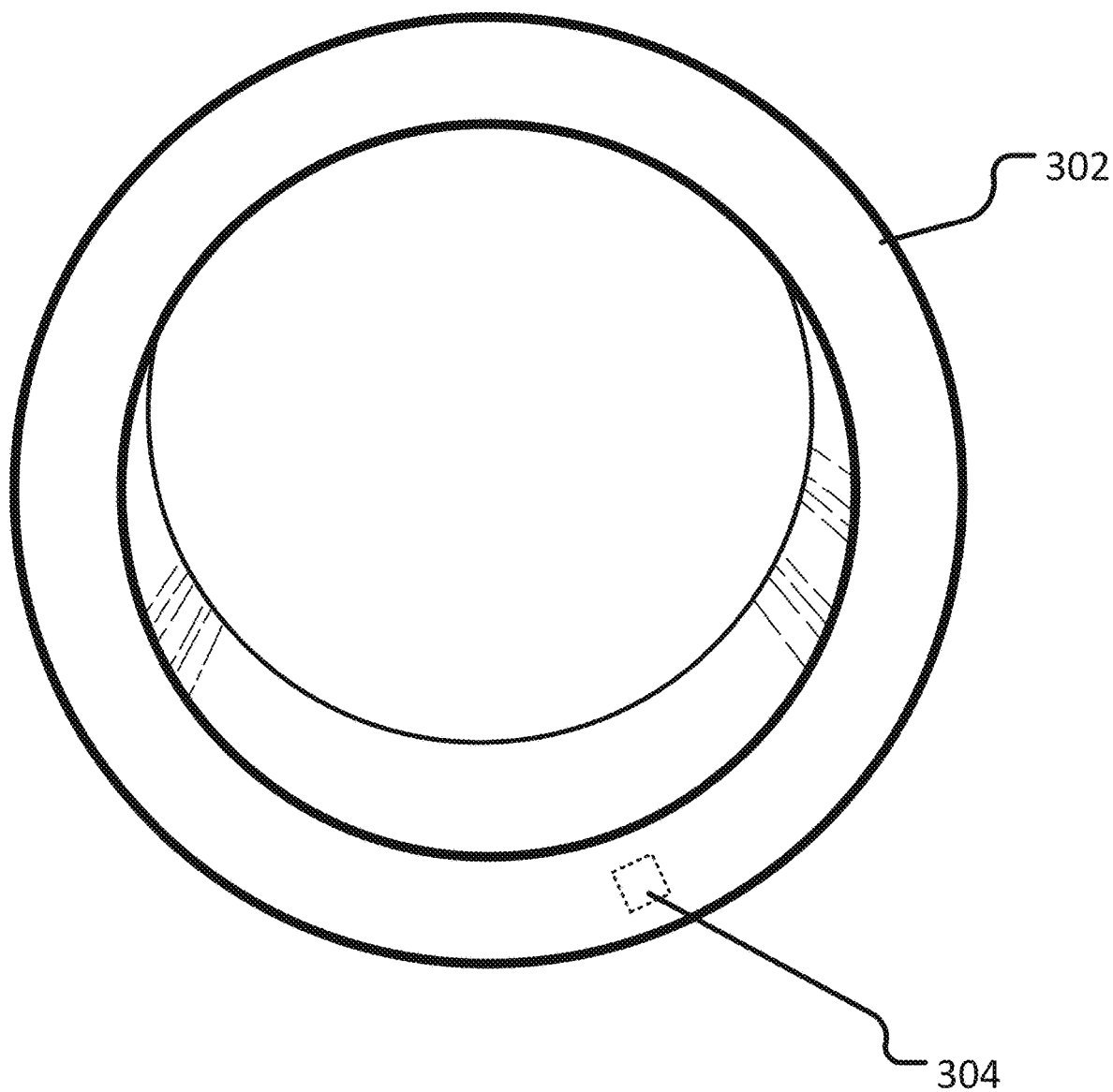
Figure 3D:
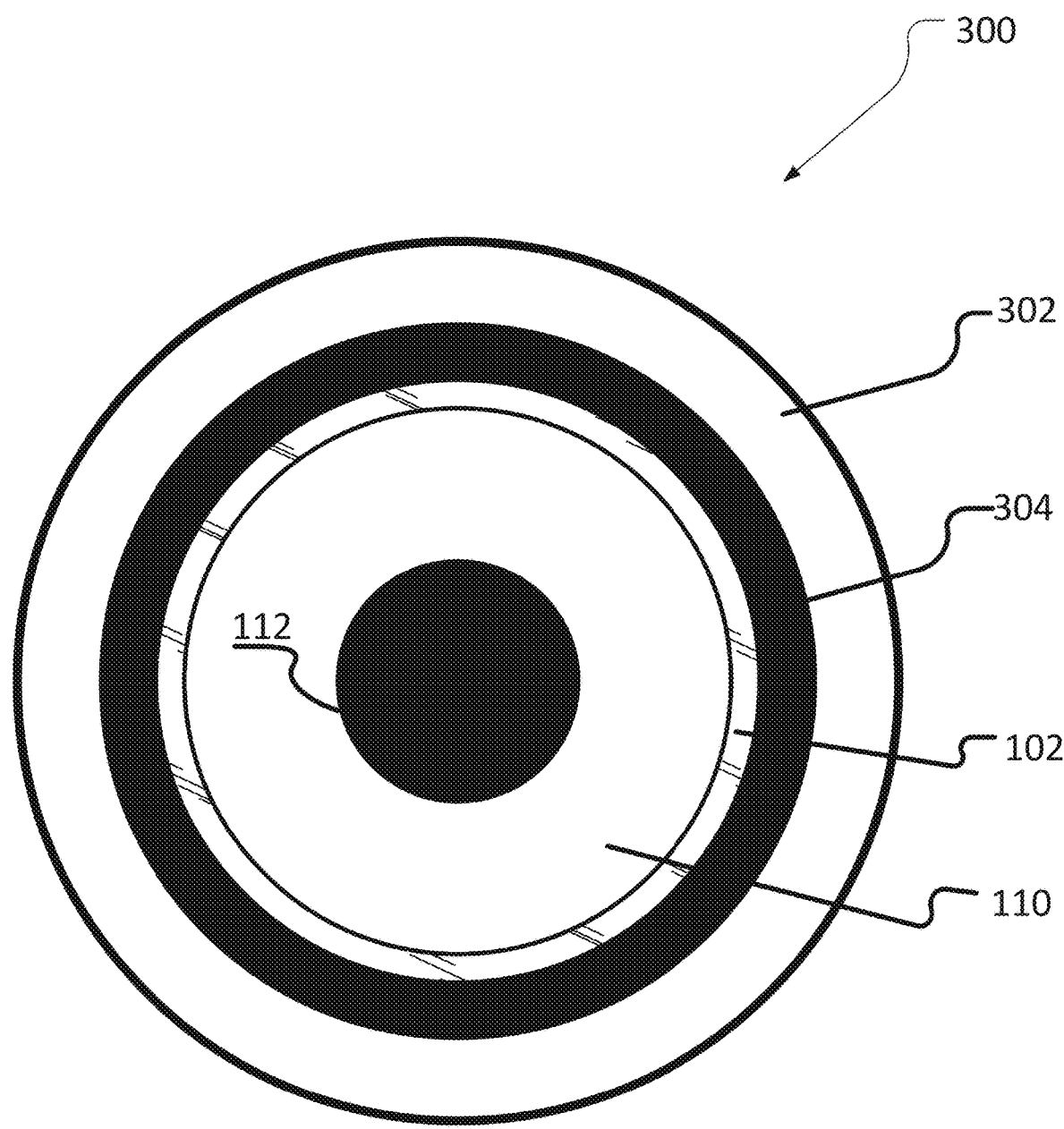
Figure 3E:
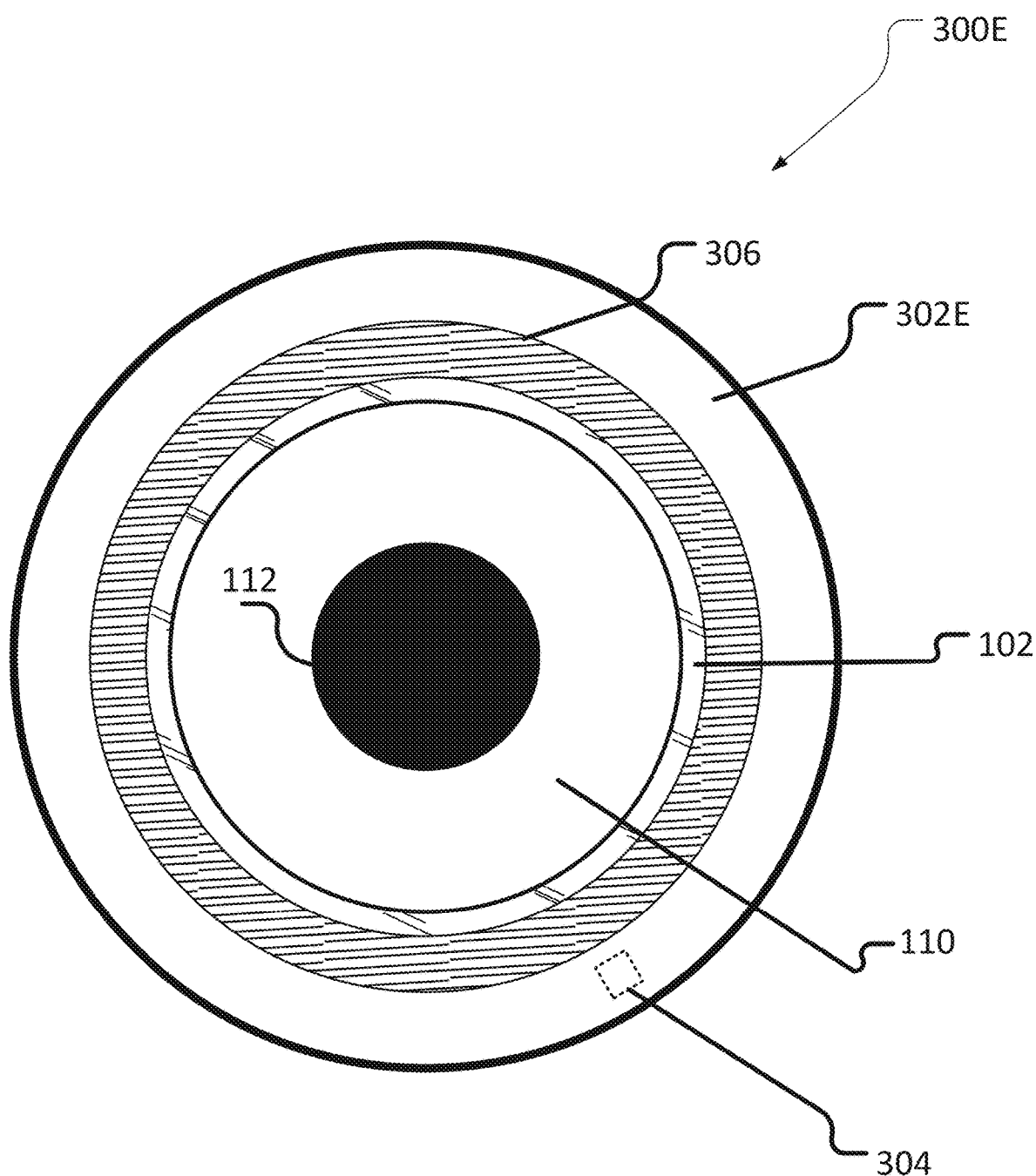

FIGS. 3A to 3E show embodiments of sleeve 302. FIGS. 3A to 3C show sleeve 302 at different views and FIGS. 3D and 3E, are alternative top views of device 300, also show cartridge 102, mouthpiece 110, and air path 112. Sleeve 302 includes connector 302a, which is dimensioned and adapted to couple with a threaded connector such as connector 106 shown in FIG. 1.

In some embodiments, sleeve 302 defines a hollow cylinder with an aperture sufficiently dimensioned to accommodate cartridge 102. Aperture widths or diameters tend to vary from around 0.410 to 0.420 an inch, depending on the cartridge width (e.g., a cylindrical cartridge's diameter).

In some embodiments, as shown in FIG. 3E, device 300E includes O-ring 306 that mechanically interfaces cartridge 102 and sleeve 302E. O-ring 306 may establish a sufficient seal (e.g., air tight/hermetic seal, semi-hermetic or similar seal) such that air is "forced to be" drawn (as a user takes a draw from mouthpiece 110) into one or more air intake features 304 of sleeve 302/302E and through sleeve 302/302E before reaching a heater of cartridge 102.

However the seal or semi seal is established (e.g., O-ring(s), elastomer grommets, etc. . . . ), mouthpiece 110 is in fluid communication with at least one air intake feature (304) of sleeve 302, 302E when cartridge 102 is coupled to, for example, battery section 108, 208, 408 or similar section.

As another example and shown in the embodiment of FIG. 3D, air intake feature 304 is defined by both cartridge 102 and sleeve 302. That is, air intake feature 304 is defined by the space between the inner surface of sleeve 302 and the outer surface of cartridge 102. Sleeve 302 may be cooler or hotter than ambient temperature and thereby modify air as it passes by a surface of sleeve 302.

Figure 4:
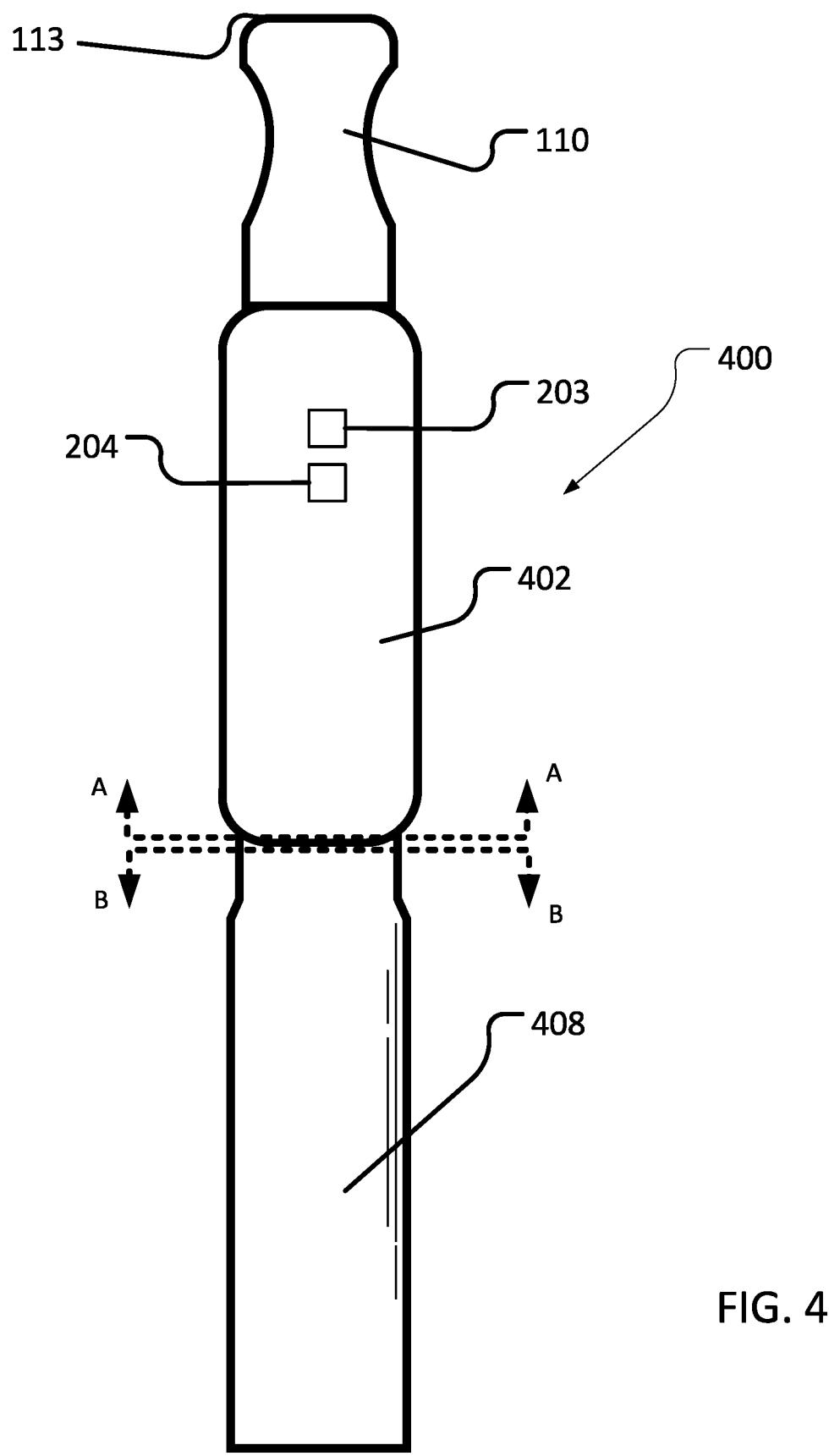
FIG. 4 shows a portable vaporizer device according to one or more aspects of the present invention.

Device 400 includes sleeve 402, which extends further along the length of cartridge 102, compared to sleeve 302. Sleeve 502 of device 500 is dimensioned to totally encapsulate cartridge 102. In such embodiments, mouthpiece 502a may interface with mouthpiece 110 of cartridge 102 and extend the airpath from the proximal end 113 of mouthpiece 110 (FIG. 4) to an outlet end 503 of mouthpiece 502a.

Figure 5A:
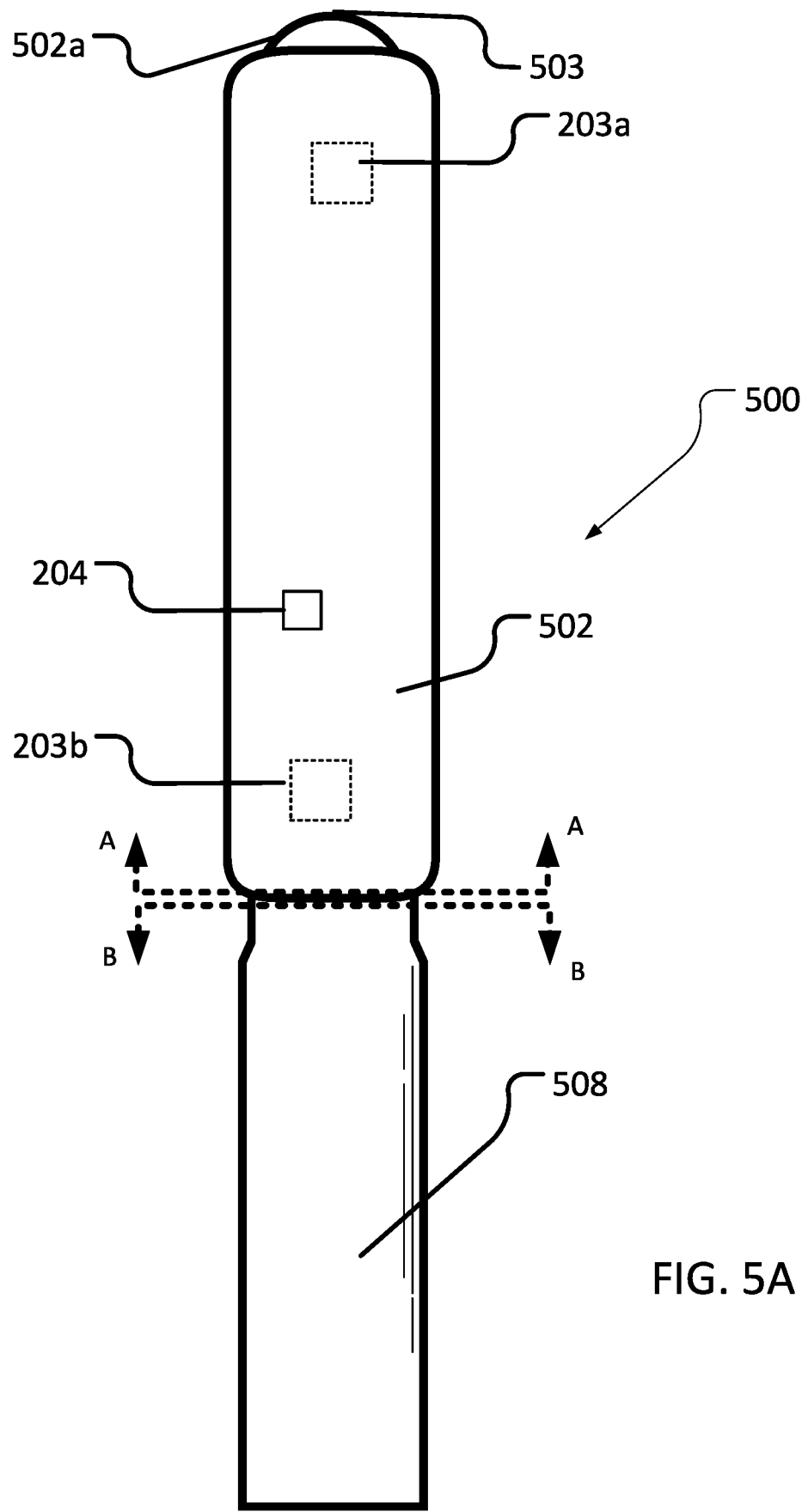
Figure 5D:
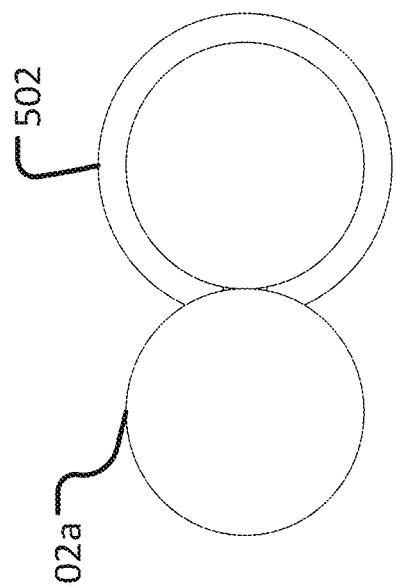
Figure 5C:
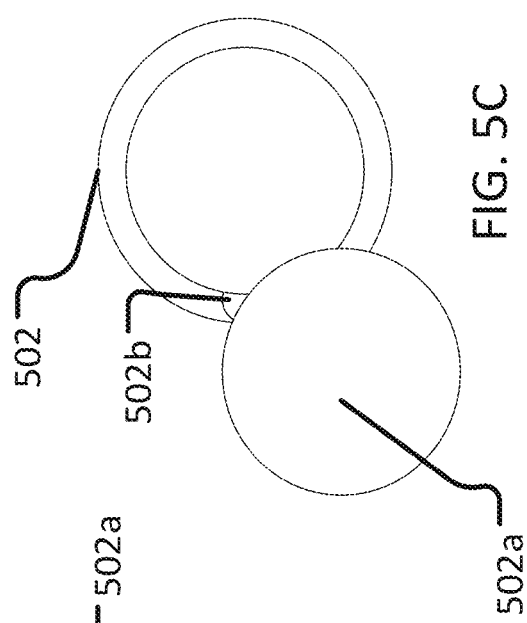
Figure 5B:
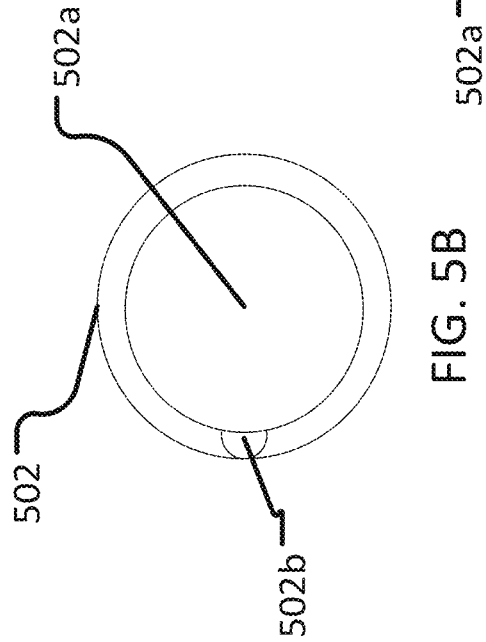

Mouthpiece 502a may move relative to sleeve 502 for allowing a cartridge 102 to pass through and make an electrical connection with at least one of device 500 or battery 508. For example, mouthpiece 502a may be connected via a hinge that allows mouthpiece 502a to rotate about an axis parallel (e.g., FIGS. 5B to 5D) or orthogonal (e.g., FIGS. 5E to 5G) to a notational axis spanning the length (from the battery section side to the mouthpiece side) of sleeve 502.

In alternative embodiments, mouthpiece 502a may be attached by threaded, magnetic, or other physical coupling techniques. In such embodiments, mouthpiece 502a may be completely removable and readily swappable with other mouthpieces.

In some embodiments, a sleeve (e.g., sleeve 300, 400, and 500) may electrically couple with both a battery section (e.g., 308, 408, 508) and a cartridge. In some embodiments, a sleeve may only electrically couple to a battery section and thus establish two electrical connections/loads (e.g., loads in series, in parallel, or on separate circuits) powered by a battery section.

In some embodiments, a sleeve may be active and contain a battery or other power source. In some embodiments, a sleeve and battery section are adapted to selectively switch from a sleeve's power source/battery to a battery section's power source.

Figure 9:
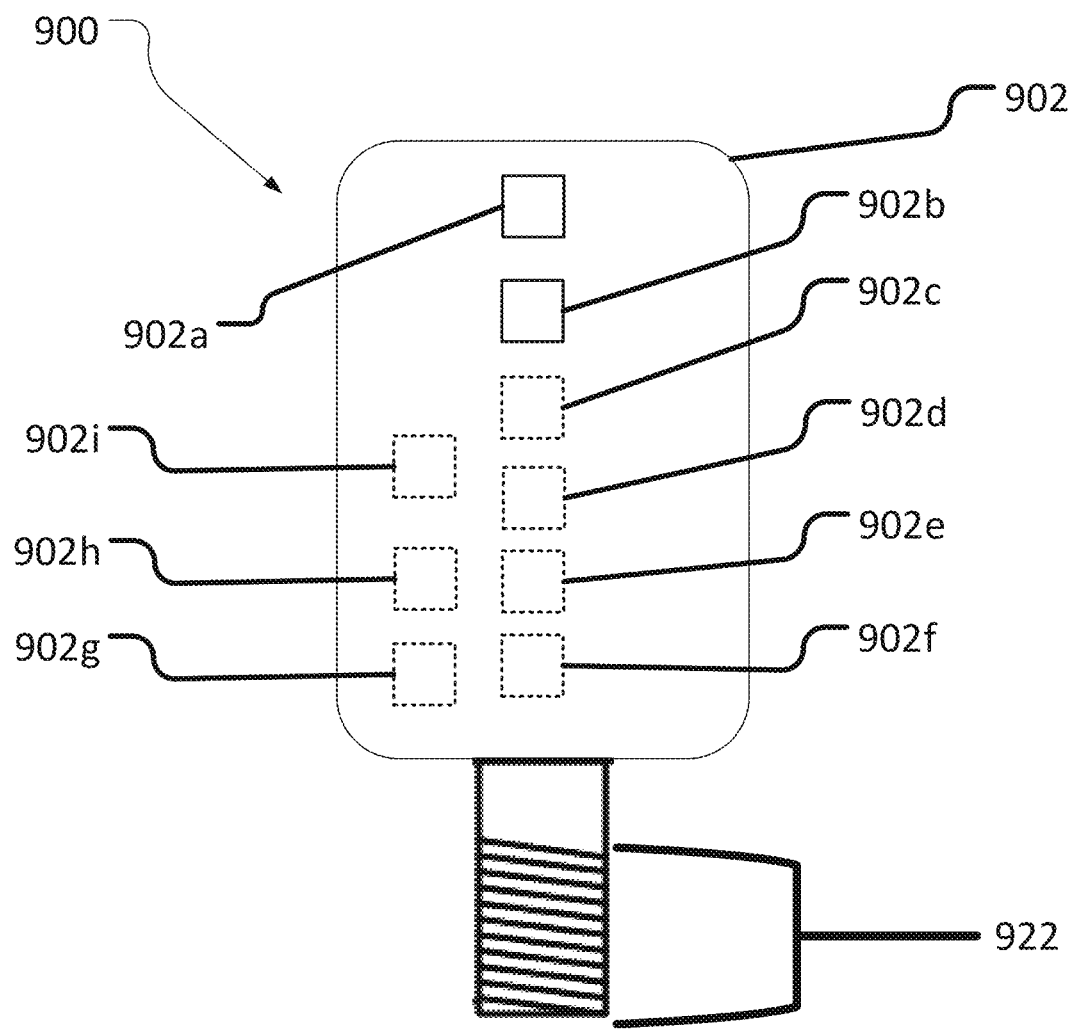
FIG. 9 shows a portable vaporizer device according to one or more aspects of the present invention.

In some embodiments, a sleeve may have a threading substantially identical to, e.g., a 510-threaded cartridge for coupling with a battery section (e.g., the embodiment of FIG. 9). The sleeve establishes an electrical connection to a battery section via this threading. In some embodiments, a sleeve may be a simple load, shared (e.g., series or parallel connection) with a cartridge.

In other embodiments, a sleeve may include a microprocessor, which is merely powered by a battery section, and controls, for example, the switching speed based on a pre-set time or percent of a duty cycle, and/or based on a sensor arranged on the sleeve to read, for example, a heat or vapor characteristic of the cartridge (e.g., heat at the electrical connection, vapor quality, etc. . . . ).

Cartridges may omit a mouthpiece in some embodiments. Indeed, embodiments may include both thread-less cartridge electrical contact (e.g., when a sleeve or adapter is electrically arranged between a battery and cartridge) and "mouthpiece-less" cartridge such that mouthpiece 502a takes the place of mouthpiece 110 by further defining the airpath from a cartridge (e.g., extending airpath 112 defined by the central tube of a cartridge).

In "mouthpiece-less" embodiments, the "mouthpiece side" of the cartridge may have a planar or planar-like surface with a perforable membrane (e.g., foil) above it. The membrane may be perforated by closing mouthpiece 502a onto a mouthpiece-less cartridge. In some embodiments, the cartage interface defines a "sub mouthpiece" protrusion adapted to mechanically couple with mouthpiece 502a, but may otherwise not easily couple directly with a user's mouth for establishing an airpath.

FIGS. 6A, 6B, 7A, and 7B are possible schematic cross sections along cutting planes A and B of one of devices 200, 400, and 500. The sleeve and battery section may be coupled via mechanical (e.g., threaded) or magnetic means and electrically coupled via alternative arrangements and configurations such as those shown in these figures.

Figure 6A:
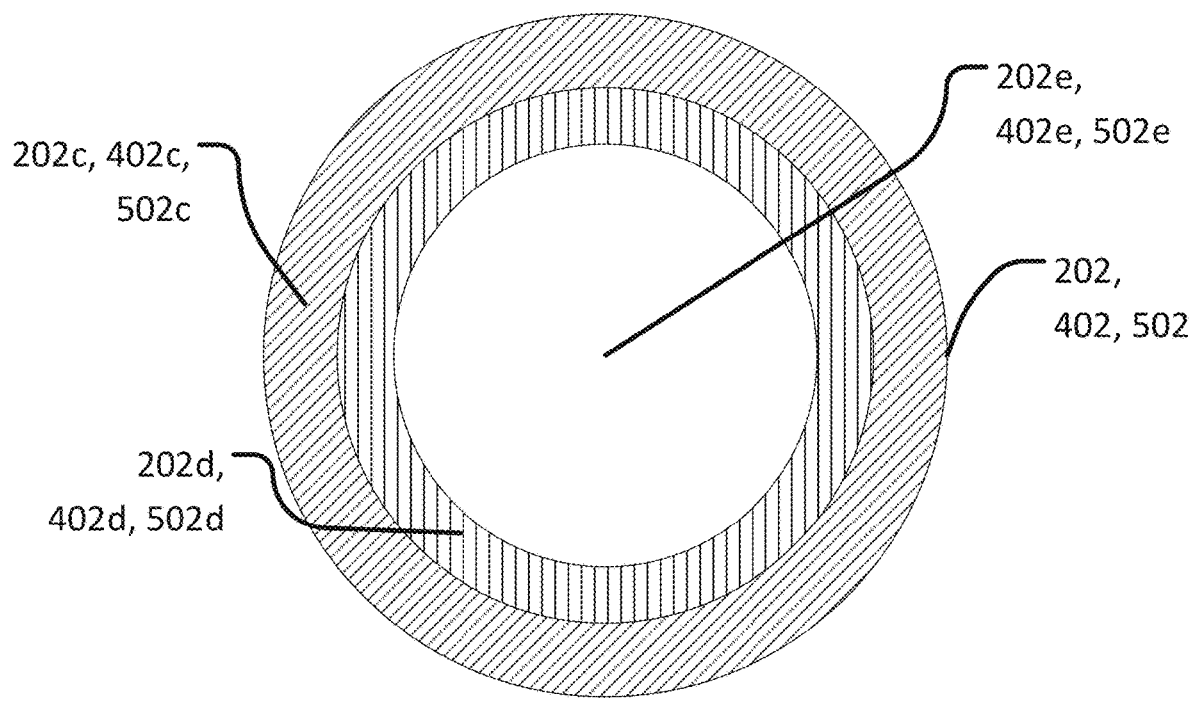
FIGS. 6A and 6B show a portable vaporizer device according to one or more aspects of the present invention.

The sleeve shown in FIG. 6A includes electrical leads 202c, 402c, 502c as, for example, negative or ground, and electrical leads 202d, 402d, 502, as, for example, positive or "hot". Isolation between the electrical leads are not shown in this or similar figures. The sleeve defines aperture 202e, 402e, 502e. The electrical leads may be different sizes or shapes than shown or even replaced with electrical wiring in some embodiments.

Figure 6B:
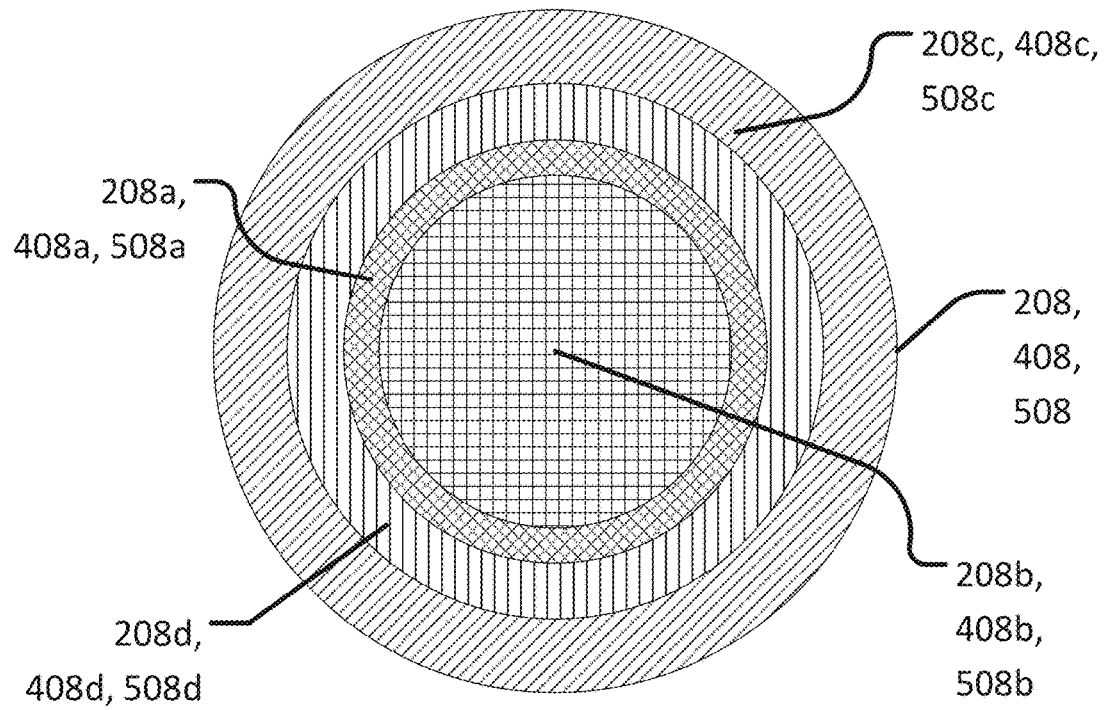

FIG. 6B shows the corresponding leads 208c, 408c, 508c and 208d, 408d, 508d on battery section 208, 408, 508. The battery section further includes the leads and/or coupling mechanism for a cartridge or an adapter interface thereof, such as adapter 2320 of FIG. 23. For example, lead 208a, 408a, 508a may define a threaded coupling for a cartridge. Lead 208b, 408b, 508b may be a ground or negative lead for a cartridge when the cartridge is coupled to a battery section. Said leads may be a part of a magnetic interface shown in FIG. 23.

Figure 7A:
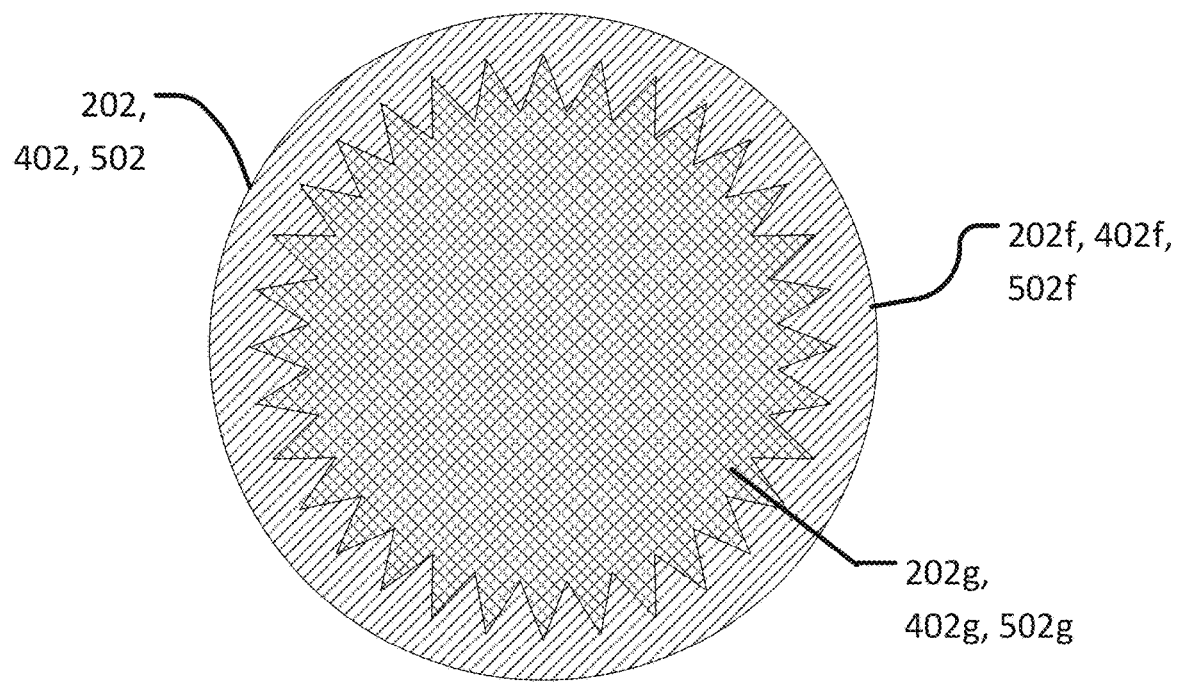
FIGS. 7A and 7B show a portable vaporizer device according to one or more aspects of the present invention.
Figure 7B:
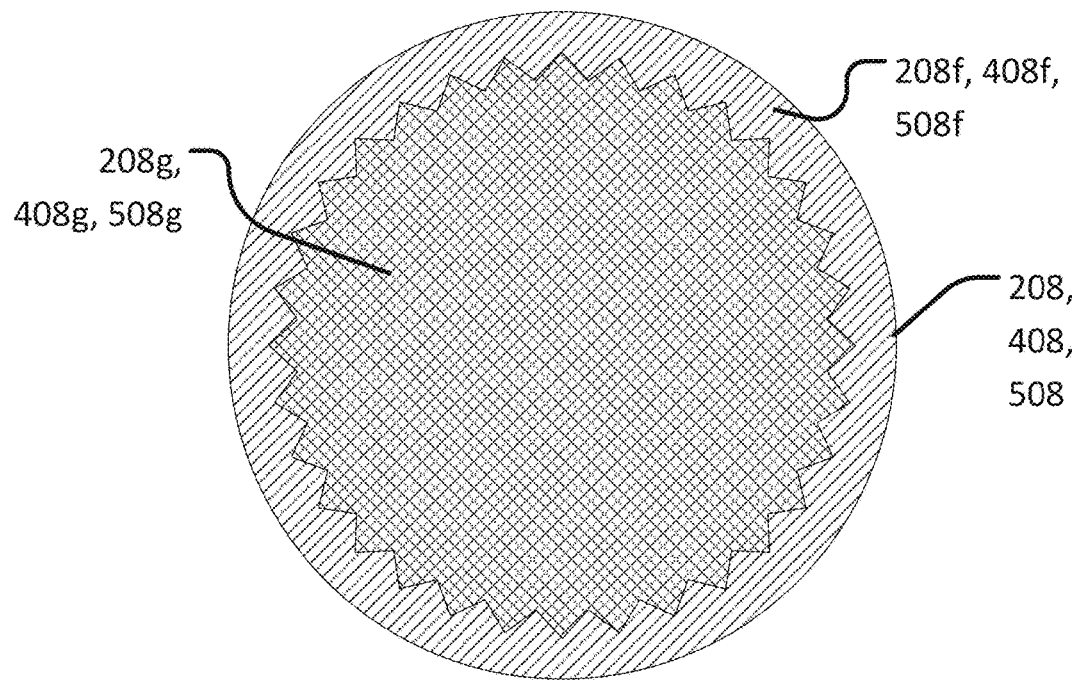

The embodiment shown in FIGS. 7A and 7B provide a "simpler" interface that includes magnetic coupling elements 202f, 402f, 502f and 208f, 408f, 508f. The magnetic coupling elements may be ferrous material and/or magnets arranged such that the sleeve connects to the battery section. Electrical circuit elements 202g, 402g, 502g and 208g, 408g, 508g, which may include leads that rely on physical contact (e.g., as shown in FIGS. 6A and 6B) or elements arranged in closed proximity to each other such that wireless power transfer can occur over said elements. In such embodiments, elements 202g, 402g, 502g and 208g, 408g, 508g may be wireless power transfer elements such as coils.

The sleeve of FIGS. 7A and 7B does not define an aperture along cutting plane A for allowing the cartridge to pass through. Rather, such sleeves are an electrical interfacing piece between a cartridge and battery.

In alternative embodiments, sleeve 202, 402, 502 may be integral with (or otherwise not easily uncoupled without tools and time) battery section 208, 408, 508. In such embodiments, a sleeve and battery section may be wired together in forming an electrical circuit or circuits. In such embodiments, the battery section and/or sleeve may define a mechanical and/or magnetic coupling interface for coupling with a cartridge or an adapter thereof (e.g., adapter 2320).

FIGS. 8A to 8D show various airpath configurations. Sleeves may include rigid or semi-rigid materials. In semi-rigid embodiments, the sleeve may be slightly stretched around the cartridge (e.g., the defined aperture is dimensioned to accommodate a cartridge by slightly enlarging (stretching) said aperture). In this case, coupling is achieved by an elastic/deformable material gripping onto a cartridge's surface and/or a battery section's surface.

Sleeve 802A includes air intake features 804a, 804b (arranged on an outer surface of sleeve 802A) of a spiral airpath channel 810, and air outlets 808a, 808b, (arranged on an inner surface of sleeve 802A) of the spiral airpath channel 810. Air outlets 808a, 808b are in fluid communication with a heater and mouthpiece such that when a user takes a draw, air is drawn in from features 804a, 804b, through the spiral channel(s) 810 defined within the sleeve, to outlets 808a, 808b, then on to the heater and mouthpiece, with a possible second AME arranged, along the airpath, between a heater and mouthpiece.

Sleeve 802A defines aperture 806 for accommodating a cartridge. Sleeve 802A will typically form a sufficient seal with the cartridge such that the majority of the air drawn through a heater is provided by outlets 808a, 808b.

Figure 8B:
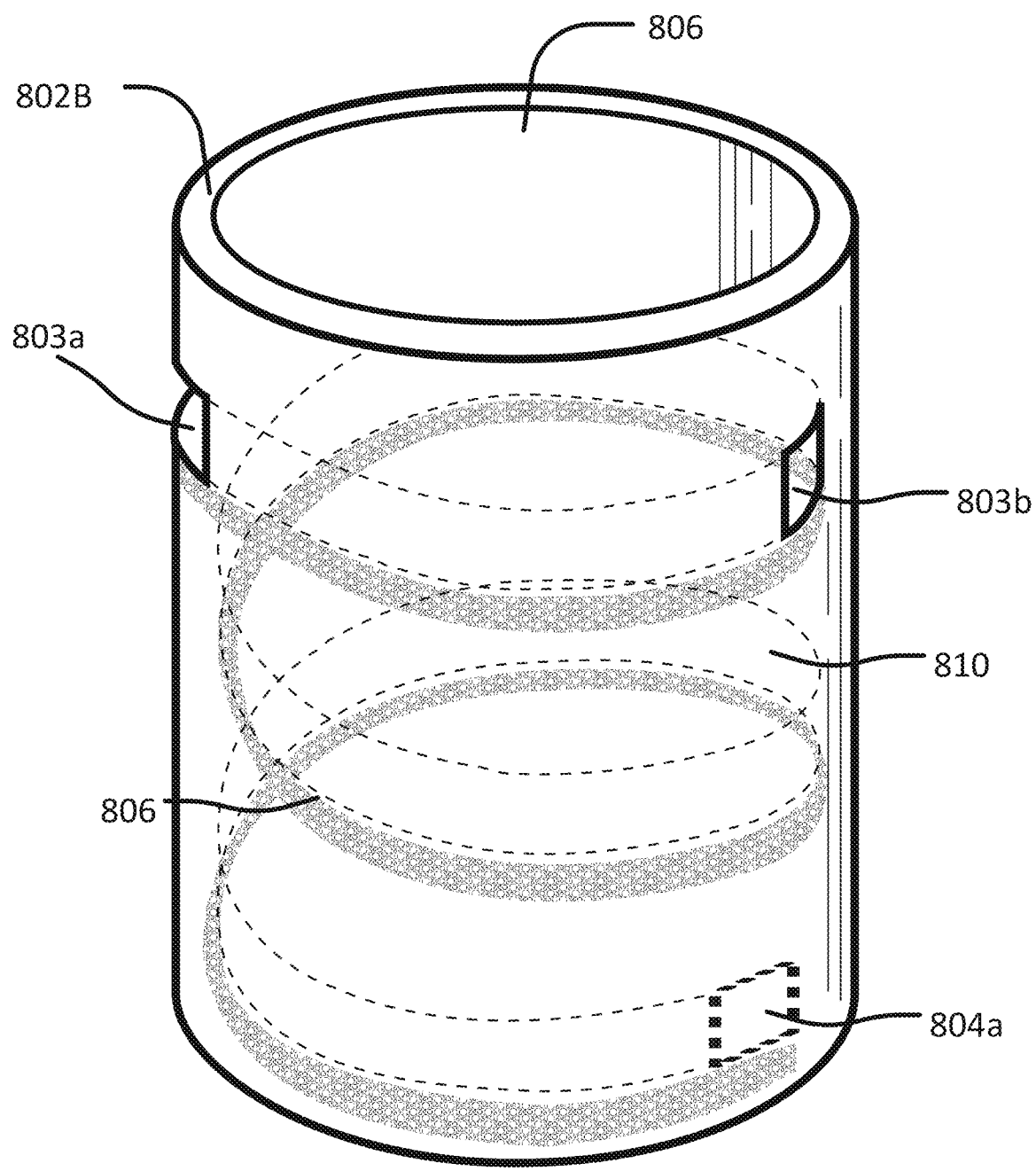
Figure 8C:
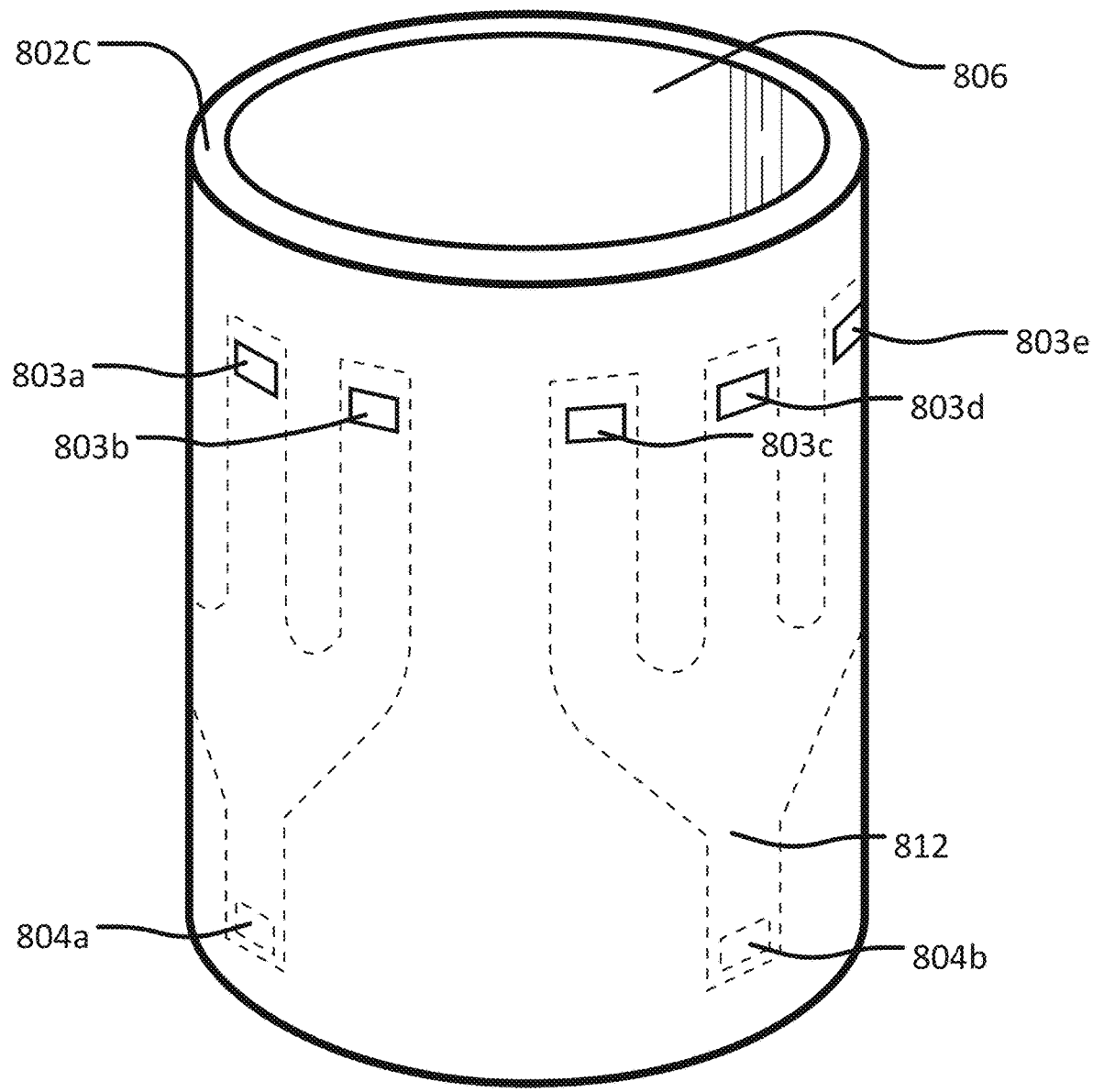
Figure 8D:
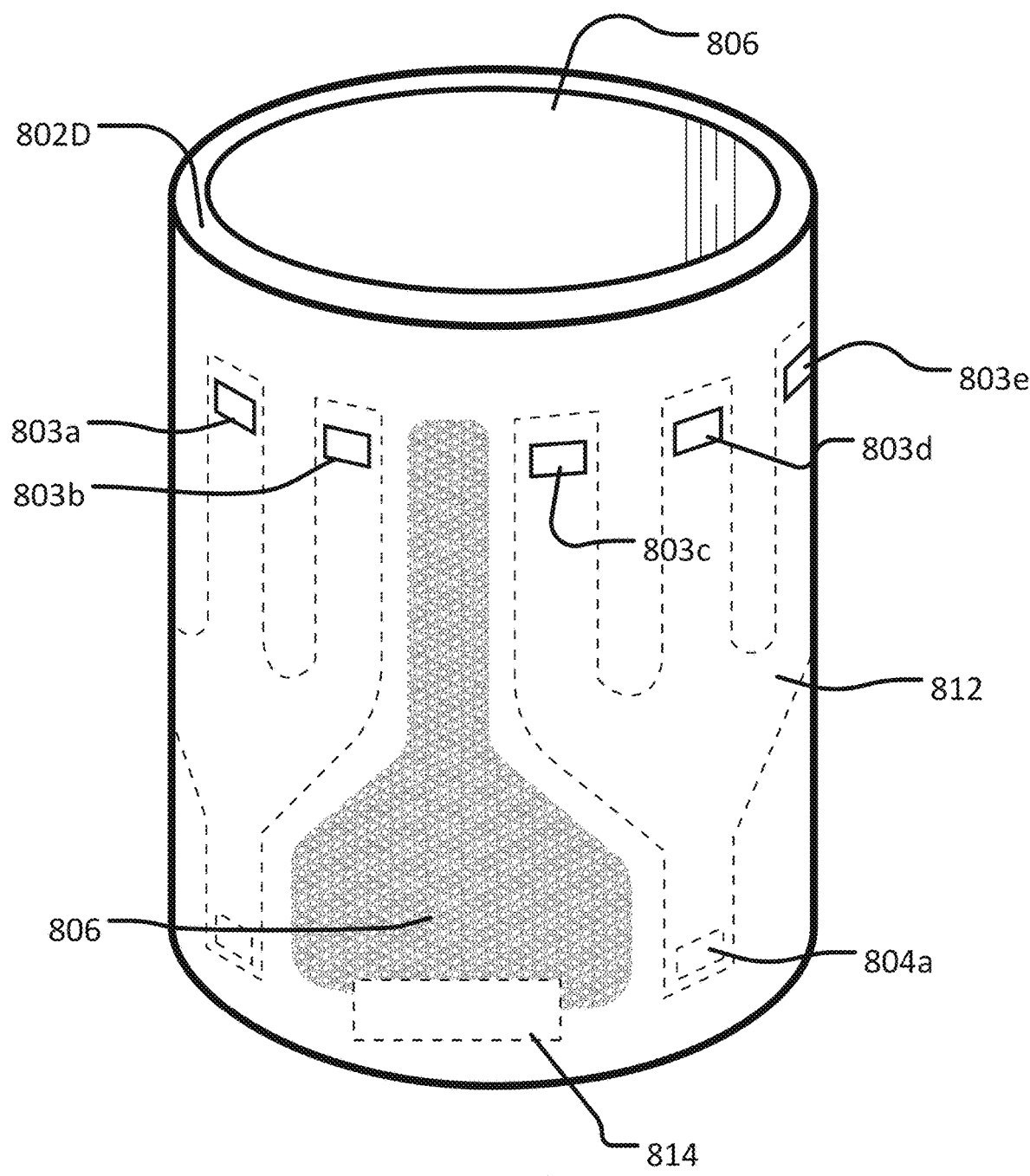

Sleeve 802B of FIG. 8B further includes, in relation to sleeve 802A, refrigerant gel 806, which is thermally coupled to spiral channel 810. Sleeve 802C defines manifold airpath channel 812, which, on one side, is fed by a plurality of air intake features (e.g., 803c, 803d, 803e) that all feed a single outlet (e.g., 804b). Sleeve 802D is similar to sleeve 802C, but further includes refrigerant gel 806, which is thermally coupled to manifold channel 812. Sleeve 802D may further include Peltier device 814 for cooling refrigerant gel 806 or other cooling media contained within a sleeve.

The manifold channels of sleeves 802C and 802D may rapidly increase the air velocity by narrowing the airpath channel, combining velocity streams.

Device 900 includes sleeve 902, air intake feature 902a, and threading 922 for coupling with a battery section. Sleeve 902 may be powered by a battery section in performing one or more functions, including powering one or more of AME 902b, user input sensor 902c, variable resistance element 902d, draw sensor 902e (which may be a type of user input sensor), display 902f, controller 902g, and switch 902h for selectively applying power from a battery section to, for example, a cartridge's heater. Coupler 902i is adapted to couple with a cartridge or an adapter interface thereof, such as adapter 2320 of FIG. 23.

A user may, via user input sensor 902c, push a button, shake device 900 (e.g., an accelerometer), or increase/decrease draw strength (e.g., a draw sensor) for modifying, for example, the master duty cycle, which controls the ratio of ON to OFF time of switch 902h or, in some embodiments, a ratio of two applied voltages (e.g., a ratio of a high to low applied voltage). Among many possible examples, switch 902h may toggle such that a high voltage is applied to the heater in a first switch position and a low (or no) voltage is applied in a second, switch position. The master duty cycle may be selectively toggled among 25%, 50%, 75%, and 100% duty cycles with a total period of each cycle being between, for example, 1 and 3 seconds.

In some embodiments, the resistor value of variable resistive element 902d may be "ramped" up and down according to similar period lengths of each cycle (e.g., 1 to 3 seconds). In a sense, this is modulating the current applied from a battery section as it either toggles (binary) or ramps up/down resistance values of element 902d. In such embodiments, a user may be able to select at least one of the "width" of the modulation (e.g., variable resistor end points (e.g., 0.5-1Ω, 1-2Ω, 1-5Ω)) and period or frequency (e.g., 60 to 0.5 Hz control signals (e.g., 1 to 2 second cycles)).

Besides user input sensor 902c, the above-describe values may be entered via a separate device communicatively coupled to device 900 via an app installed on a smart phone or other user equipment (e.g., tablet, PC, etc. . . . ).

Figure 10A:
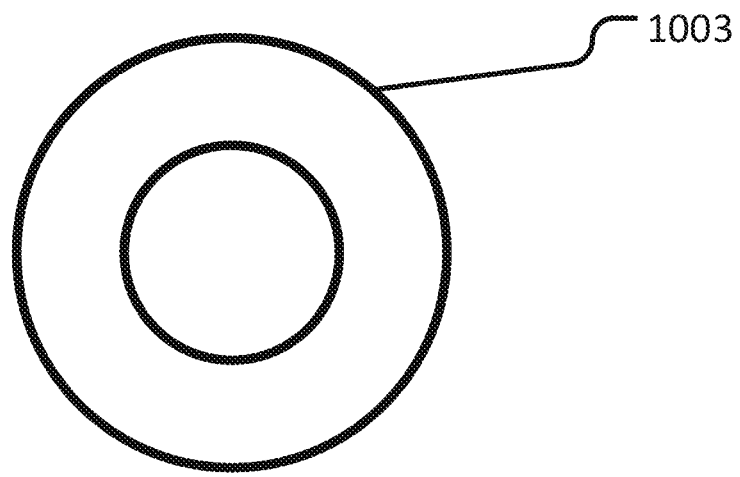
FIGS. 10A and 10B show a Peltier device.
Figure 10B:
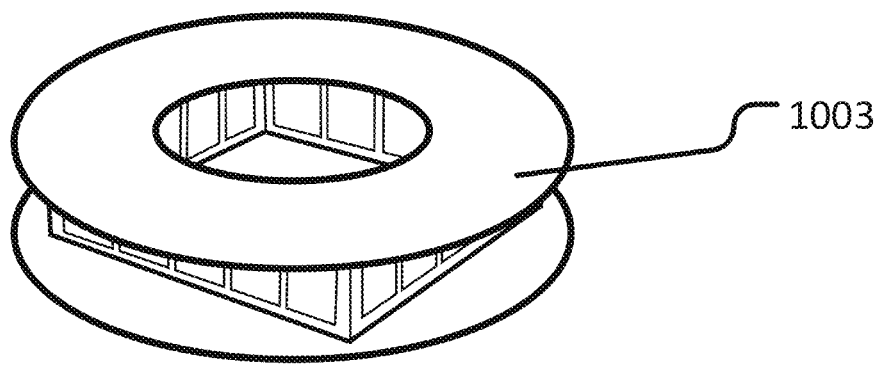

FIGS. 10A-C show Peltier device 1000, which has a cold and hot side when electrical power is applied. Peltier device 1000 may thermally couple to air flowing through a sleeve via direct exposure (of the air) to Peltier device 1000 or via an interfacing material (e.g., metal arranged between a Peltier device and an airpath channel).

Figure 11:
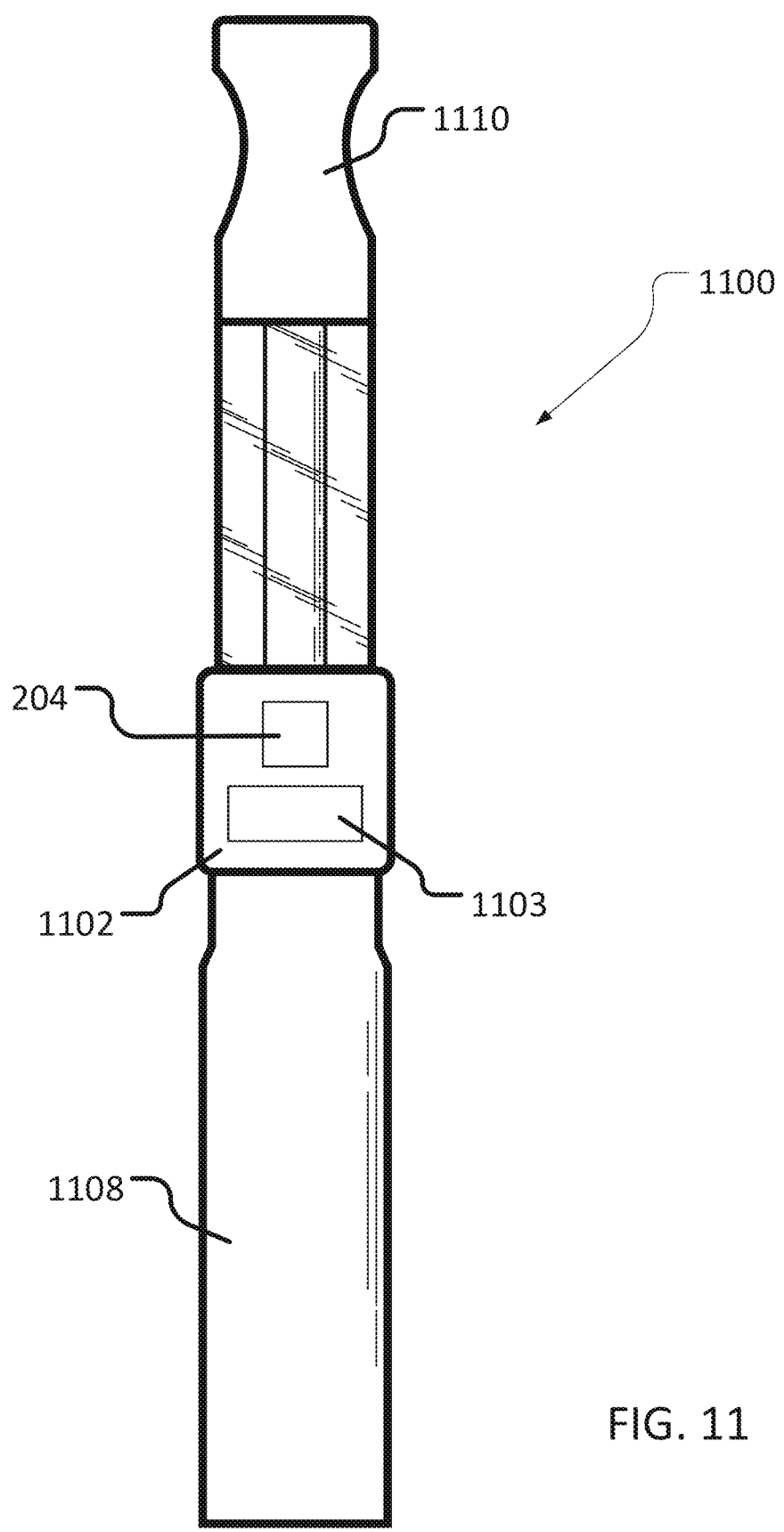
FIG. 11 shows a portable vaporizer device according to one or more aspects of the present invention.

FIG. 11 shows portable vaporizer device 1100 with sleeve 1102, Peltier device 1103, battery section 1108, and mouthpiece 1110. FIG. 11 is a "short sleeve" embodiment in which the Peltier device 1103 may, for example, lower the intake air's temperature upstream of a heater. In some embodiments, a controller may synchronize or otherwise coordinate the operation of the heater (not shown) and a Peltier device. For example, respective duty cycle ON/OFF periods of the heater and Peltier device may overlap or be completely "out-of-phase" such that each ON and OFF period of one duty cycle occurs during the opposite state of the other duty cycle.

Figure 12:
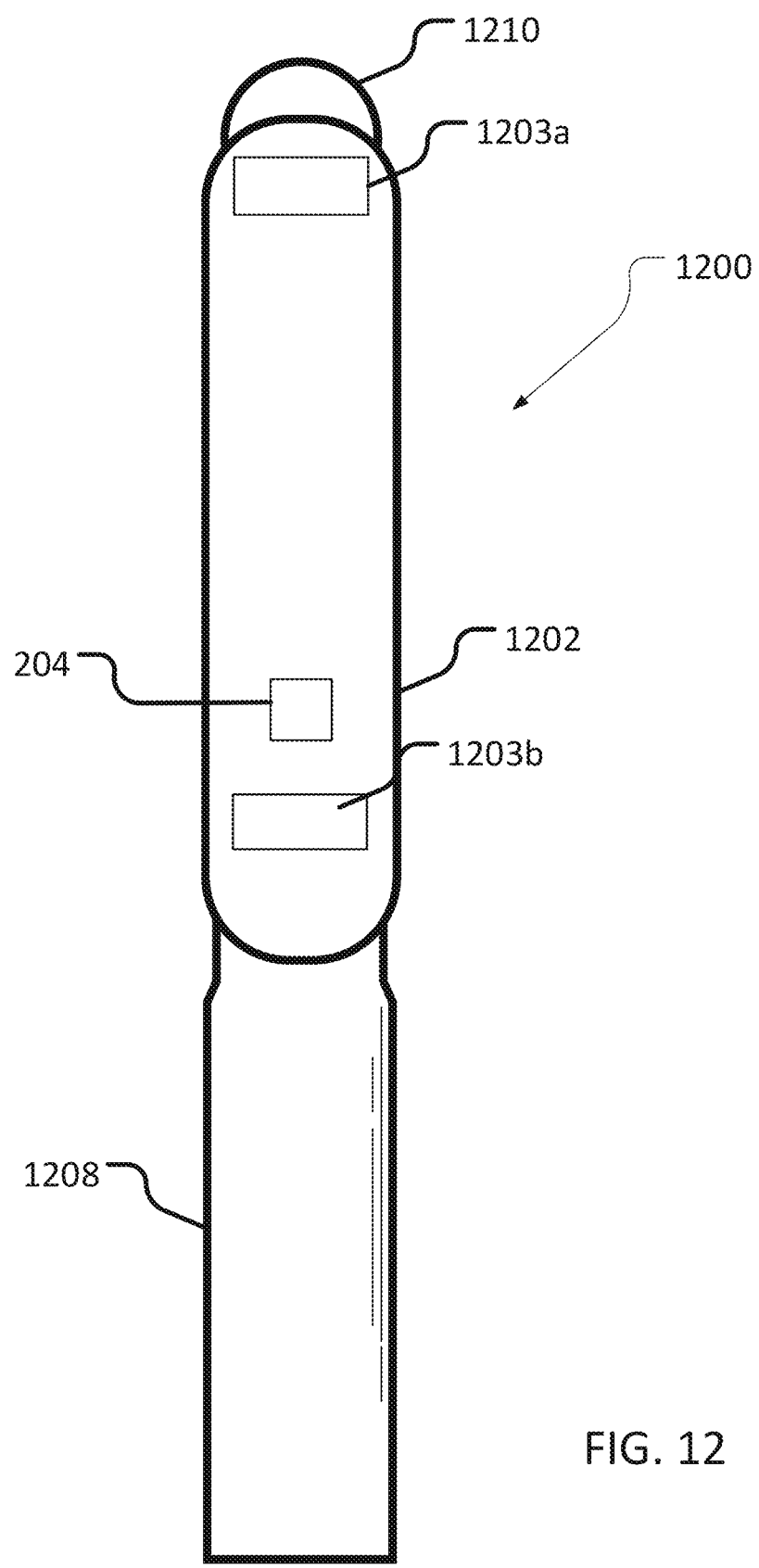
FIG. 12 shows a portable vaporizer device according to one or more aspects of the present invention.

FIG. 12 shows portable device 1200 with sleeve 1202, Peltier device 1203a and 1203b, battery section 1208, and mouthpiece 1210 of a "full-sleeve" embodiment. Peltier device 1203 a may affect the temperature of "pre-mouthpiece" air (e.g., post heater air containing an aerosol). Device 1200 may further include a further Peltier device 1203b or a different AME that modifies air upstream of a heater (not shown).

Figure 13:
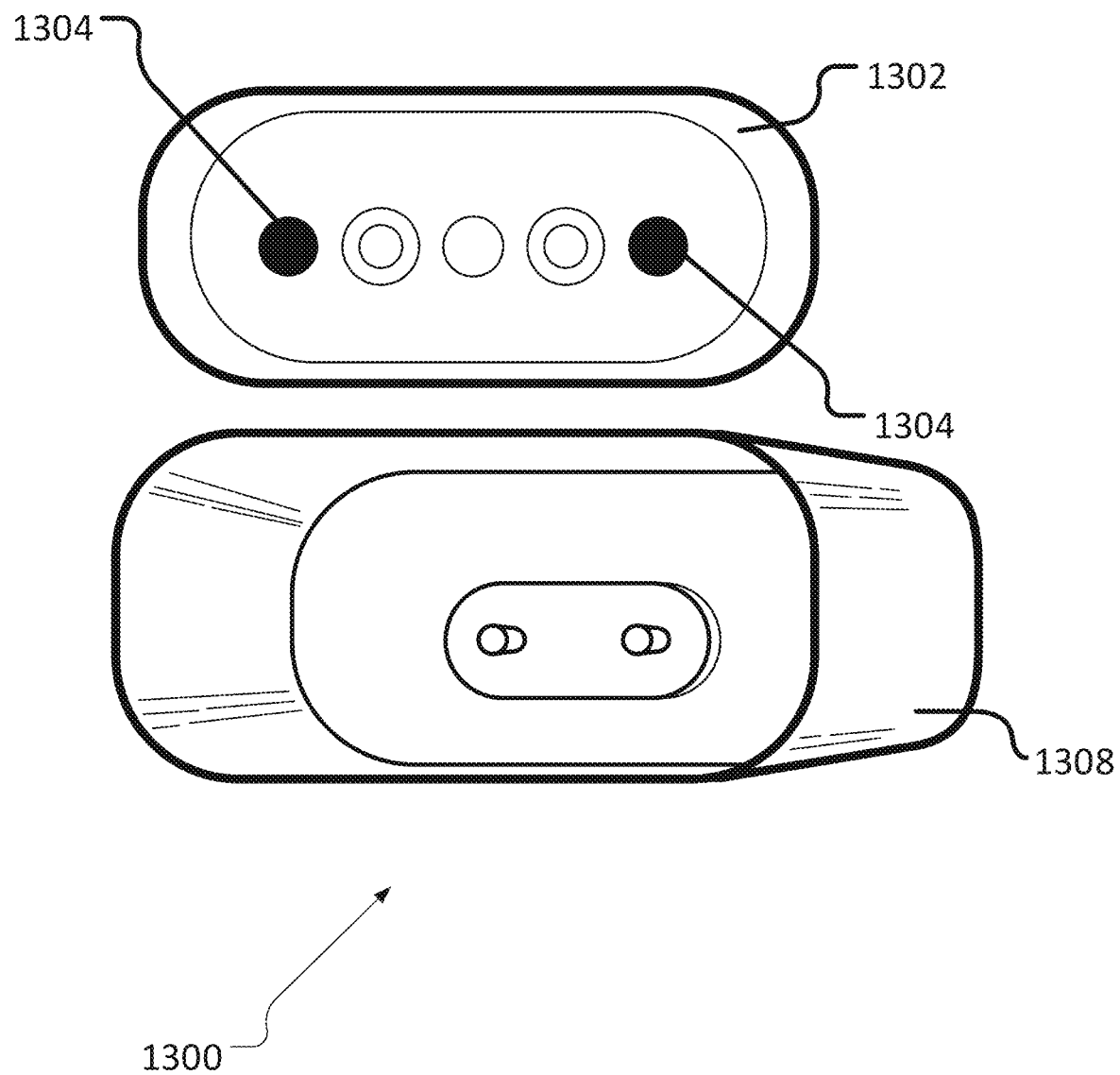
FIG. 13 shows a prior art portable vaporizer device.

FIG. 13 shows prior art device 1300, which includes cartridge 1302 with air intake features 1304, and battery section 1308.

Figure 14A:
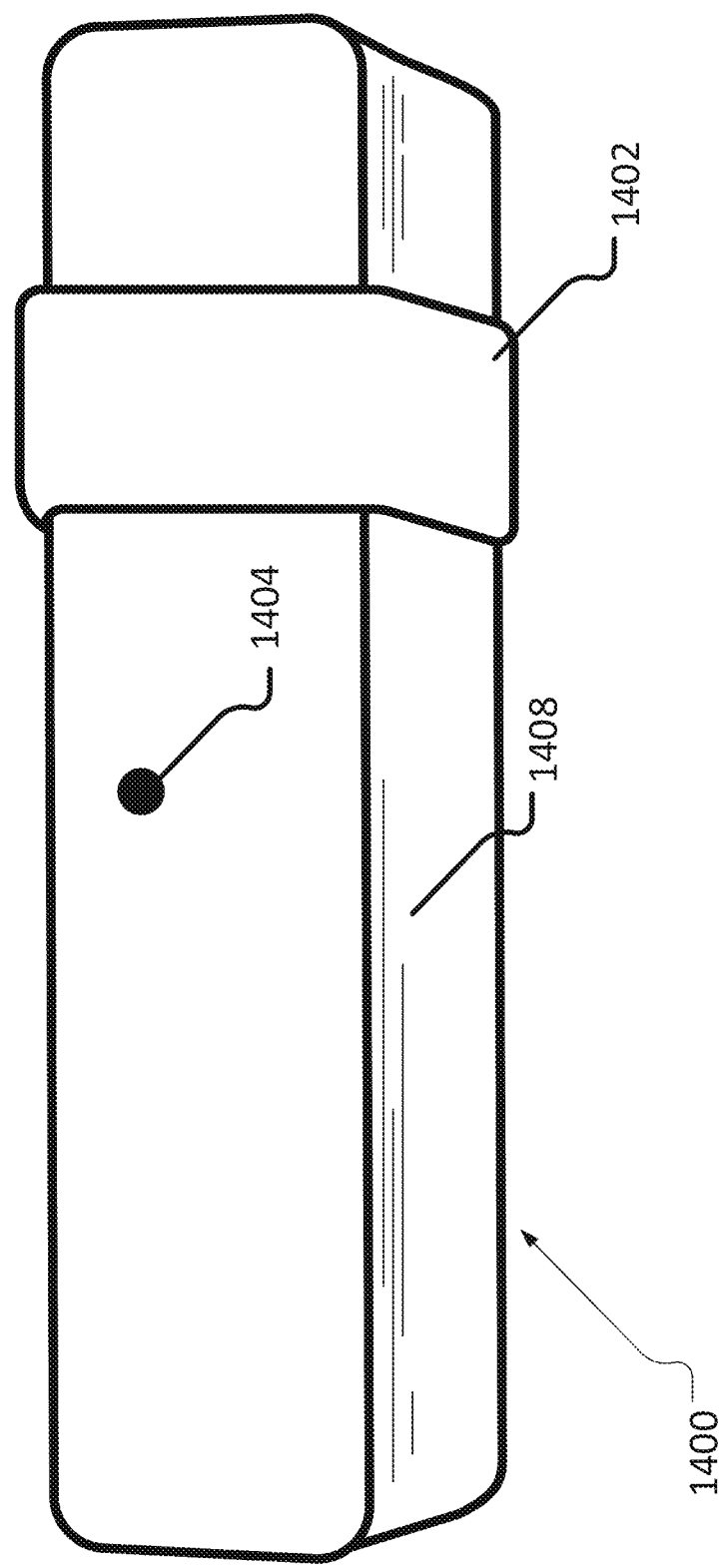
FIGS. 14A and 14B show a portable vaporizer device according to one or more aspects of the present invention.
Figure 14B:
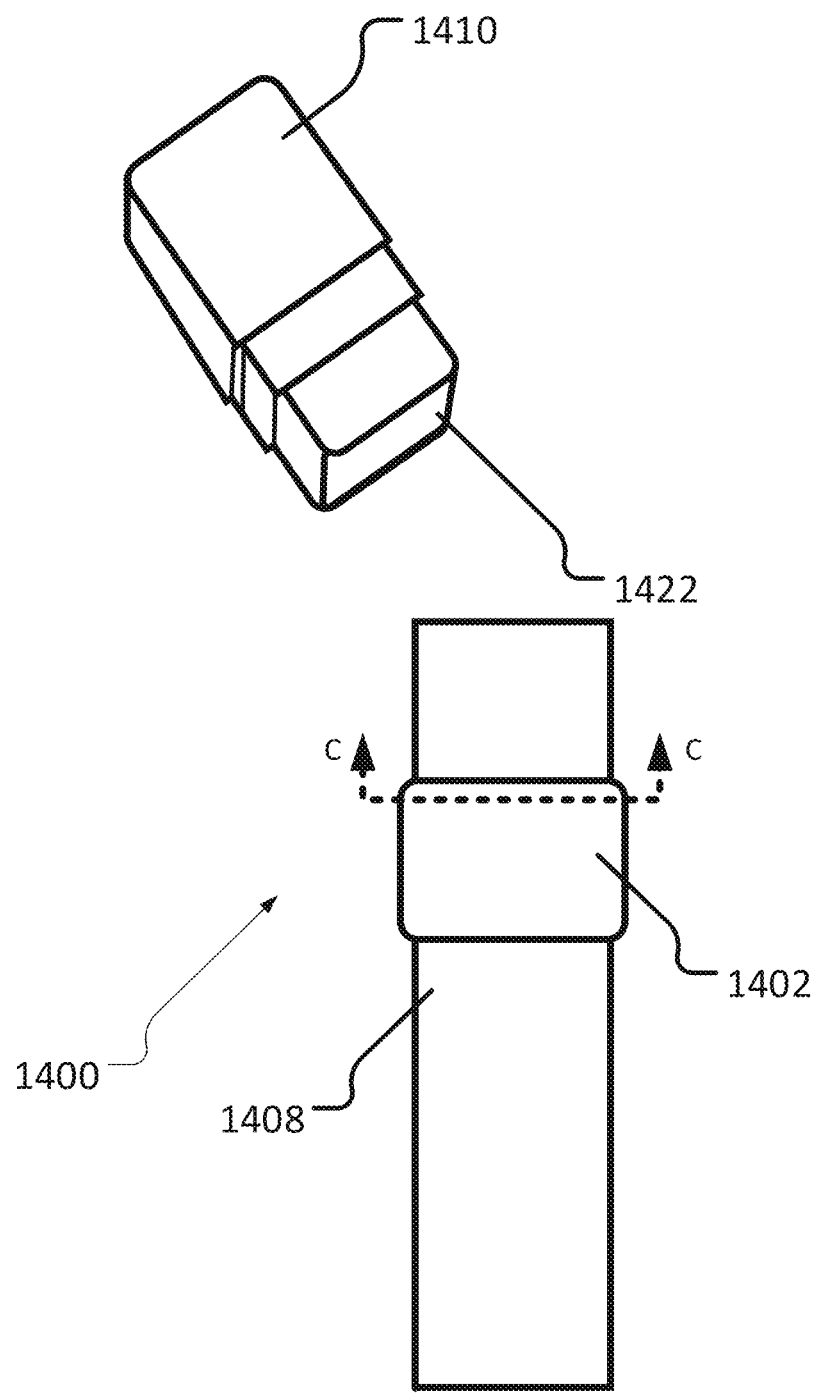

FIGS. 14A and B show portable vaporizer device 1400, which defines air intake features 1404 (only one shown) of battery section 1408. Battery section 1408 couples with cartridge 1422, which incorporates mouthpiece 1410. Sleeve 1402 slides along the surface for battery section 1408 and may be placed such that sleeve 1402 surrounds air intake features 1404. Sleeve 1402 thus modifies air upstream of device's 1400 heater (not shown).

Figure 15:
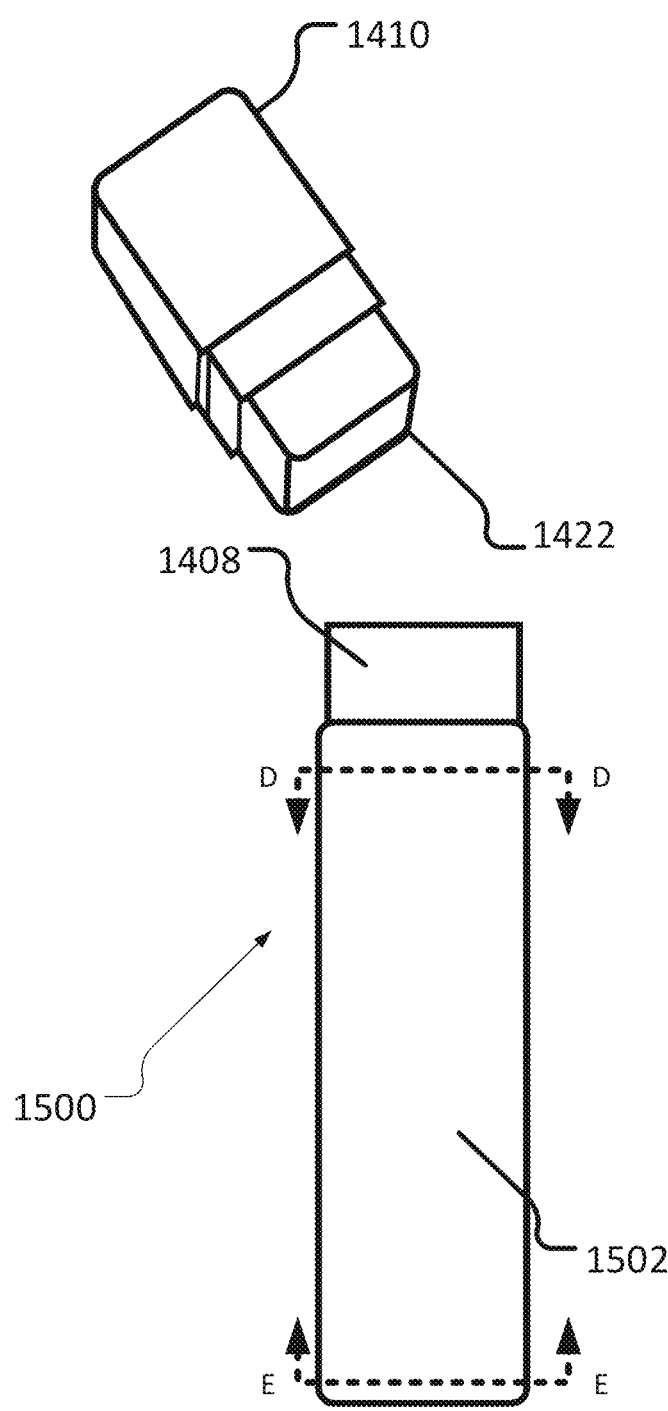
FIG. 15 shows a portable vaporizer device according to one or more aspects of the present invention.

FIG. 15 shows device 1500 with a longer sleeve, sleeve 1502.

FIGS. 16A to 16C are cross-sectional views of alternative sleeves 1402 (and doesn't include battery section 1408) along cutting plane C. FIG. 16D is a view of possible configurations of distal and/or proximal ends of sleeve 1402. In FIGS. 16A to 16C, sleeve 1402 is "aligned" so to establish fluid (air) communication with its air intake features (e.g., air intake features 1403a to 1403d) and air intake features 1404 of battery section 1408. In FIG. 16D, the air intake features 1403a and 1403b (and possibly more such as 1403e) are in fluid communication with air intake features 1404 of battery section 1408. Embodiments of 16A to 16C may be combined with the embodiment of FIG. 16D.

Figure 17A:
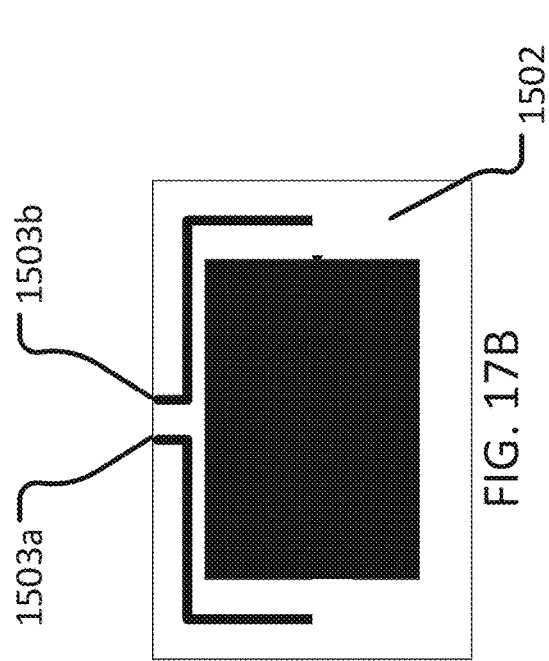
FIGS. 17A to 17D show a portable vaporizer device according to one or more aspects of the present invention.
Figure 17B:
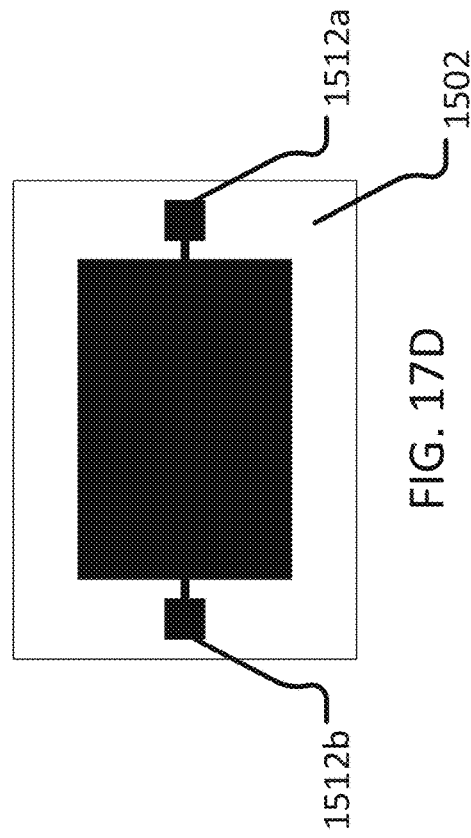
Figure 17C:
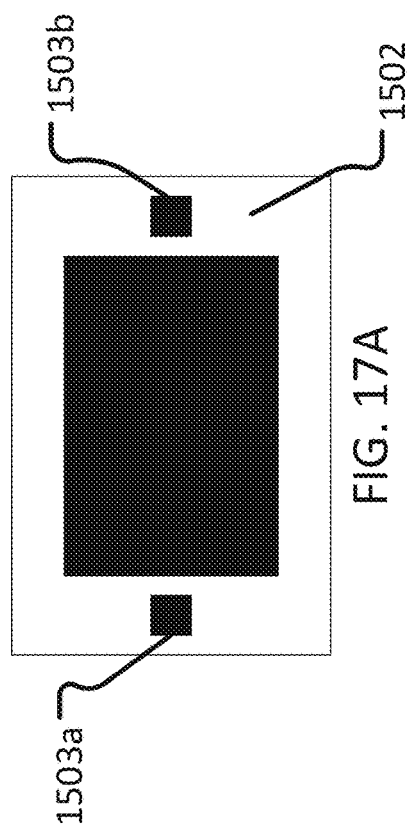
Figure 17D:
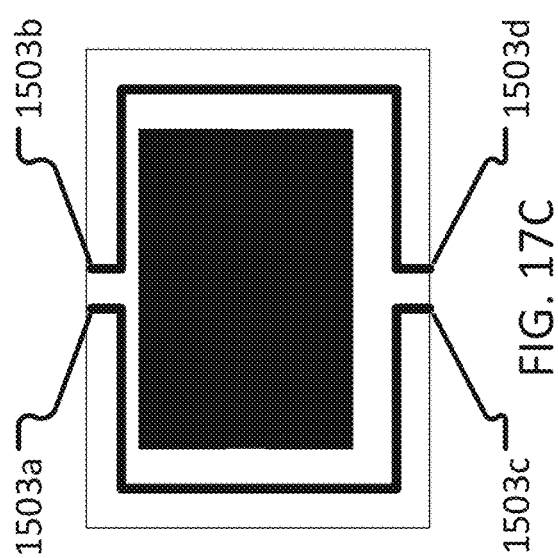

FIG. 17A is a view of possible configurations of distal and/or proximal ends of sleeve 1502, which defines air intake features 1503a and 1503 and airpath channels thereof, which couples said air intake features with the air intake features 1404 of battery 1408. FIGS. 17B and 17C are cross-sectional views of alternative sleeves 1502 (and doesn't include battery section 1408) along cutting plane E. FIG. 17D is a cross-sectional view of sleeve 1502 along cutting plane D. Sleeve 1502 defines air intake features 1503a to 1503d, depending on the embodiment, which are coupled to airpath channels 1512a and 1512b, which are arranged between said air intake features and air intake features 1404 of battery 1508. Embodiments of 17A to 17C may be combined with the embodiment of FIG. 17D.

FIGS. 18A and 18B show a prior art portable vaporizer device 1800, particularly the distal end of battery section 1808. The proximal, mouthpiece end is not shown. Device 1800 shows oven 1806, which is thermally coupled to a heater (not shown). Device 1800 further includes air intake feature 1804 and lid 1810, which couples with the distal end of device 1800.

Figure 19A:
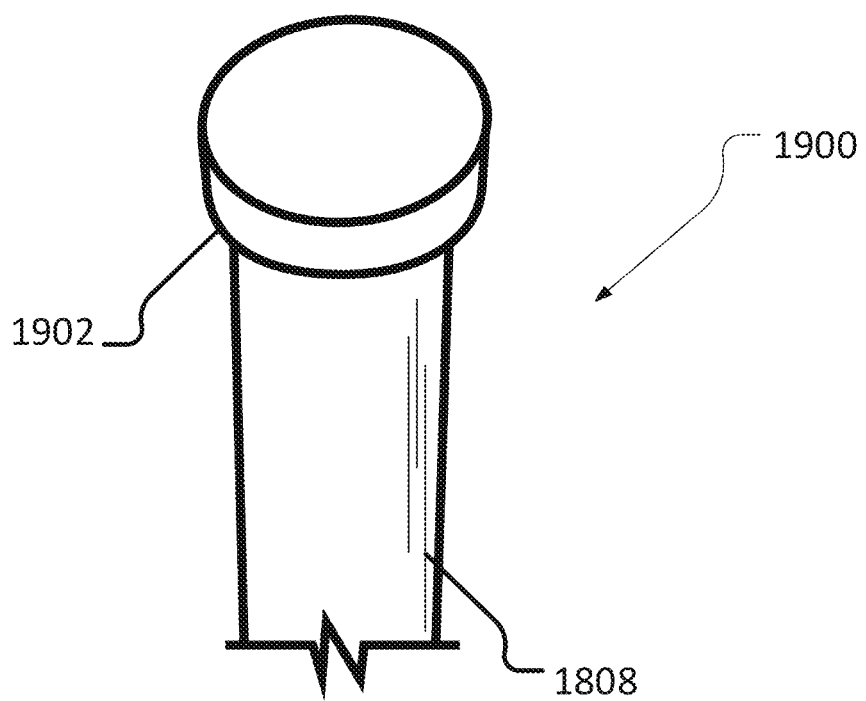
FIGS. 19A to 19D show a portable vaporizer device according to one or more aspects of the present invention.
Figure 19B:
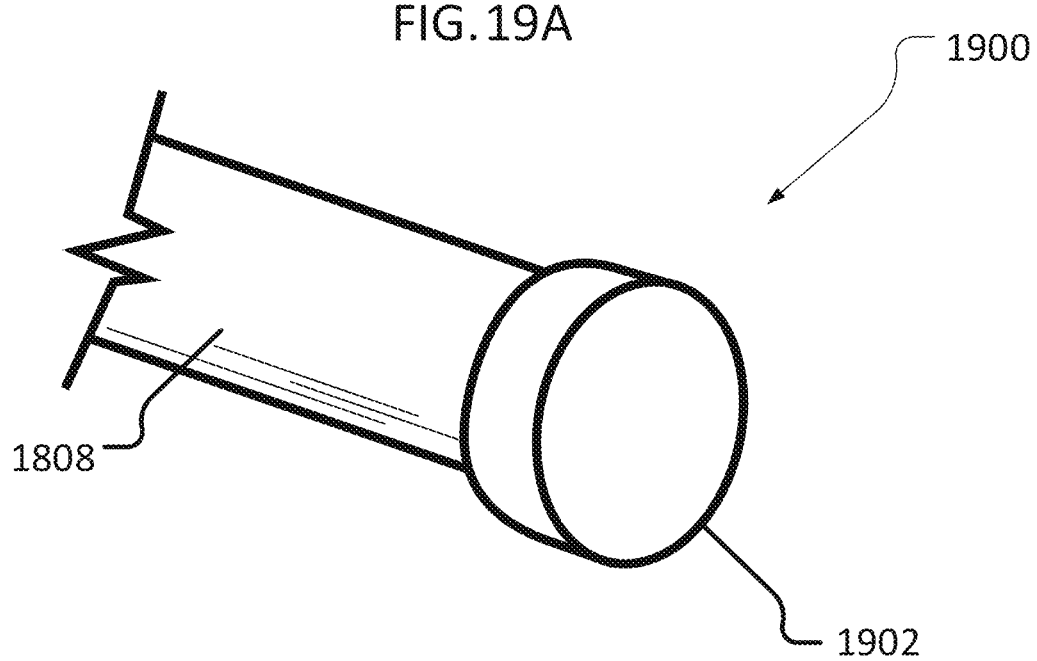
Figure 19C:
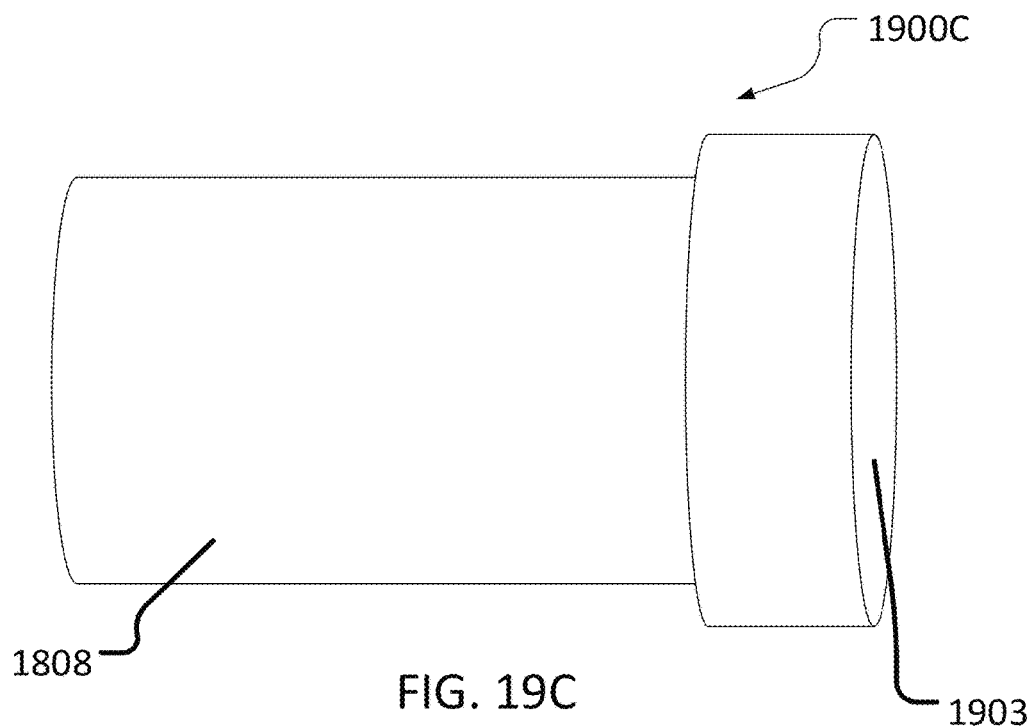
Figure 19D:
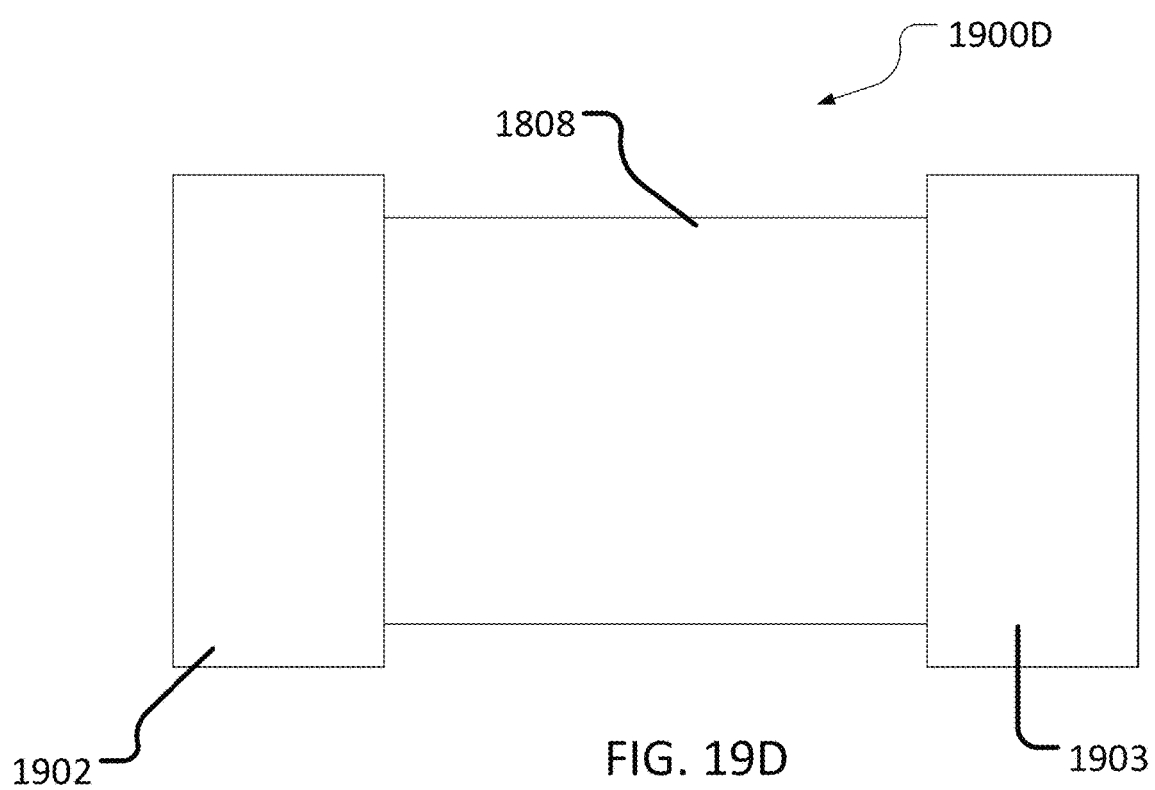

FIGS. 19A to 19D show portable vaporizer devices 1900, 1900C, and 1900D particularly sleeve 1902 coupled to the distal end of battery section 1808 and/or mouthpiece sleeve 1903 coupled to the proximal end of battery section 1808. The proximal, mouthpiece of battery section 1808 is not shown. FIGS. 19A to 19C are schematic, perspective views. FIG. 19D is a side view.

Sleeves 1902 and 1903 slides along the outer surface of the distal end of battery section 1808. Sleeves 1902 and 1903 may adopt one or more of the features discussed of other sleeves, include air intake features and air modification elements. For example, sleeves 1902 and 1903 may be a "cool puck" that each define a cavity for accommodating an end of battery section 1808. In passive embodiments (e.g., refrigerant coolants), sleeves 1902 and 1903 (or cool pucks) may be placed in a refrigerator or freezer and coupled before use of device 1900.

In some embodiments, sleeves 1902 and 1903 may be interchangeable. That is, a sleeve may act as a mouthpiece, cooling or moisturizing the air right before it reaches a user's mouth upon inhalation or be placed at the other end and achieve the same result for air upstream of device's 1900, 1900C, 1900D heater (not shown).

Figure 20A:
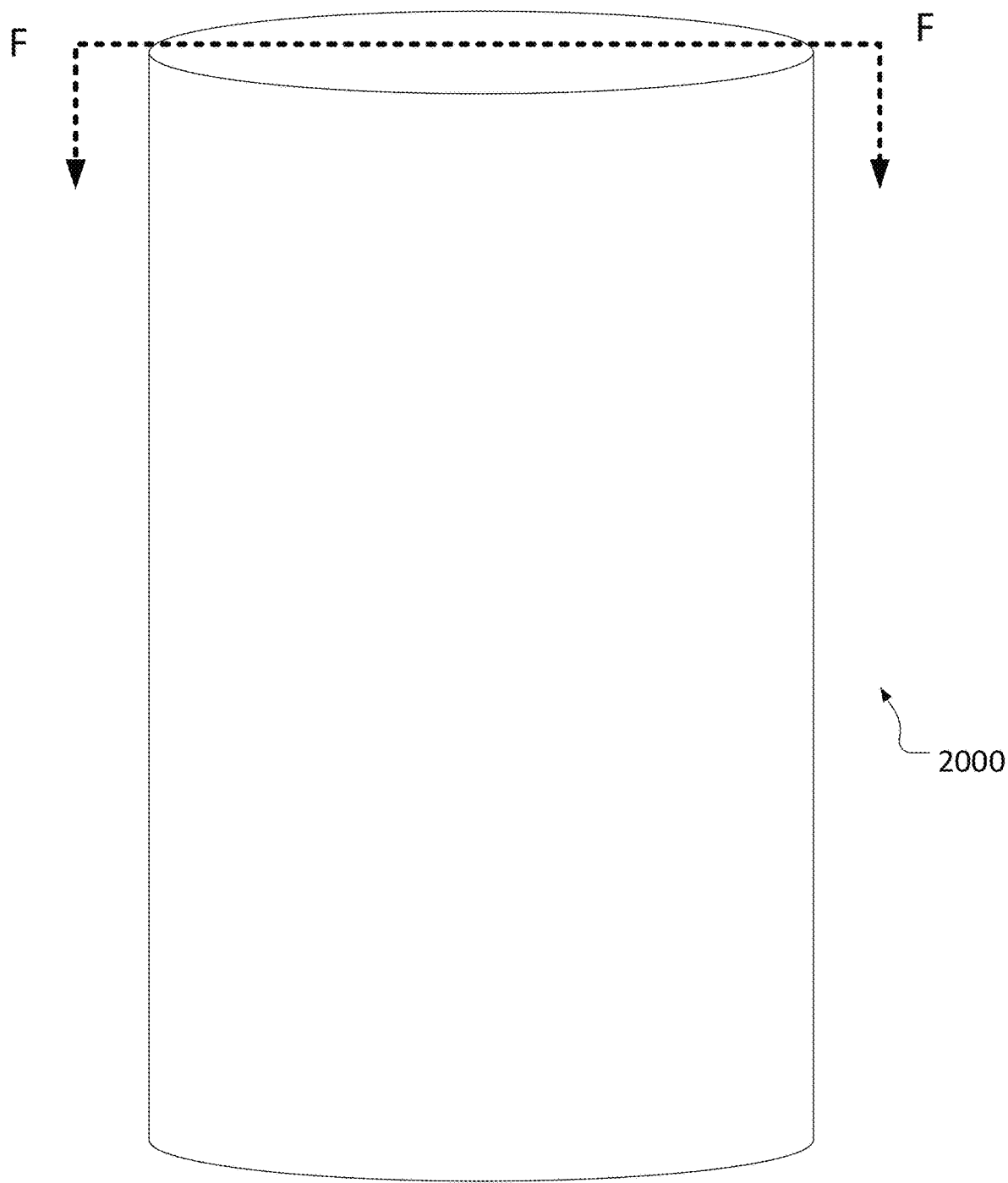

FIGS. 20A to 20C show portable vaporization device 2000. FIGS. 20B and 20C show alternative embodiments, depicted as cross sections along cutting plane F. Device 2000 has a distal side 2002 and proximal side 2004. On distal side 2002, oven 2008 is a cavity thermally coupled to Peltier device 2006b or 2006c. In either case, the hot side of Peltier device 2006b and c faces towards distal side 2002 and is thermally coupled to oven 2008 for vaporizing material (e.g., cannabis flower) placed in oven 2008. The cool side of Peltier device 2006b and c faces towards proximal side 2004 and may be thermally coupled to airpath channel 2012b or exposed directly to the air passing from oven 2008 to airpath channel 2012c.

In FIG. 20B air intake feature 2010b feeds channel 2012b whereas a plurality of air intake features 2010c, which have a "manifold arrangement" that feeds channel 2012c. In this embodiment, the individual elements of Peltier device 2006c define a plurality of air intake features 2012c. Device 2000 may further include a thin, porous screen 2014, which allows air through, but not material such as cannabis flower.

FIGS. 21A and 21B shows portable vaporizer device 2100, which is used for "user supplied" volatile substances (e.g., rosin, shatter, BHO extract, among other "concentrates"). Said substance is placed in bowl 2101 which includes or is coupled to a heater (not shown) powered by battery section 2108. Bowl 2101 may include air intake feature 204b and AME 203b.

After the substance is placed in bowl 2101, sleeve 2102 is coupled to bowl 2101, thereby establishing fluid communication between at least the heater and mouthpiece 2102a. In some embodiments, sleeve 2102 also establishes fluid communication upstream of the heater via air intake feature 204a. In some embodiments, sleeve may include AME 203a.

FIGS. 22A to 22D show portable vaporizer device 2200 with sleeves 2202A, 2202B, 2202C, and 2202D. In these embodiments, a deformable section mechanically couples to a cartridge or a section thereof. Sleeve 2202A, 2202B, and 2202C have three main parts: semi-rigid section 2203a, b, and c, AME 2206, and mouthpiece 2210. Section 2203a, b, and c is elastically deformable so to couple with at least one of cartridge mouthpiece 110 and the body of the cartridge 102. That is, the sleeves of these embodiments slide on and off of a cartridge and/or a mouthpiece thereof.

Figures 22A, 22B:
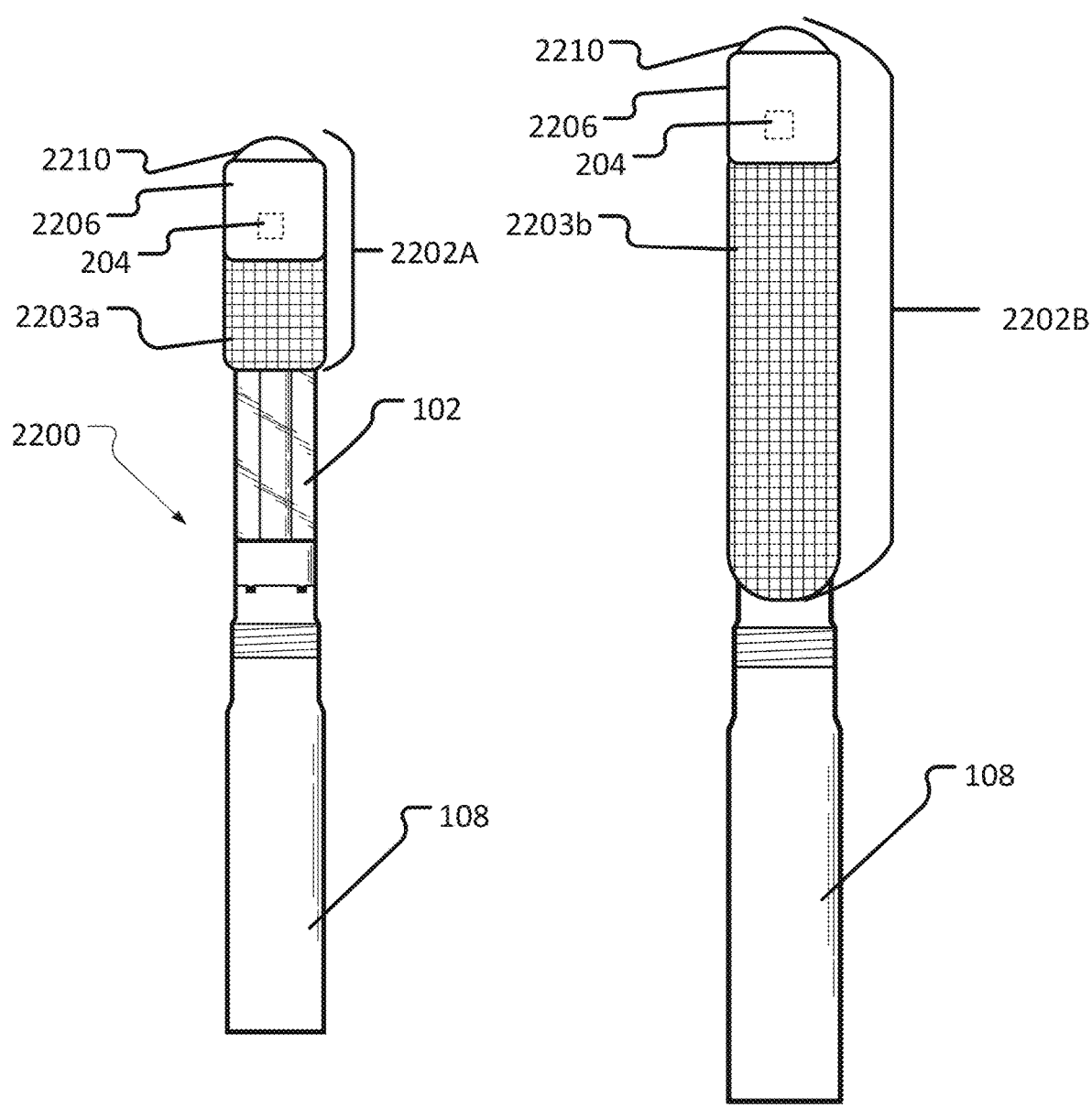
FIGS. 22A to 22D show a portable vaporizer device according to one or more aspects of the present invention.
Figures 22C, 22D:
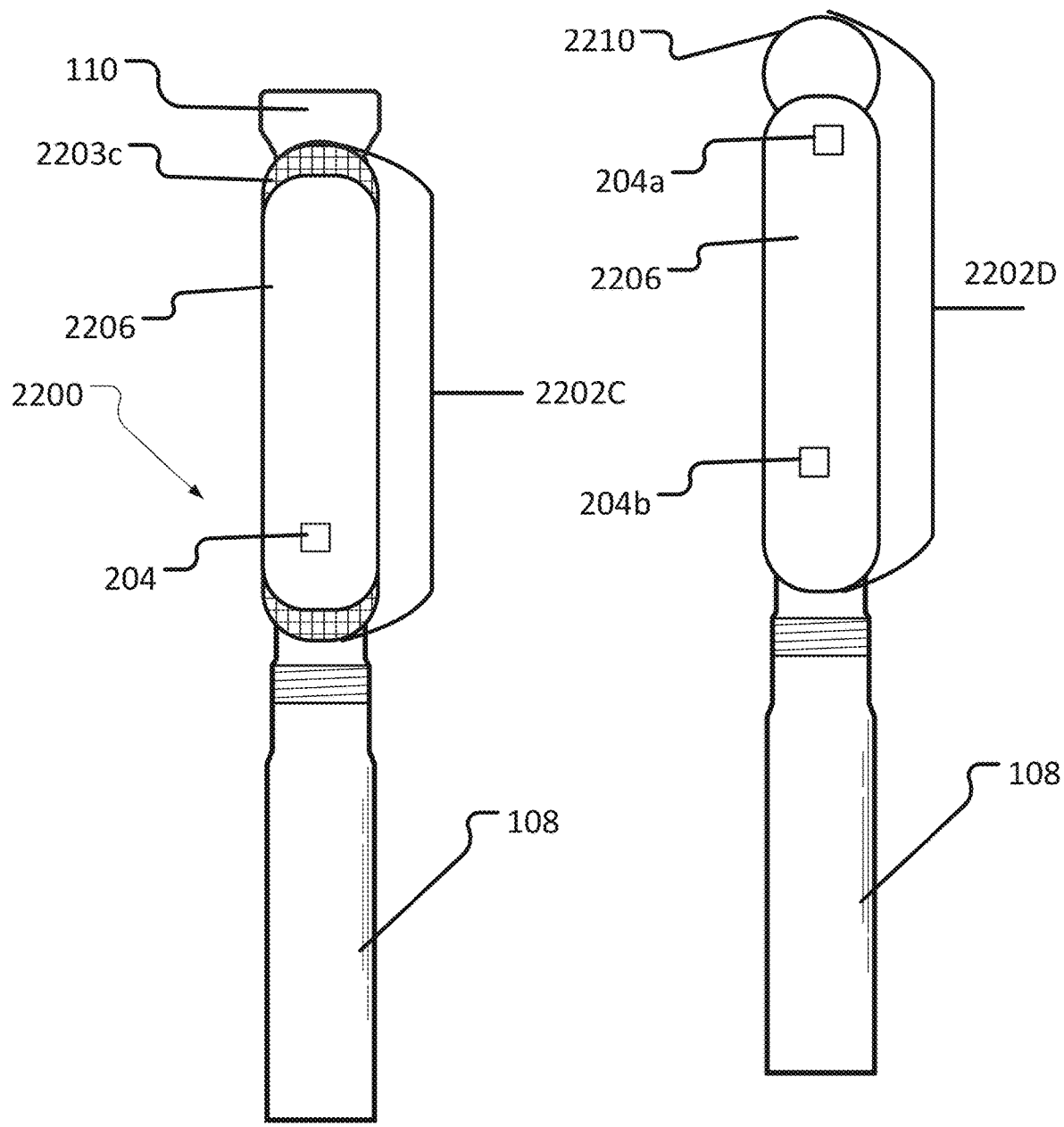

In FIG. 22A, section 2203a couples mostly with mouthpiece 110 and in FIGS. 22B and 22C, section 2203b and c couples mostly with the body of the cartridge 102. Sleeves 2202A and 2202B include mouthpiece 2210, whereas section 2203c of sleeve 2202C slips past mouthpiece 110 and leaves at least a portion of mouthpiece 110 exposed. Section 2203 may be two pieces attached at either end of sleeve 2202C or reside along the entire length of sleeve 2202C. Semi-rigid section of sleeve 2202D is not shown.

AME 2206 may be a passive AME such as refrigerant gel. AME 2206 may be rigid when in a frozen or cold state. In FIGS. 22A and 22B, AME 2206 modifies air downstream of heater, said air feeding mouthpiece 2210. In FIG. 22C, AME 2206 modifies air upstream of the heater, and in FIG. 22D, AME 2206 modifies air both upstream and downstream the heater as air enters in at least two places: air intake features 204a and 204b, which are respectively upstream and downstream of the heater.

Figure 23A:
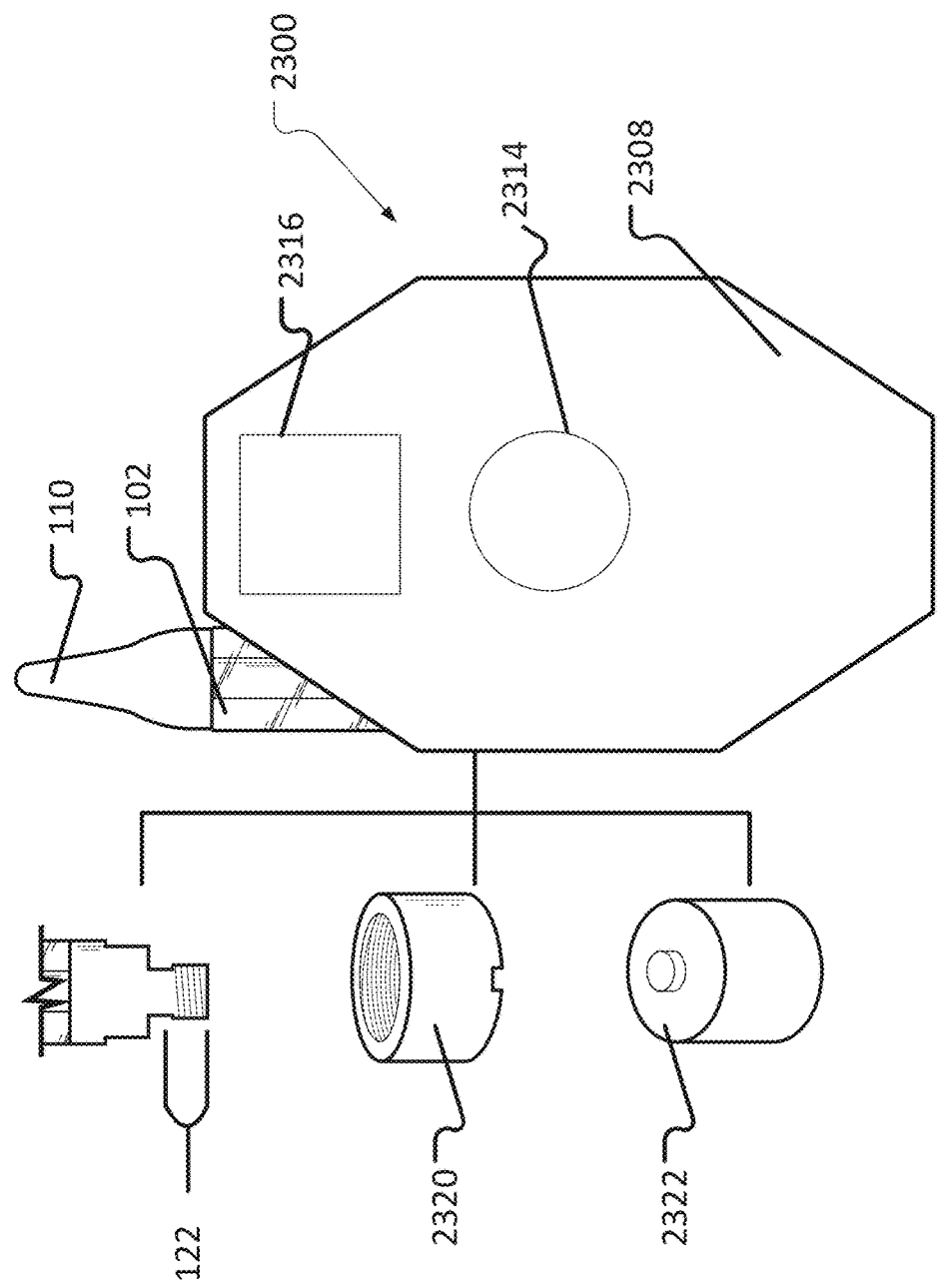
FIGS. 23A and 23B show a prior art portable vaporizer device.
Figure 23B:
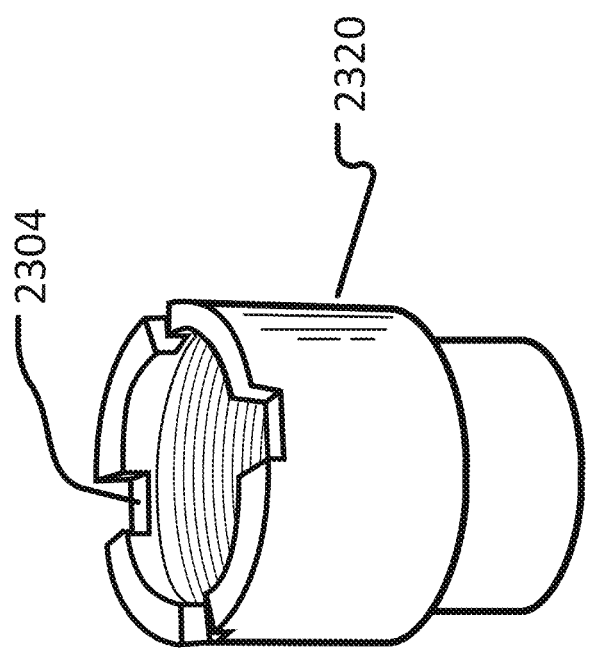

FIGS. 23A and 23B show prior art portable vaporizer device 2300, which includes battery section 2308, input button 2314, and display 2316. Device 2300 further includes cartridge 102 with mouthpiece 110, adapter 2320 defining air intake features 2304, and magnetic connector 2322. Adaptor 2320 mates with threading 122 of cartridge 102 and magnetic connector 2322 such that cartridge 102 is both mechanically and electrically connected to battery section 2308.

A user may adjust the applied voltage (and thus the intensity of a draw) by pushing a button (quickly) two or more times for cycling through a set of voltages (e.g., 3.5, 4.5, 6). The selected voltage level may be shown by display 2316 via a particular color.

Figure 24:
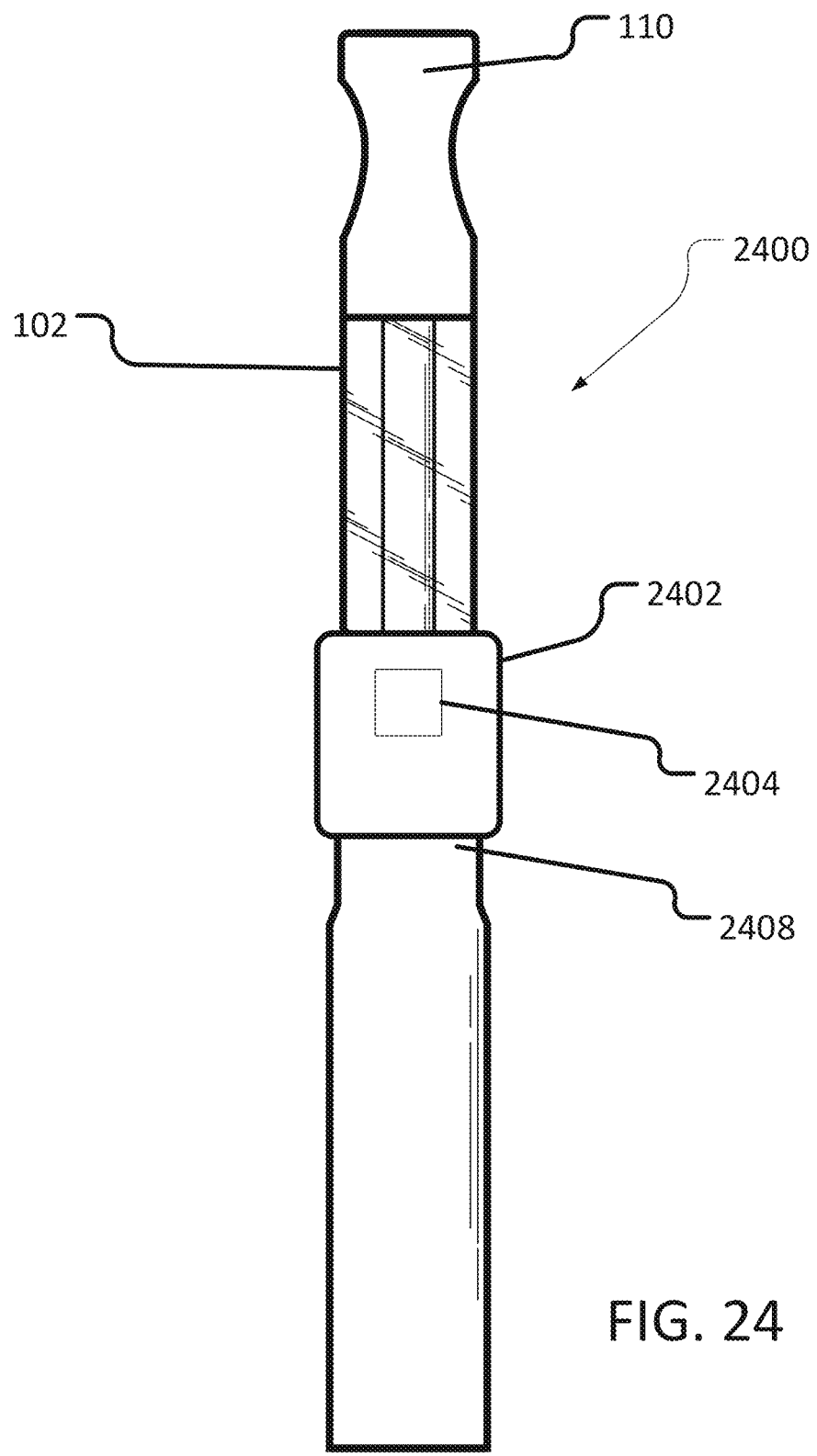
FIG. 24 shows a portable vaporizer device according to one or more aspects of the present invention.

FIG. 24 shows portable vaporizer device 2400, which includes adapter 2402, UI element 2404, battery section 2408, cartridge 102, and mouthpiece 110. Adapter 2402 may define a threaded, female connector on the proximal side of adapter 2402 and a male, threaded connector or other connector (e.g., a magnet or magnetizable material) on the distal side for connecting with battery section 2408.

UI element 2404 may change at least one of an aperture size of an air intake feature (not shown) or electrical property of adapter 2402. For example, UI element 2404 may be operably connected to a variable resistive element, thereby changing, for example, a resistance value between cartridge 102 and battery section 2408. In some embodiments, this resistance is series or parallel with a heater (not shown) of cartridge 102, thereby controlling the amount of current applied to said heater.

In other embodiments, battery section 2408 may read the user-set resistance of adapter 2402 and change a duty cycle or other periodic value applied by battery section 2408 for heating the heater. A user may modify a master duty cycle, which controls the ratio of ON to OFF time of a heater or a ratio of two applied voltages (e.g., a ratio of a high to low applied voltage). The master duty cycle may be selectively toggled among 25%, 50%, 75%, and 100% duty cycles with a total period of each cycle being between, for example, 1 and 3 seconds.

Figure 25:
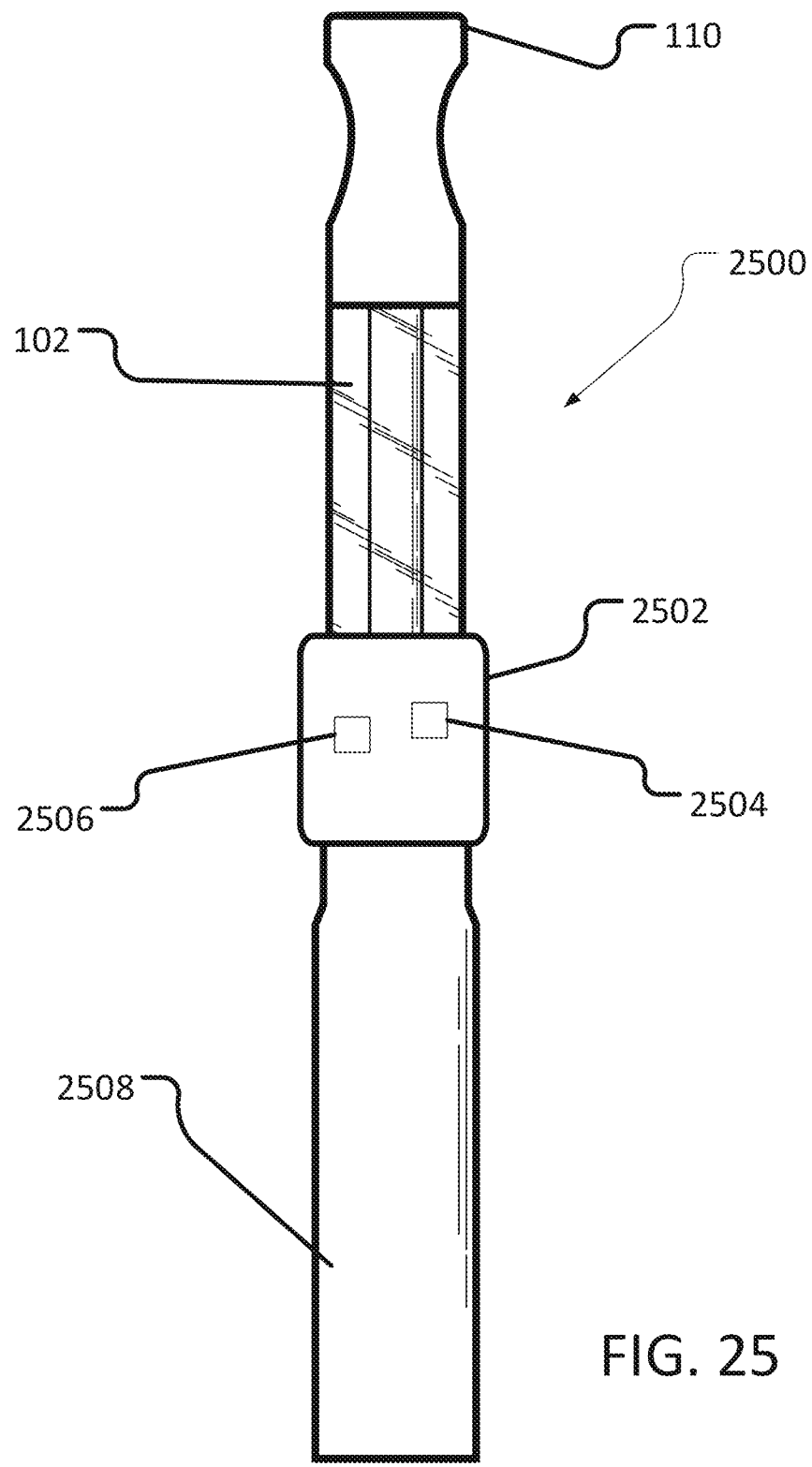
FIG. 25 shows a portable vaporizer device according to one or more aspects of the present invention.

FIG. 25 shows portable vaporizer device 2400, which includes adapter 2502, variable resistance UI element 2504, variable aperture UI element 2506, battery section 2408, cartridge 102, and mouthpiece 110. In comparison to adapter 2402, which may have a combined UI element controlling both aperture size of an air intake feature and resistance value or a UI element that changes just one of those two characteristics, adapter 2502 has two separate UI elements, elements 2504 and 2506.

Figure 26A:
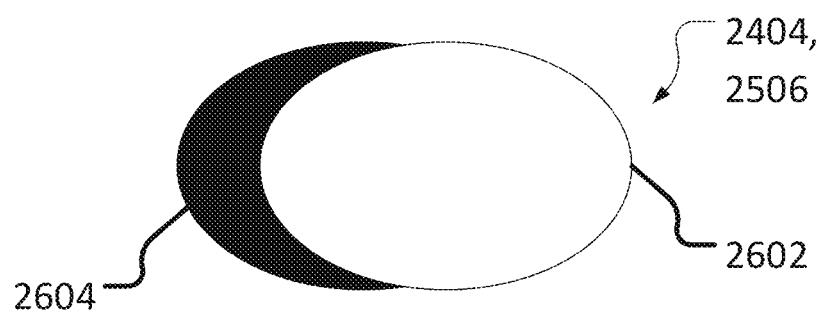
FIGS. 26A to 26C shows a portion of a portable vaporizer device according to one or more aspects of the present invention.
Figure 26B:
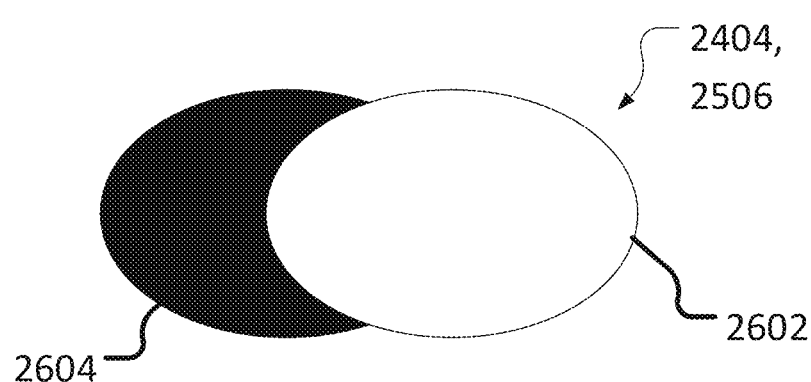
Figure 26C:
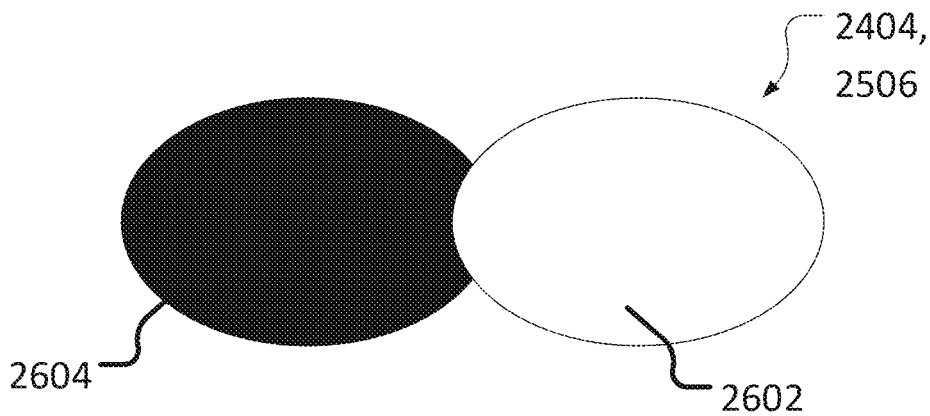

For example, FIGS. 26A to C show slider 2602 and aperture 2604 example embodiments of variable UI elements 2404 and 2406, in which aperture 2604 is in fluid communication with a heater. Slider 2602 controls at least the aperture size of aperture 2604, and thereby the relative size of the air intake feature of adapters 2402 and 2502. Slider 2602 may further control a variable resistive element, and thereby, for example, change the electrical load resistance, as seen from the power source (e.g., the combined resistance of a cartridge and potentiometer arranged in series and powered by a battery).

In one embodiment, slider 2602 when is in the most "open" position (i.e., biggest size of aperture 2604), it is also positioned a potentiometer in its lowest-possible resistance value and vise-versa. This particular embodiment may be welcomed since that may represent the highest current applied to a heater, if connected in series, and thus the need to bring in as much air as possible via the relatively enlarged aperture 2604.

Figure 27:
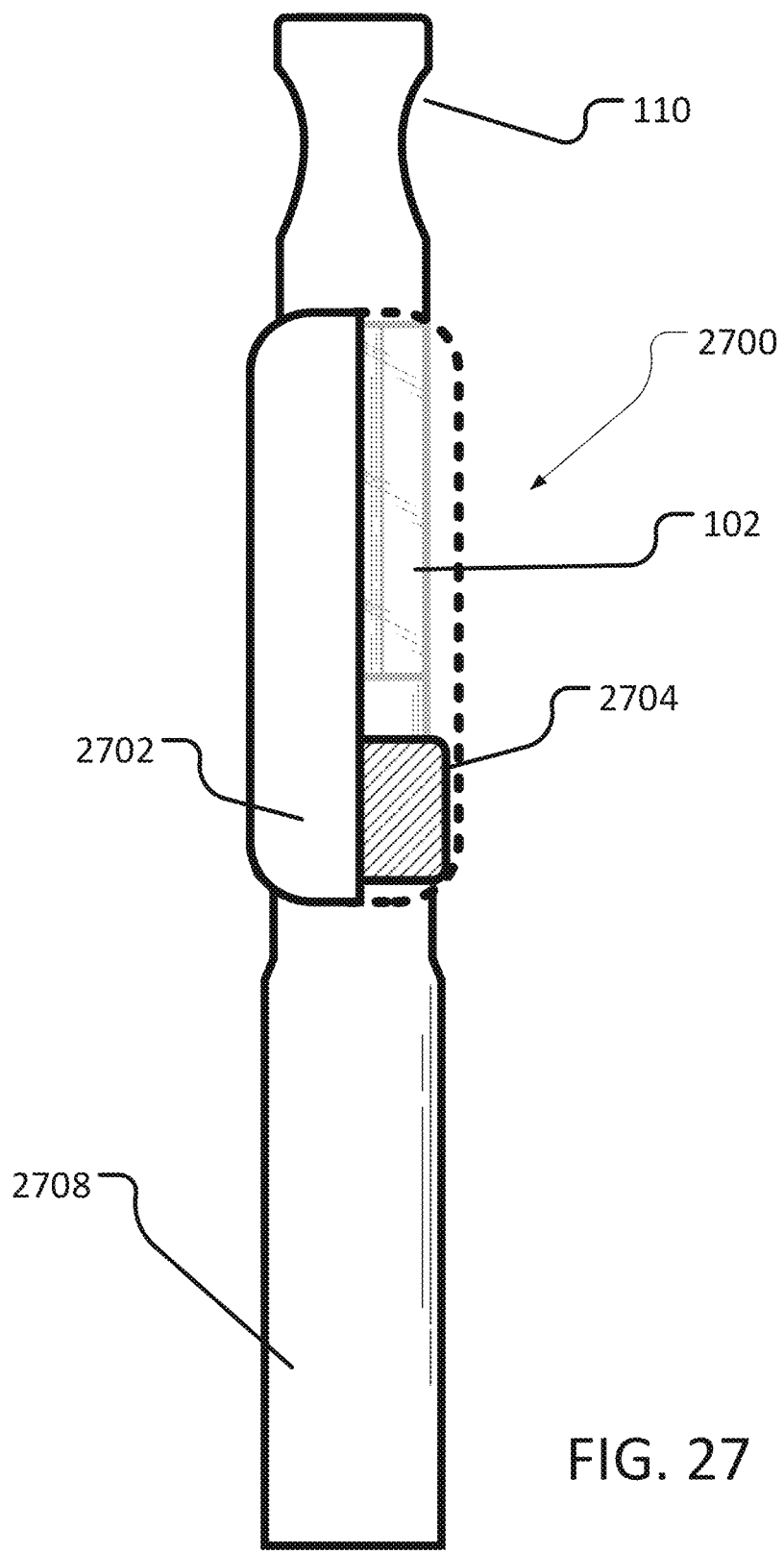
FIG. 27 shows a portable vaporizer device according to one or more aspects of the present invention.

FIG. 27 is a schematic cutaway that shows portable vaporizer device 2700, which includes sleeve 2702, which shows only the left haft and the outline of the right half for showing cartridge 102 and adapter 2704, both of which is at least partially surrounded by sleeve 2702. Adapter 2704 electrically couples with battery section 2708 and cartridge 102. In some embodiments, adapter 2704 and/or sleeve 2702 includes active circuitry such as a controller. In such embodiments, a sleeve or adapter may perform one of the many periodic control schemes described herein.

Figure 28:
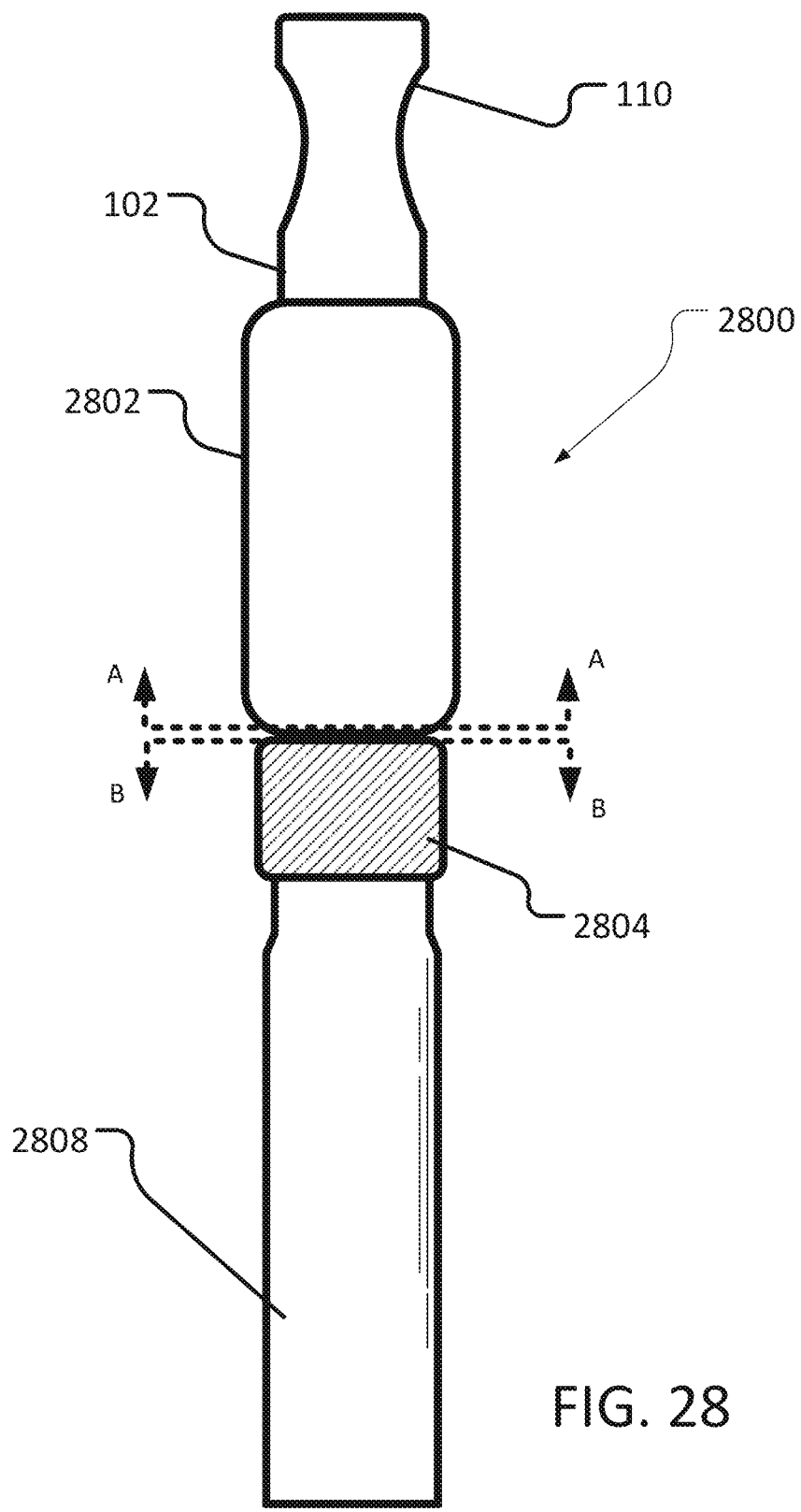
FIG. 28 shows a portable vaporizer device according to one or more aspects of the present invention.

FIG. 28 shows portable vaporizer device 2800 with sleeve 2802 and adapter 2804. Thus, adapter 2804 electrically couples both cartridge 110 and sleeve 2802 with battery 2808.

Figure 29:
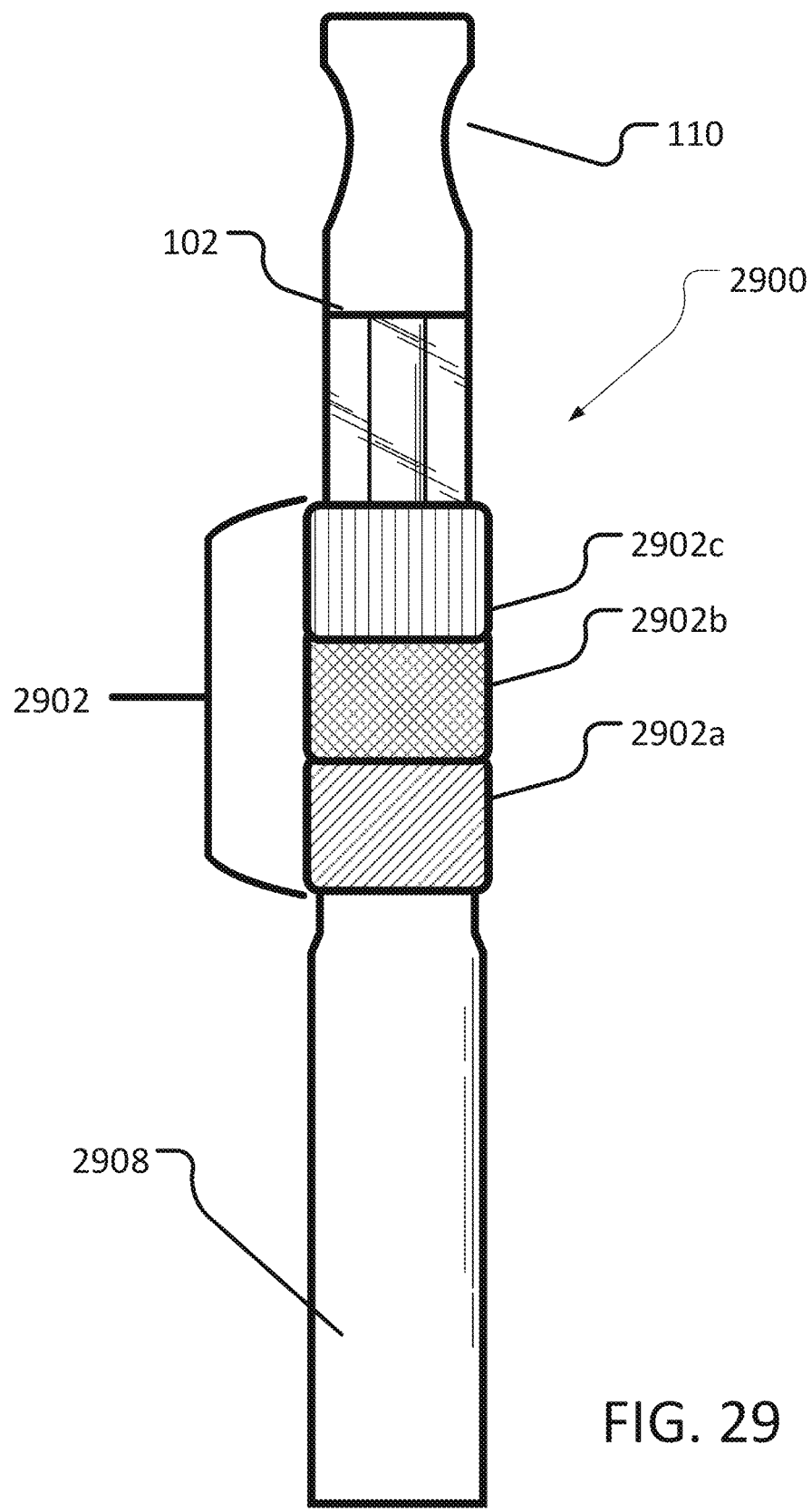
FIG. 29 shows a portable vaporizer device according to one or more aspects of the present invention.

FIG. 29 shows portable vaporizer device 2900 with sleeve 2902, which includes two or more modules. Module 2902a may be an adapter or a sub-sleeve, where the former may electrically couple, if at all, modules 2902b and 2902c to battery 2908 and the latter (i.e., a sub-sleeve) may also or instead modify intake air supplied from modules 2902b and 2902c.

Modules 2902a, 2902b, 2902c may be passive and/or active AME. Modules with passive AMEs, may include media such as phase change materials in a solid or "cold" state, liquid water, or metal. Active AMEs may change a "local" temperature of a passive AME (e.g., a Peltier element module thermally coupled to a metal or liquid water module). Sub-sleeves may be integral within a sleeve housing and/or removably coupled to each other by threaded, mechanical, or magnetic couplers.

Figure 30:
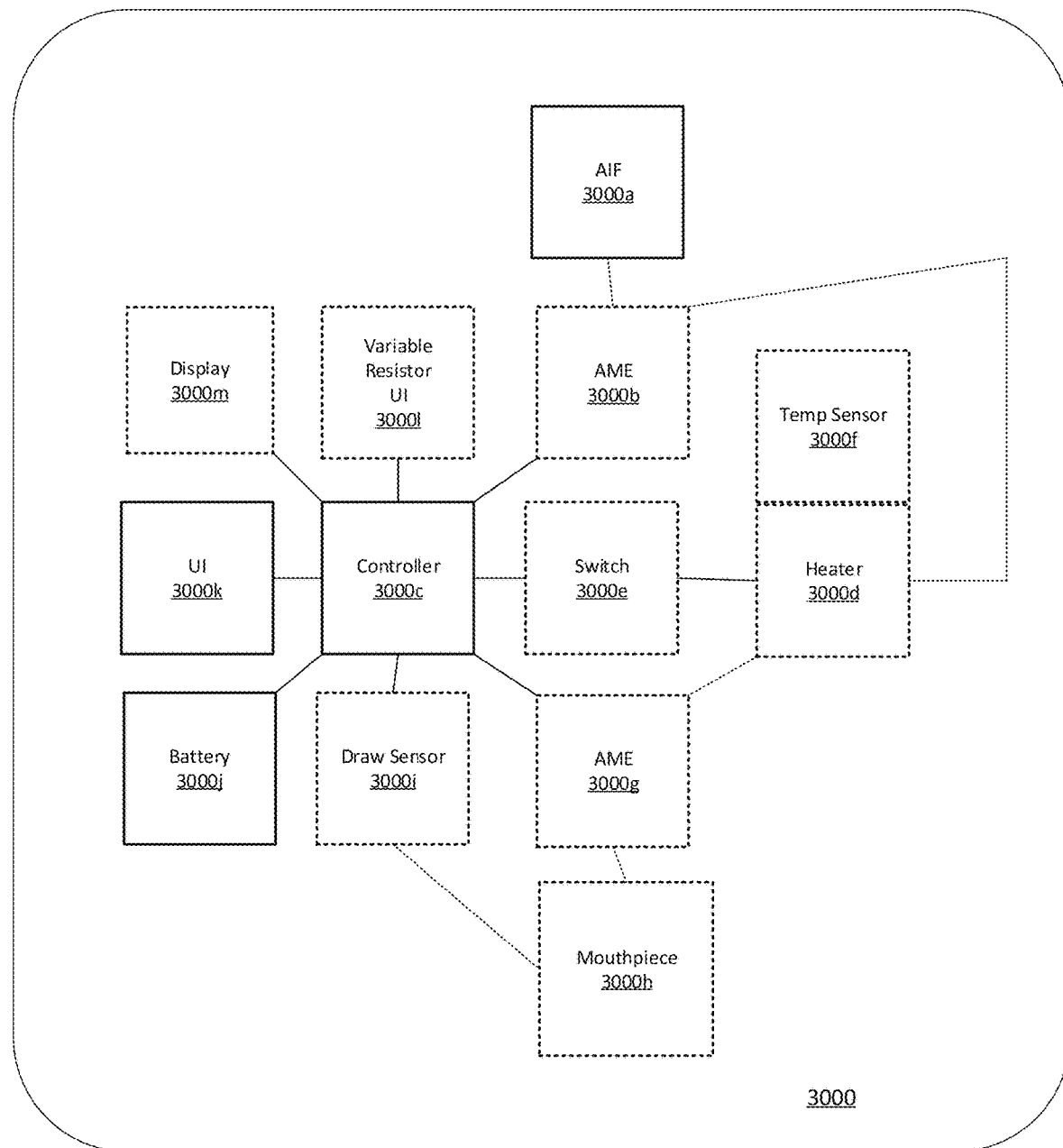
FIG. 30 shows a vaporizer device according to one or more aspects of the present invention.
Figure 32B:
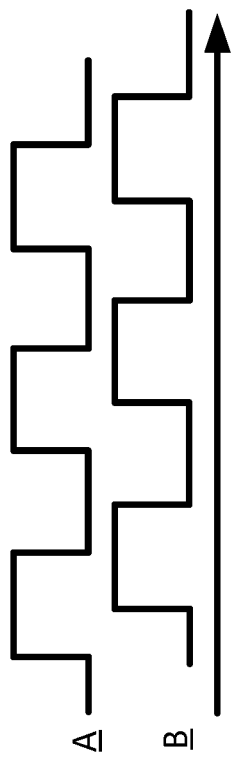
FIGS. 32A to D show various low-frequency duty cycles according to one or more aspects of the present invention.
Figure 32D:
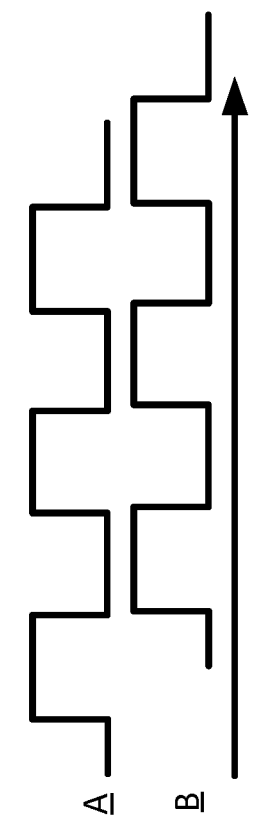
Figure 32A:
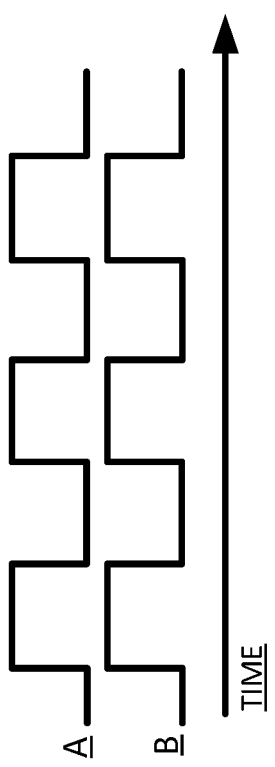
Figure 32C:
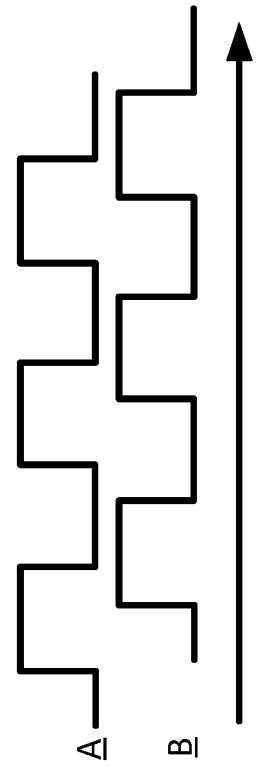

FIG. 30 shows portable vaporizer device 3000, with non-essential features shown with dashed lines. Vaporization device, portable or not, 3000 includes air intake feature 3000a in fluid communication with AME 3000b, which may be electrically coupled to controller 3000c and in fluid commination with heater 3000d. Heater 3000d may be electrically coupled to at least one of controller 3000c and switch 3000e. Temperature sensor 3000f is typically thermally coupled to heater 3000d or an oven. Said sensor 3000f is also typically electrically coupled to controller 3000c or a similar device.

Heater 3000d may also be in fluid communication with AME 3000g, which may be electrically coupled to controller 3000c and in fluid communication with mouthpiece 3000h. Mouthpiece 3000h may be in fluid communication with draw sensor 3000i, which is typically electrically coupled to controller 3000c or a similar device.

Battery 3000j is typically electrically coupled to controller 3000c, but may also be (or another battery is) connected to switch 3000e. UI elements may include UI element 3000k and/or variable-resistor UI element 3000l. Variable-resistor UI element 3000l may be coupled to controller 3000c or control a variable resistor arranged, electrically, between battery 3000j and heater 3000d. Display 3000m is typically electrically coupled to controller 3000c or a similar device.

FIGS. 31A to 31E show various low-frequency periodic signals/waveforms A, B, C, which may be representative of a control signal (e.g., a signal generated by controller for a switch), a temporally applied voltage or current level (e.g., a signal that is a variable time-domain voltage applied by a battery to a heater), a measured heater temperature, or a resistance level of a variable resistor electrically coupled to a heater, among other possible examples of what the waveforms represent.

In some embodiments, the "shape" of the low-frequency signal/waveform may be chosen by a user. For example, the user may cycle among "square", "triangle" and "curved" shapes/modes as respectively shown in 31A, 31B, 31C, among other possible shapes. Further, a user may toggle between or cycle among two or more periodic values. This may be a duty-cycle percentage (e.g., electing among waveforms A, B, and C of FIG. 31A), a temporal value, or a frequency value (e.g., selecting among waveforms A, B, and C of FIG. 31B or 31C). Further still, a user may choose the high/maximum and/or low/minimum values of the low-frequency signal (e.g., 0 and 5 volts, 1 and 4 volts, 2 and 3 volts, etc. . . . ) as shown in FIGS. 31D and 31E.

Representative "low-frequency" values may include 30 Hz to 0.5 Hz. For example, each (corresponding) rising edge or curve may occur every 0.5 to 2 seconds.

FIGS. 32A to 32D show various low-frequency periodic signals/waveforms A and B, which show respective low-frequency duty cycles for a heater circuit (duty cycle A, which may control a heater or, for example, an electrically coupled variable resistor) and an active AME circuit (duty cycle B). Although voltage duty cycles are shown, other periodic signals (and representative values thereof (e.g., resistance, temperature, etc. . . . ) are possible, such as those shown in the previous figures. The duty cycles shown in 32A to 32D may toggle from a null or zero value to a non-zero value or toggle between two non-zero values (e.g., 0.5 volt and 3 volts).

The waveforms of FIGS. 32A to 32D each have a phase shift from one another. For example, a user may select the relative phase between waveforms A and B such that a user may pick the AME and heater circuits to operate completely in-phase, completely out-of-phase or at a phase relationship in-between. Thus, a user has control over a vaporizer's operation that is not expressed in the state of the art: relative phase control, by a user, among two or more "active" elements of a heater circuit, an AME circuit, or both.

Figure 33:
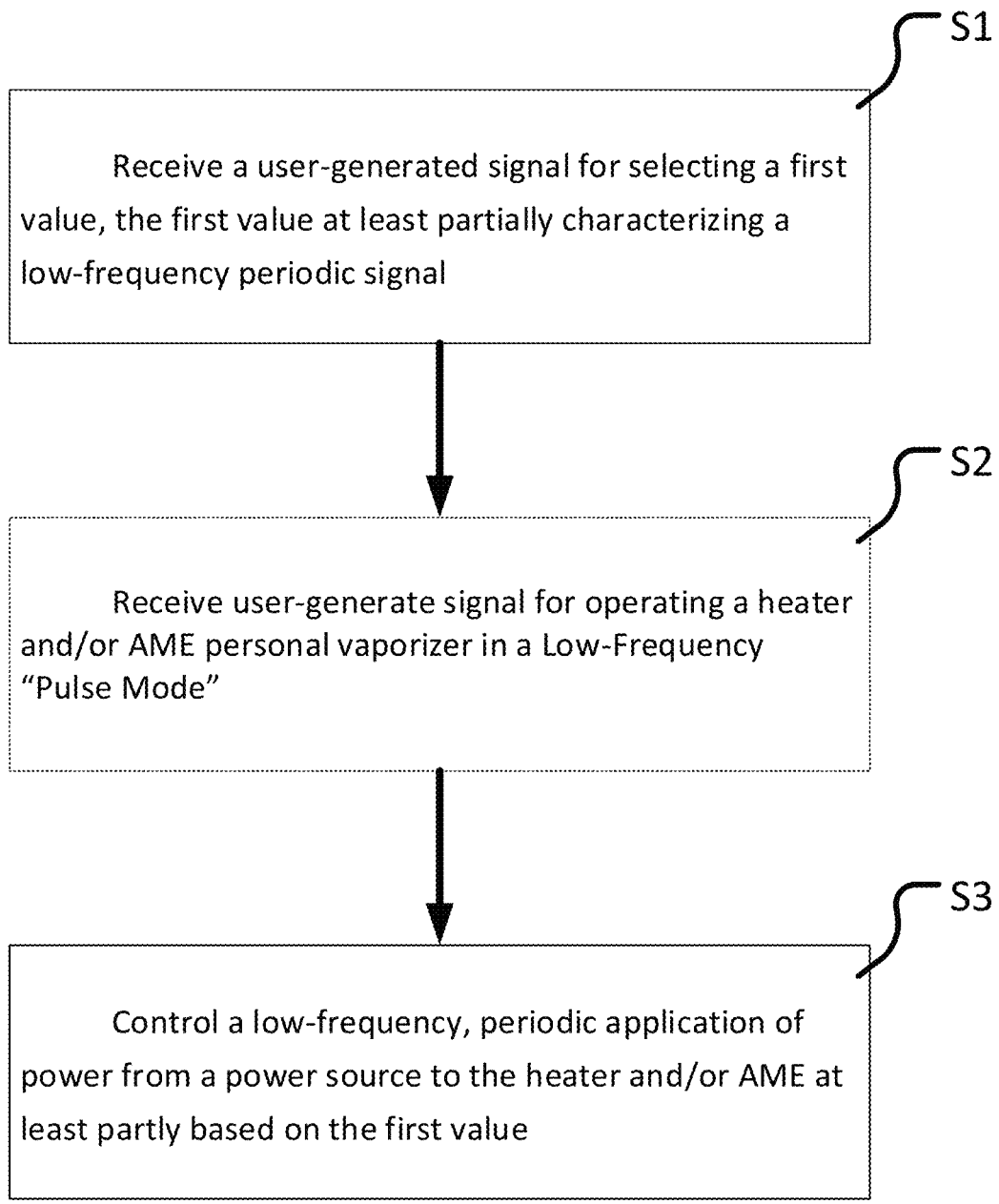
FIG. 33 shows a vaporizer method according to one or more aspects of the present invention.

FIG. 33 shows a method of operating a personal vaporizer, with an optional step S2. At S1, a controller, for example, may receive a user-generated signal for selecting a first value, the first value at least partially characterizing a low-frequency periodic signal. The different ways that this characterization may be generated and values of said characterization have been discussed above and in the claim below.

At S2, a controller may receive a user-generate signal for operating a heater and/or AME personal vaporizer in a Low-Frequency "Pulse Mode". In some embodiments, the vaporizer may operate in a steady state or constant temperature mode and a user may cycle among two or more possible operation modes, including an operation mode that utilizes a low-frequency control signal or some other low-frequency signal.

At S3, a controller may control a low-frequency, periodic application of power from a power source (e.g., a battery) to the heater and/or AME at least partly based on the first value. This value may control both the heater and AME or only one of the two. The value may be input from a tactile user input (e.g., a button or slider), a user shaking the device, or a draw sensor.

For example, as a user takes a stronger draw, as measured by a draw sensor, a controller may increase the duty cycle percentage value up to 100% (e.g., steady state). Conversely, "weaker" draws will decrease a duty cycle percentage value down to a minimum, non-zero number (e.g., 25% or 50%). By modifying the low-frequency periodic application of power based on draw strength, a user can obtain a wide range of draw "strengths" based on the intensity/strength of a user's draw (e.g., measured flow strength from a draw sensor such as an airflow meter).

Figure 34A:
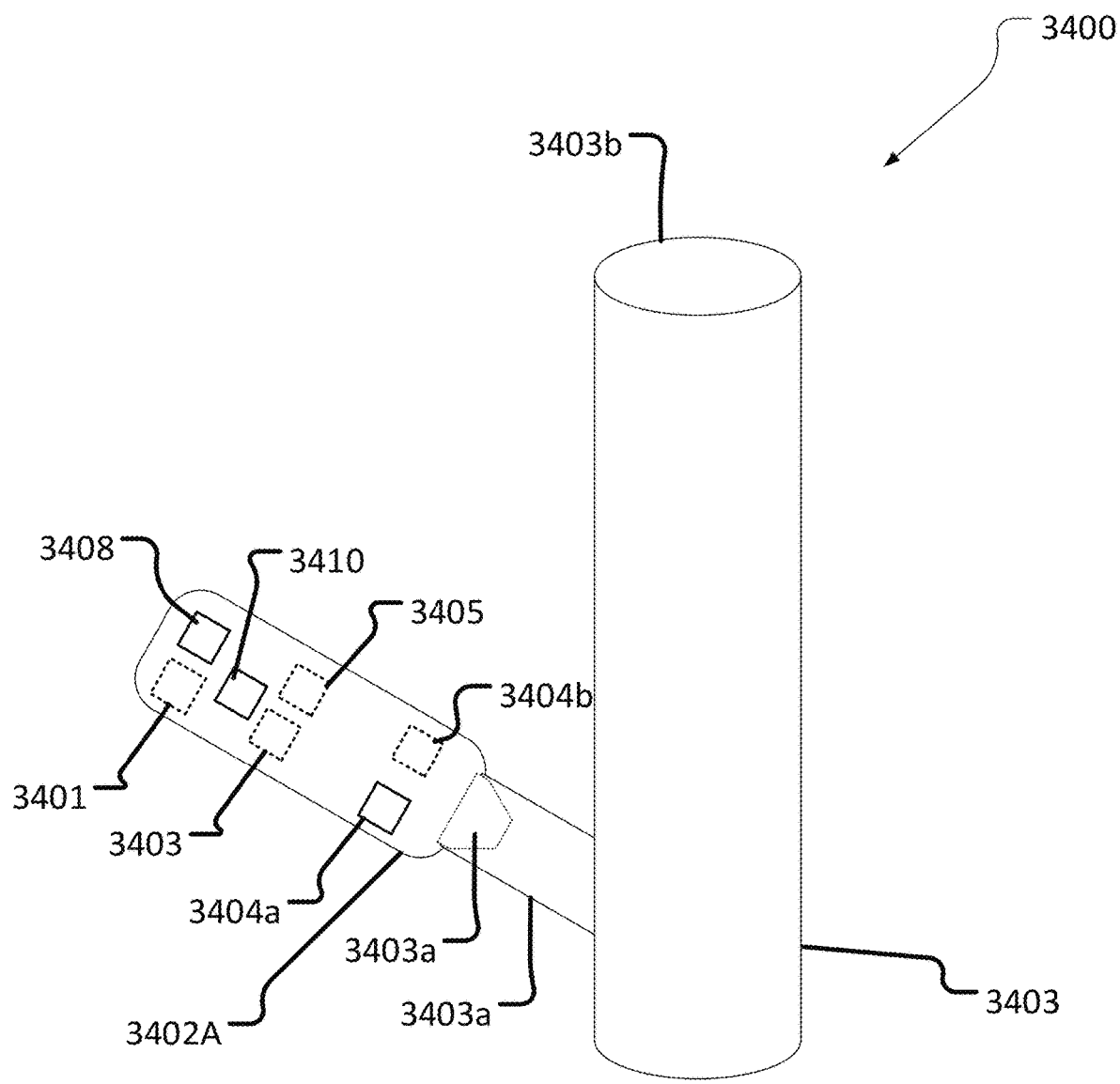

FIG. 34A shows personal vaporizer device 3400, which includes vaporizer 3402a coupled to water pipe 3403 or "bong" in the common parlance. Water pipe 2202 includes stem 3403a, which is coupled to stem interface 3403a, which forms an air-tight or near-air-tight seal and thereby establishing an airpath channel that spans air intake features 3404a and mouth interface 3404b, from which a user establishes a similar seal and takes a draw. Vaporizer 3402a may also include battery 3408, controller 3410, draw sensor 3401, heater 3403, and UI element 3405.

Device 3402A may be an herbal, oil, and/or cartridge vaporizer. That is, depending on configuration, device 3402 may vaporize at least one of herbs (e.g., "flower"), extract oils, or accepted a cartridge that contains herb or oil.

For example, vaporizer 3402B of FIGS. 34B, 34C and 34D is a sleeve adapted to accept cartridge 3412 and form airpath channel 3414, which spans from air intake features 3404a and 3404b to the end of stem interface 3403a. Vaporizer 3402b includes connector 3418 for coupling with a section of cartridge 3412 and electrically coupling cartridge 3412 with sleeve vaporizer 3402B. Once the cartridge is placed in sleeve vaporizer 3402B, sleeve 3402B may be closed, for example, in any manner provided in FIGS. 5B to 5F, except "mouthpiece" 502a would not be a mouthpiece, but rather a "lid" that may partially define, internally of sleeve 3402B, airpath channel 3414, when closed/coupled to sleeve 3402B.

In alternative embodiments, cartridge 3412 is first connected to connector 3418 and then sleeve vaporizer 3403B is "slid" over cartridge 3412.

Figure 35:
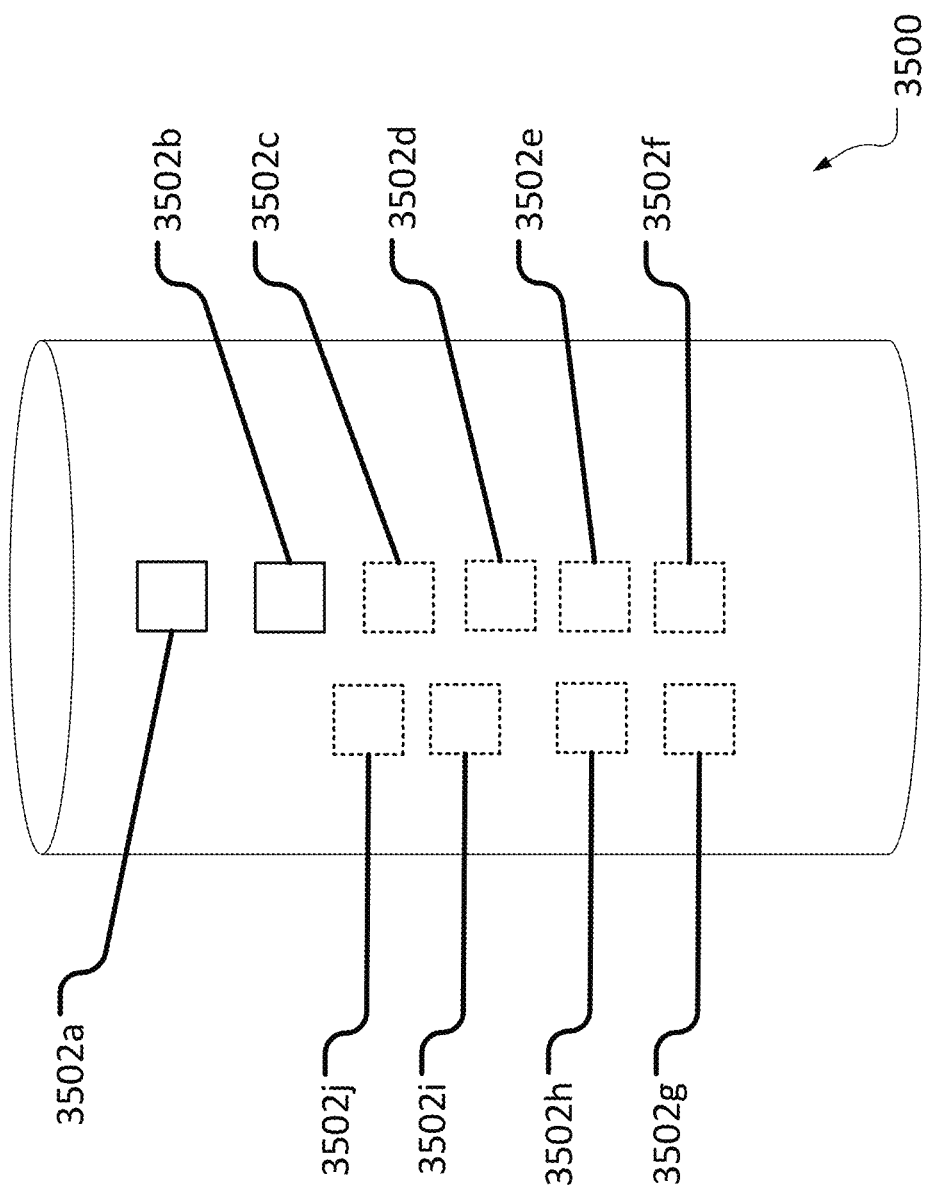
FIG. 35 shows a vaporizer method according to one or more aspects of the present invention.

FIG. 35 shows personal vaporizer device 3500, device 3500 includes air intake feature 3502a, one or more of AME 3502b, user input sensor 3502c, variable resistance element 3502d, draw sensor 3502e (which may be a type of user input sensor), display 3502f, controller 3502g, and switch 3502h for selectively applying power from a battery to, for example, two or more heaters 3502i and 3502j such as multiple cartridge's heaters, multiple ovens, or a combination thereof. Embodiments include alternating between, for example, vaping a cartridge's oil and an herbal chamber for a mixed experience/inhalation draw. Alternative embodiments include alternating the vaporizing between two different herbal chambers or cartridges. Embodiments may also include maintaining a vaporizing temperature for one herbal chamber or cartridge via first heater and intermittently vaporizing, via a second heater, material in a second herbal chamber or cartridge.

Figure 36A:
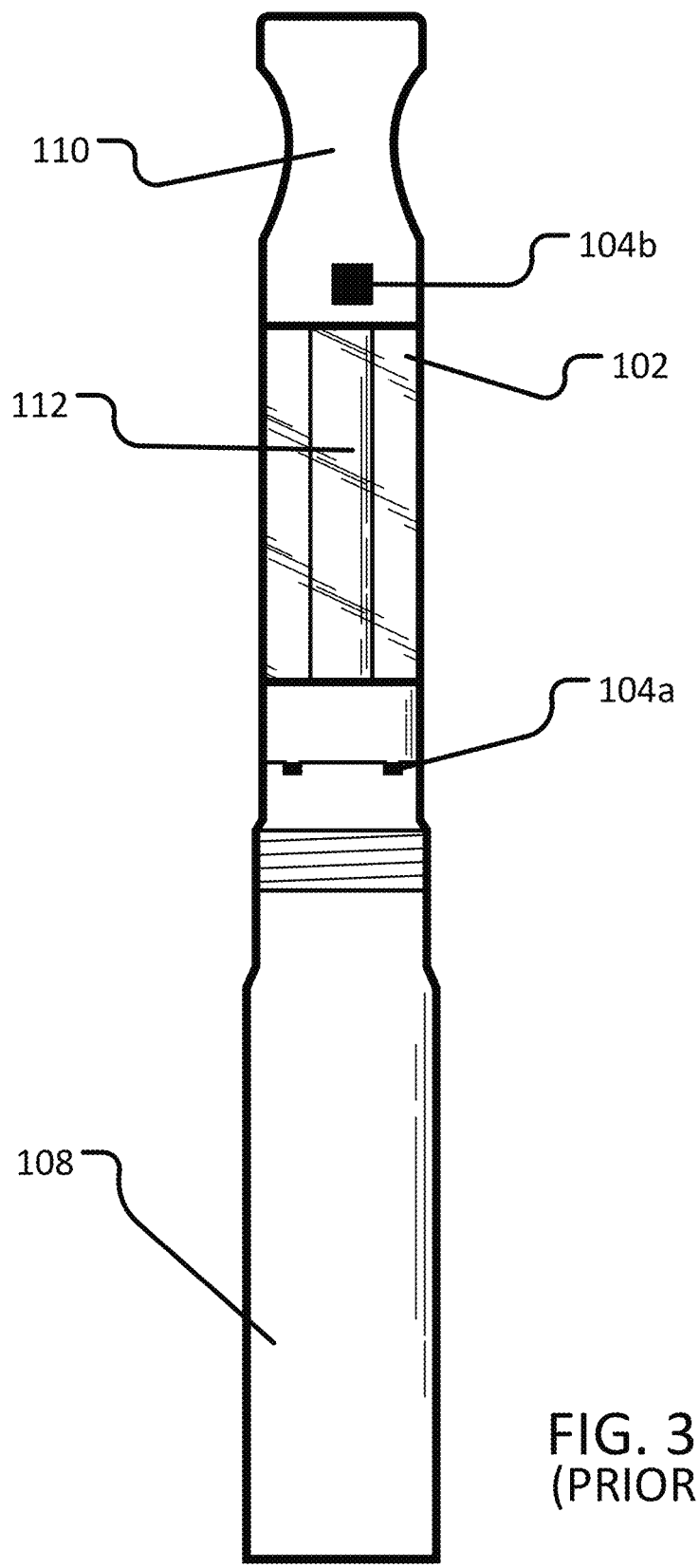
FIG. 36A shows a prior art portable vaporizer system.

FIG. 36A shows a prior art portable vaporizer device that is similar to system 100 except air intake features 104a and 104b are respectively arranged downstream and upstream a cartridge heater (not shown). Air intake feature 104b "mixes" ambient air and heated air being carried along post-heater airpath 112 before the mixed air exits the mouthpiece.

Figure 36B:
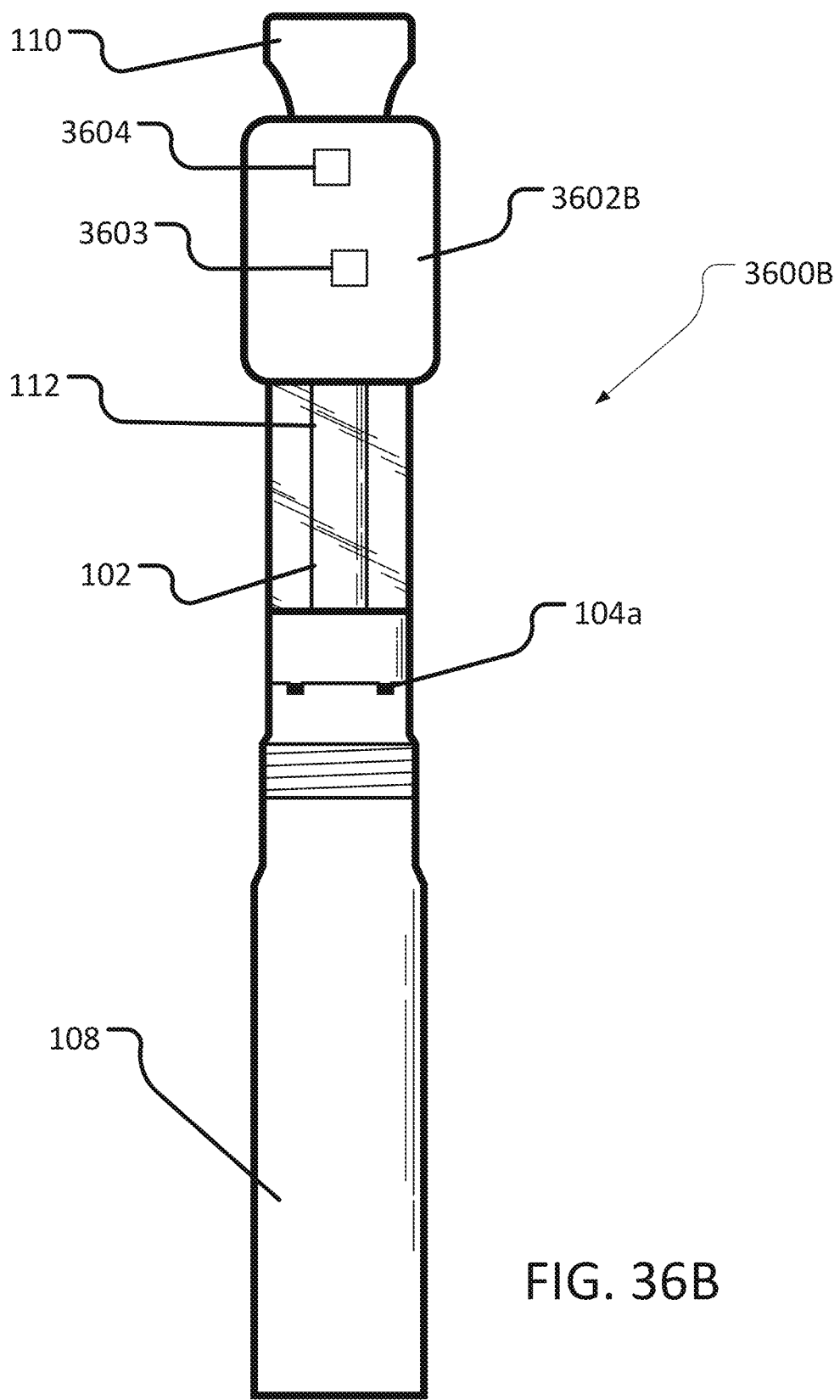
FIGS. 36B and 36C show a portable vaporizer device according to one or more aspects of the present invention.

In FIG. 36B, system 3600B includes sleeve 3602B. Sleeve 3602B includes AME 3603 arranged in fluid communication with air intake features 104b and 3604. Thus, AME 3603 is arranged to modify at least one of a temperature and/or moisture content of air that is passing through (or along) sleeve 3602B before entering air intake feature 104b.

Figure 36C:
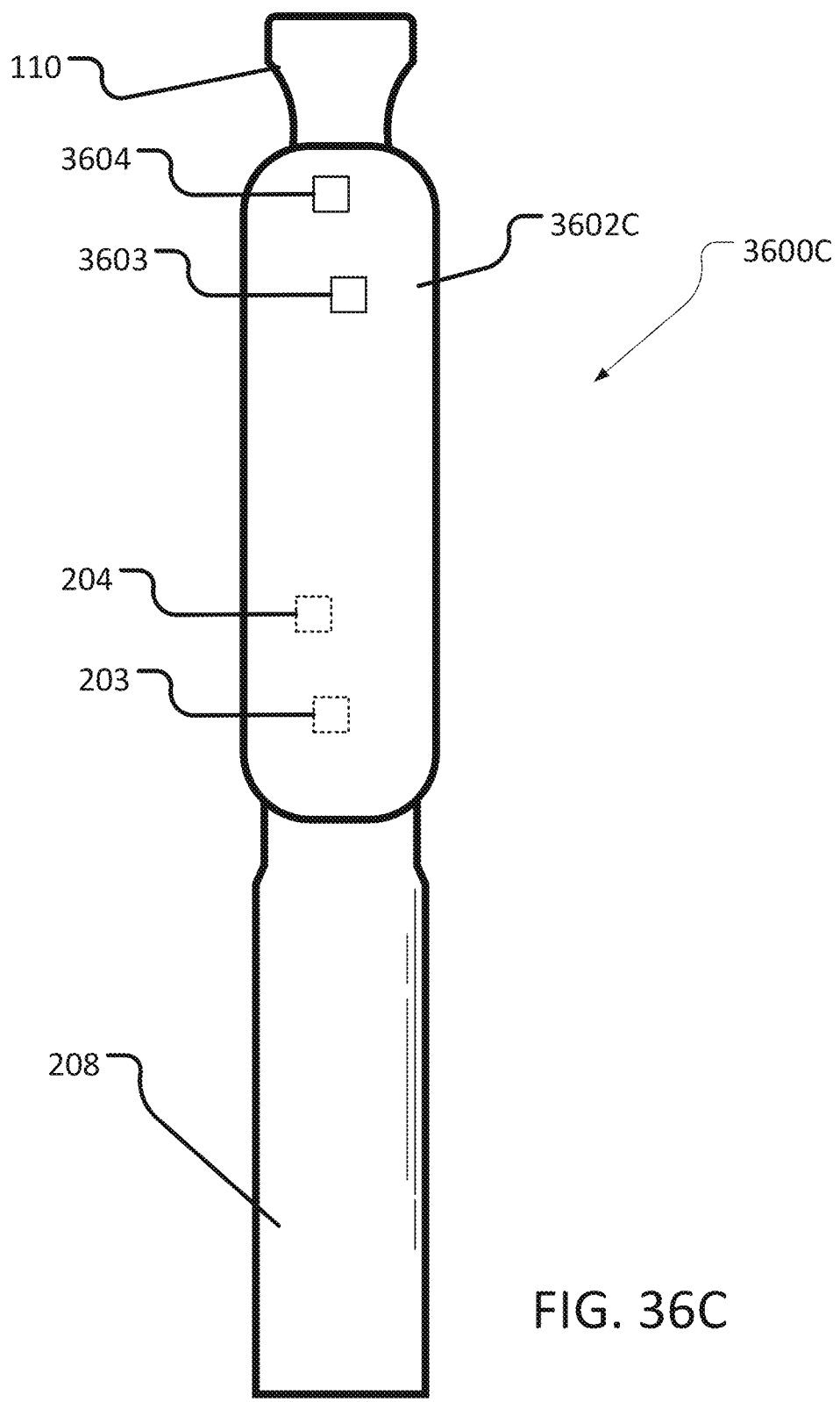

In FIG. 36C, system 3600C includes sleeve 3602C. Sleeve 3602 may further include AME 203 and air intake feature 204. Thus, sleeve 3602C may condition air both downstream and upstream a cartridge's heater. Said conditioning may be performed by AME 3603 or with separate AMEs: AME 203 for conditioning downstream the heater and AME 3603 for conditioning upstream the heater.

Programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

What is claimed is:

1. A device for providing an inhalable vapor from a cartridge mouthpiece of a cartridge, the device comprising:
   a sleeve having a sleeve mouthpiece which defines a sleeve mouthpiece outlet end; and
   a body comprising a battery, the body including a body distal section and a body proximal section, the body proximal section comprising:
      a first connector arranged to electrically couple with the cartridge that provides a volatizable material; and
      a second connector arranged to releasably couple with the sleeve, the second connector defining a periphery that is wider than a periphery defined by the first connector and the first and second connectors having a common longitudinal axis, with the sleeve adapted to be releasably coupled to the second connector, the sleeve defining a volume that is dimensioned for encapsulating the cartridge and the cartridge mouthpiece, and the sleeve mouthpiece outlet end arranged or arrangeable to be downstream of a cartridge mouthpiece proximal end and in fluid communication with the cartridge mouthpiece when both the cartridge and the sleeve are respectively coupled to the first and second connectors.

2. The device of claim 1, with the sleeve comprising at least one sub-sleeve adapted to releasably couple with the sleeve mouthpiece at a sub-sleeve proximal section and the second connector at a sub-sleeve distal section, the at least one sub-sleeve defining a first aperture that is sufficiently dimensioned to accommodate a width of the cartridge.

3. The device of claim 1, with the body at least partially defining at least one body air intake feature that is in fluid communication with the sleeve mouthpiece outlet end.

4. The device of claim 1, with the sleeve mouthpiece adapted to releasably couple with a section of the sleeve.

5. The device of claim 2, with the first connector comprising a first threaded section, the second connector comprising a second threaded section, the sub-sleeve distal section comprising a third threaded section, the sub-sleeve proximal section comprising a fourth threaded section, and a sleeve mouthpiece distal section comprising a fifth threaded section.

6. The device of claim 1, with the first connector comprising one of a threaded section and a magnetic coupling element.

7. The device of claim 1, with the second connector comprising one of a threaded section and a magnetic coupling element.

8. The device of claim 1, with the first connector and the second connector comprising a first magnet.

9. The device of claim 1, further comprising the cartridge.

10. The device of claim 1, with the sleeve comprising a first sub-sleeve and a second sub-sleeve, each being adapted to releasably couple with the sleeve mouthpiece at a respective sub-sleeve proximal section and the second connector at a respective sub-sleeve distal section, the first and second sub-sleeves defining a respective aperture that is sufficiently dimensioned to accommodate a width of the cartridge.

11. The device of claim 1, with the sleeve dimensioned to accommodate the length of the cartridge.

12. The device of claim 1, with the sleeve defining a hollow cylinder.

13. The device of claim 1, with the sleeve defining a hollow cylinder with the volume that is dimensioned for encapsulating the cartridge and the cartridge mouthpiece.

14. The device of claim 4, with the sleeve mouthpiece adapted to releasably couple with a threaded section of the sleeve.

15. The device of claim 4, with the sleeve mouthpiece adapted to releasably couple with a magnetic section of the sleeve.

* * * * *